(12) United States Patent
Terada et al.

(10) Patent No.: US 7,902,207 B2
(45) Date of Patent: Mar. 8, 2011

(54) PROCESS FOR PRODUCTION OF AMINES

(75) Inventors: Masahiro Terada, Sendai (JP); Daisuke Uraguchi, Nagoya (JP); Keiichi Sorimachi, Sendai (JP); Hideo Shimizu, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 1057 days.

(21) Appl. No.: 10/587,279

(22) PCT Filed: Jan. 26, 2005

(86) PCT No.: PCT/JP2005/000962
§ 371 (c)(1),
(2), (4) Date: Sep. 13, 2006

(87) PCT Pub. No.: WO2005/070875
PCT Pub. Date: Aug. 4, 2005

(65) Prior Publication Data
US 2007/0142639 A1    Jun. 21, 2007

(30) Foreign Application Priority Data
Jan. 26, 2004 (JP) ................ 2004-017725

(51) Int. Cl.
*C07F 9/02* (2006.01)
(52) U.S. Cl. ............ 514/282; 558/83; 549/491; 546/176
(58) Field of Classification Search .......... 514/282; 546/176; 549/491; 558/83
See application file for complete search history.

(56) References Cited

U.S. PATENT DOCUMENTS
2004/0030145 A1    2/2004 Jendralla et al.

FOREIGN PATENT DOCUMENTS
EP    1134209 A1 *  9/2001
WO    03/093259      11/2003

OTHER PUBLICATIONS

D. Uraguchi et al., "Chiral Bronsted Acid-Catalyzed Direct Mannich Reactions via Electrophilic Activation", Journal of the American Chemical Society, vol. 126, No. 17, pp. 5356-5357, 2004.
D. Uraguchi et al., "Organocatalytic Asymmetric Aza-Friedel-Crafts Alkylation of Furan", Journal of the American Chemical Society, vol. 126, No. 38, pp. 11804-11805, 2004.

* cited by examiner

*Primary Examiner* — Sreeni Padmanabhan
*Assistant Examiner* — Sahar Javanmard
(74) *Attorney, Agent, or Firm* — Sughrue Mion, PLLC

(57) ABSTRACT

A process for producing an amine which is characterized by reacting an imine with a nucleophilic compound (except a trialkylsilyl vinyl ether) in the presence of a phosphoric acid derivative represented by the formula (1):

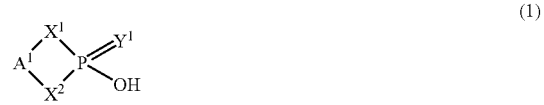

(1)

wherein $A^1$ represents a spacer; $X^1$ and $X^2$ represent each independently a divalent nonmetal atom or a divalent nonmetal atomic group; and $Y^1$ is oxygen or sulfur. The invention provides a process by which amines (particularly optically active amines) useful as intermediates of medicines, agricultural chemicals, or the like can be produced without special post-treatment in high yield at high optical purity; and phosphoric acid derivatives (particularly optically active phosphoric acid derivatives) useful in the production of the amines.

4 Claims, No Drawings

PROCESS FOR PRODUCTION OF AMINES

This is a national stage application under 35 U.S.C. 371 of PCT/JP2005/000962 filed on Jan. 26, 2005, which claims priority from Japanese patent application 2004-017725 filed on Jan. 26, 2004, all of which are incorporated herein by reference.

BACKGROUND OF THE INVENTION

1. Field of the Invention

The present invention relates to a process for producing amines useful as intermediate or the like for medicines, agricultural chemicals or the like.

2. Description of the Related Art

Previously, for a process for producing of an optically active intermediate used for medicines, agricultural chemicals or the like, for example, methods using a metal compound have been known. However, the method has a problem that must dispose of the metal compound used.

In order to solve such problem, Non-patent Literature 1 (J. Org. Chem., Vol. 68, No. 25, 9624 (2003)) and Non-patent Literature 2 (J. Am. Chem. Soc., Vol. 24, No. 9, 1842 (2002)) report a method of reacting a carbonyl compound and an imine using L-proline or a derivative thereof in place of a metal compound.

However, the method described in the Non-patent Literature 1 has a problem that must perform reduction reaction with a reducing agent such as sodium borohydride and the like after the reaction using L-proline, and the method described in the Non-patent Literature 2 has a problem that must use a large amount (more than a catalytic amount) of the catalyst of L-proline.

Non-patent Literature 3 (THE NINTH INTERNATIONAL KYOTO CONFERENCE OF NEW ASPECTS OF ORGANIC CHEMISTRY, Program, Abstracts, List of Participants, p 116, (2003)) describes a process for producing an optically active N-protected β-amino acid by reacting trimethylsilyl vinyl ether and an N-(2-hydroxyphenyl)imine with a chiral phosphoric acid derivative.

However, the method described in the Non-patent Literature 3 has a problem that a substrate to be reacted with an imine must be trimethylsilylated into trimethylsilyl vinyl ether.

In addition, Non-patent Literature 4 (The ninth International Kyoto Conference on New Aspects of Organic Chemistry, 2003, Nov., 10-14 (poster presentation was held on November 11$^{th}$) Abstracts, p. 116, No. PA004) discloses a phorphoric acid derivative of the formula (1), but only shows use in a reaction of obtaining α-aminophosphonic acid from an imine and a phosphorous acid diisopropyl ester.

DISCLOSURE OF THE INVENTION

Problems to be Solved by the Invention

The present invention has been accomplished in view of the aforementioned problems, and an object of the present invention is to provide a process for producing amines, particularly, optically active amines useful as an intermediate or the like for medicines, agricultural chemicals or the like in a good yield and a high optical purity without extra after-treatment or the like, and a phosphoric acid derivative, particularly, an optically active phosphoric acid derivative useful for production of the amines or the like.

Means to Solve the Problems

The present inventors have intensively studied in order to solve the aforementioned problems, and, as a result, have found that desired amines are obtained in a good yield and a high optical purity by using a phosphoric acid derivative represented by the formula (1), thereby to complete the present invention.

That is, the present invention is as follows:
1) a process for producing an amine, which comprises reacting an imine compound and a nucleophilic compound (provided that trialkylsilyl vinyl ethers are excluded) in the presence of a phosphoric acid derivative represented by the formula (1):

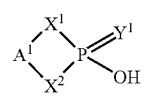

(1)

(wherein $A^1$ represents a spacer; $X^1$ and $X^2$ each independently represent a divalent nonmetal atom or a divalent nonmetal atomic group; and $Y^1$ represents an oxygen atom or a sulfur atom);
2) the process according to the above 1), wherein the phosphoric acid derivative represented by the formula (1) is an optically active phosphoric acid derivative, and the obtained amine is an optically active amine;
3) the process according to the above 1), wherein the imine compound is an imine compound represented by the formula (2):

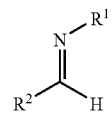

(2)

(wherein $R^1$ represents a hydrogen atom or a protective group, and $R^2$ represents a group having no α-proton or an unsaturated hydrocarbon group);
4) the process according to the above 1), wherein the nucleophilic compound is
a compound represented by the formula (3):

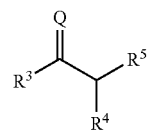

(3)

(wherein $R^3$ represents a hydrogen atom, a hydrocarbon group optionally having substituent(s), a heterocyclic group optionally having substituent(s), an alkoxy group optionally having substituent(s), an aryloxy group optionally having substituent(s), an aralkyloxy group optionally having substituent(s) or a substituted amino group; $R^4$ and $R^5$ each independently represent a hydrogen atom, a hydrocarbon group optionally having substituent(s), a heterocyclic group optionally having substituent(s), $EWG^1$ ($EWG^1$ represents an electron-withdrawing group), an alkoxy group optionally having substituent(s), an aryloxy group optionally having substituent(s), an aralkyloxy group optionally having substituent(s), an alkylthio group optionally having substituent(s), an arylthio group optionally having substituent(s), an aralkylthio group optionally having substituent(s) or a hydroxy group; Q represents a group giving a tautomer of a compound represented by the formula (3); and $R^3$ and $R^4$, $R^3$ and $R^5$, or $R^4$ and $R^5$ may be taken together to form a ring);

a compound represented by the formula (5):

(5)

(wherein $R^7$ represents a hydrogen atom, a hydrocarbon group optionally having substituent(s), a heterocyclic group optionally having substituent(s), an alkoxy group optionally having substituent(s), an aryloxy group optionally having substituent(s) or an aralkyloxy group optionally having substituent(s), an alkylthio group optionally having substituent(s), an arylthio group optionally having substituent(s), an aralkylthio group optionally having substituent (s) or $EWG^2$ ($EWG^2$ represents an electron-withdrawing group), and $Z^1$ represents $N_2$, $P(R^8)_3$ (three of $R^8$, the same or different, represent a hydrogen atom, a hydrocarbon group optionally having substituent(s), a heterocyclic group optionally having substituent(s), an alkoxy group optionally having substituent(s), an aryloxy group optionally having substituent(s) or an aralkyloxy group optionally having substituent(s)) or $CR^9R^{10}$ ($R^9$ and $R^{10}$ each independently represent a hydrogen atom, a hydrocarbon group optionally having substituent (s), a heterocyclic group optionally having substituent(s), an alkoxy group optionally having substituent(s), an aryloxy group optionally having substituent(s), an aralkyloxy group optionally having substituent(s), an alkylthio group optionally having substituent(s), an arylthio group optionally having substituent(s), an aralkylthio group optionally having substituent(s), an amino group or a substituted amino group, provided that either one of $R^9$ and $R^{10}$ represents an alkoxy group optionally having substituent(s), an aryloxy group optionally having substituent(s), an aralkyloxy group optionally having substituent(s), an alkylthio group optionally having substituent(s), an arylthio group optionally having substituent(s), an aralkylthio group optionally having substituent(s), an amino group or a substituted amino group); or a compound represented by the formula (7):

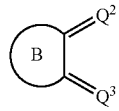

(7)

(wherein ring B represents an aliphatic ring or an aliphatic heterocycle, and $Q^2$ and $Q^3$ each independently represent an oxygen atom, $NR^{17}$ ($R^{17}$ represents a hydrogen atom or a protective group) or a sulfur atom); or a benzene represented by the formula (21):

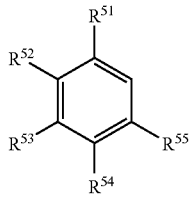

(21)

(wherein $R^{51}$ to $R^{55}$ each independently represent a hydrogen atom or a substituent, provided that $R^{51}$ and $R^{52}$, $R^{52}$ and $R^{53}$, $R^{53}$ and $R^{54}$, or $R^{54}$ and $R^{55}$ may be taken together to form a ring);

5) the process according to the above 1), wherein the obtained amine is an amine represented by formula (4):

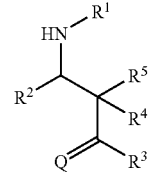

(4)

(wherein $R^1$ to $R^5$ and Q are the same as defined above);

an amine represented by the formula (6):

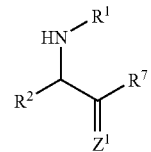

(6)

(wherein $R^1$, $R^2$, $R^7$ and $Z^1$ are the same as defined above); or an amine represented by the formula (8):

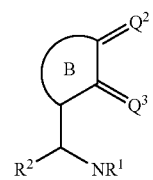

(8)

(wherein $R^1$, $R^2$, $Q^2$ and $Q^3$ are the same as defined above); or a compound represented by the formula (22):

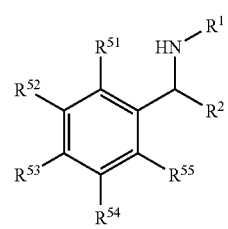

(22)

wherein $R^1$, $R^2$ and $R^{51}$ to $R^{55}$ are the same as defined above;

6) the process according to the above 5), wherein the amine represented by the formula (4), (6), or (8) is an optically active amine;

7) the process according to the above 1), wherein the divalent nonmetal atom or the divalent nonmetal atomic group represented by $X^1$ and $X^2$ in the formula (1) is an oxygen atom, $—NR^{13}—$ ($R^{13}$ represents a hydrogen atom, a hydrocarbon group optionally having substituent(s) or an acyl group optionally having substituent(s)), a sulfur atom or $—CR^{15}R^{16}—$ {$R^{15}$ and $R^{16}$ each independently represent a hydrogen atom, a hydrocarbon group optionally having substituent(s) or $EWG^3$ ($EWG^3$ represents an electron-withdrawing group), provided that either one of $R^{15}$ and $R^{16}$ is $EWG^3$};

8) a phosphoric acid derivative represented by the formula (1a):

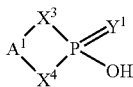
(1a)

(wherein $A^1$ represents a spacer; $X^3$ and $X^4$ each independently represent an oxygen atom, —$NR^{13}$— ($R^{13}$ represents a hydrogen atom, a hydrocarbon group optionally having substituent(s) or an acyl group optionally having substituent(s)), a sulfur atom or —$CR^{15}R^{16}$— {$R^{15}$ and $R^{16}$ each independently represent a hydrogen atom, a hydrocarbon group optionally having substituent(s) or $EWG^3$ ($EWG^3$ represents an electron-withdrawing group), provided that either one of $R^{15}$ and $R^{16}$ is $EWG^3$}; and $Y^1$ represents an oxygen atom or a sulfur atom, provided that when i) $X^3$=$X^4$, then $X^3$ and $X^4$ are each —$NR^{13}$— ($R^{13}$ is a hydrogen atom, a hydrocarbon group optionally having a substituent or an acyl group optionally having substituent(s)), a sulfur atom or —$CR^{15}R^{16}$—, or when $X^3$ and $X^4$ are each —$NR^{13}$—, then the —$NR^{13}$— is —$NR^a$— ($R^a$ represents an acyl group derived from sulfonic acid), or when ii) $X^3$ and $X^4$ are different from each other, then either one of $X^3$ and $X^4$ is —$NR^{13}$—, and the —$NR^{13}$— is —$NR^a$— ($R^a$ represents an acyl group derived from sulfonic acid) and the other is an oxygen atom, —$NR^{13}$— ($R^{13}$ represents a hydrogen atom, a hydrocarbon group optionally having substituent(s) or an acyl group optionally having substituent(s)), a sulfur atom or —$CR^{15}R^{16}$—);

9) the phosphoric acid derivative according to the above 8), wherein the phosphoric acid derivative represented by the formula (1a) is an optically active phosphoric acid derivative;

10) the phosphoric acid derivative represented by the formula (1b):

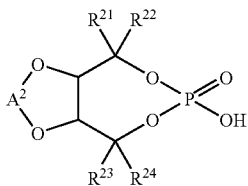
(1b)

(wherein $A^2$ represents a spacer, and $R^{21}$ to $R^{24}$ each independently represent a hydrocarbon group optionally having substituent(s) or a heterocyclic group optionally having substituent(s));

11) the phosphoric acid derivative according to the above 10), wherein the phosphoric acid derivative represented by the formula (1b) is an optically active phosphoric acid derivative;

12) a phosphoric acid derivative represented by the formula (9):

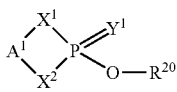
(9)

(wherein $A^1$ represents a spacer; $X^1$ and $X^2$ each independently represent a divalent nonmetal atom or a divalent nonmetal atomic group; $Y^1$ represents an oxygen atom or a sulfur atom; and $R^{20}$ represents an allyl group optionally having substituent(s) or a benzyl group optionally having substituent(s));

13) a phosphoric acid derivative represented by the formula (11):

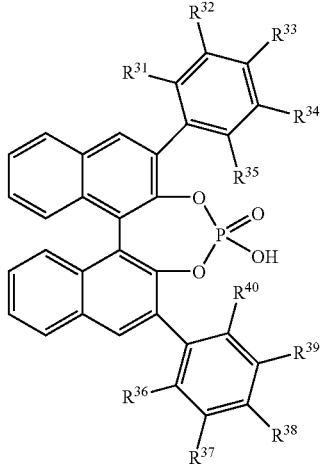
(11)

(wherein $R^{31}$ to $R^{40}$ each independently represent a substituent other than an alkyl-substituted phenyl group, provided that at least one of $R^{31}$ to $R^{35}$ and at least one of $R^{36}$ to $R^{40}$ are an aryl group optionally having substituent(s) (provided that an alkyl-substituted phenyl group is excluded));

14) the phosphoric acid derivative according to the above 11), wherein the phosphoric acid derivative represented by the formula (11) is an optically active phosphoric acid derivative;

15) the process according the above 1), wherein the phosphoric acid derivative represented by the formula (1) is a phosphoric acid derivative represented by the formula (11'):

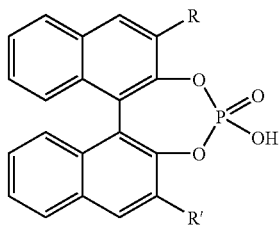
(11')

(wherein R and R', the same or different, represent a hydrogen atom, a bromine atom, an iodine atom, a methoxy group, a triphenylsilyl group, a naphthyl group, a phenyl group or a phenyl group having 1 to 3 substituents (wherein the substituent is a substituent selected from a fluorine atom, a methoxy group, a methyl group, a tert-butyl group, a phenyl group, a trifluoromethyl group, and a naphthyl group));

16) the process according to the above 1), wherein the nucleophilic compound is an unsaturated heterocyclic compound represented by the formula (14):

(14)

(wherein $G^1$ represents S or $NR^{26}$ ($R^{26}$ represents a hydrogen atom or a protective group), and ring E represents a monocyclic heterocycle having at least one double bond), or an unsaturated heterocyclic compound represented by the formula (16):

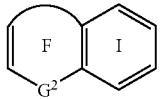
(16)

(wherein $G^2$ represents a heteroatom or a heteroatomic group; ring F represents a heterocycle having at least one double bond; and ring I represents an aromatic ring optionally having substituent(s) or a heterocycle optionally having substituent(s));

and the obtained amine is an amine represented by the formula (15-1):

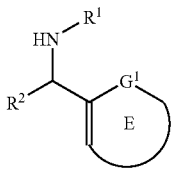
(15-1)

and/or the formula (15-2):

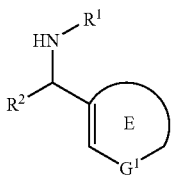
(15-2)

(wherein $R^1$ represents a hydrogen atom or a protective group; $R^2$ represents a group having no α-proton or an unsaturated hydrocarbon group; and ring E and $G^1$ are the same as defined above); or an amine represented by the formula (17):

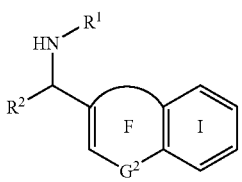
(17)

(wherein $R^1$ represents a hydrogen atom or a protective group; $R^2$ represents a group having no α-proton or an unsaturated hydrocarbon group; and $G^2$, ring F and ring I are the same as defined above);

17) the process according to the above 16), wherein the obtained amine is an optically active amine;

18) a process for producing an amine represented by the formula (13):

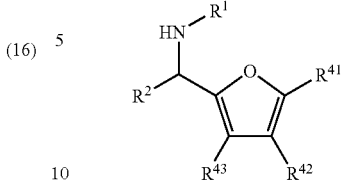
(13)

(wherein $R^1$ represents a hydrogen atom or a protective group; $R^2$ represents a group having no α-proton or an unsaturated hydrocarbon group; and $R^{41}$ to $R^{43}$ each independently represent a hydrogen atom or a substituent), which comprises reacting an imine compound represented by the formula (2):

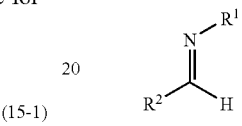
(2)

(wherein $R^1$ represents a hydrogen atom or a protective group, and $R^2$ represents a group having no α-proton or an unsaturated hydrocarbon group), with a furan represented by the formula (12):

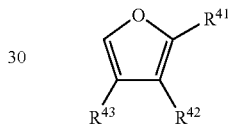
(12)

(wherein $R^{41}$ to $R^{43}$ each independently represent a hydrogen atom or a substituent);

19) the process according to the above 18), wherein the obtained amine is an optically active amine.

20) a phosphoric acid derivative represented by the formula (31):

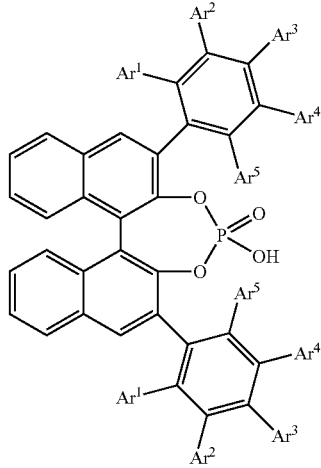
(31)

(wherein $Ar^1$ to $Ar^5$ each independently represent a hydrogen atom or an alkyl-substituted phenyl group, provided that the case where all of $Ar^1$ to $Ar^5$ are a hydrogen atom is excluded);

21) the phosphoric acid derivative according to the above 20), wherein the phosphoric acid derivative represented by the formula (31) is an optically active phosphoric acid derivative;

22) a catalyst for asymmetric synthesis, which comprises the optically active phosphoric acid derivative as defined in the above 9).

EFFECT OF THE INVENTION

The process of the present invention exerts the effect that since the process uses a phosphoric acid derivative represented by the formula (1) having no metal atom in the molecule as a catalyst, any extra post-treatment is not necessary, therefore, workability is considerably improved.

BEST MODE FOR CARRYING OUT THE INVENTION

The imine compound used in the present invention includes, for example, an imine compound represented by the formula (2):

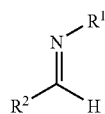

(2)

wherein $R^1$ represents a hydrogen atom or a protective group, and $R^2$ represents a group having no α-proton or an unsaturated hydrocarbon group.

In the formula (2), as a protective group represented by $R^1$, any protective group can be used as far as it is used as an amino protective group, and examples of such protective groups include those described as an amino protective group in "PROTECTIVE GROUPS IN ORGANIC SYNTHESIS THIRD EDITION (JOHN WILEY & SONS, INC. (1999))". Specific examples of the protective group (amino protective group) represented by $R^1$ include a hydrocarbon group optionally having substituent(s), a heterocyclic group optionally having substituent(s), an acyl group optionally having substituent(s), an alkoxycarbonyl group optionally having substituent(s), an aryloxycarbonyl group optionally having substituent (s), an aralkyloxycarbonyl group optionally having substituent (s), an amimosulfonyl group, an alkoxysulfonyl group and the like.

The hydrocarbon group optionally having substituent(s) as a protective group represented by $R^1$ includes a hydrocarbon group and a substituted hydrocarbon group. Examples of the hydrocarbon group include, for example, an alkyl group, an alkenyl group, an alkynyl group, an alkadienyl group, an aryl group, an aralkyl group and the like.

The alkyl group may be straight-chain, branched, or cyclic alkyl group having, for example, 1 to 20 carbon atom(s), and specific examples thereof include methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpentyl, 3-methylpentyl, 4-methylpentyl, 2-methylpentan-3-yl, heptyl, octyl, nonyl, decyl, lauryl, stearyl, cyclopropyl, cyclobutyl, cyclopentyl, cyclohexyl and the like. Inter alia, the alkyl group is preferably an alkyl group having 1 to 15 carbon atom(s), more preferably an alkyl group having 1 to 10 carbon atom(s).

The alkenyl group may be straight-chain or branched alkenyl group having, for example, 2 to 20 carbon atoms, and specific examples thereof include ethenyl, propenyl, 1-butenyl, pentenyl, hexenyl, heptenyl, octenyl, nonenyl, decenyl and the like. Inter alia, the alkenyl group is preferably an alkenyl group having 2 to 15 carbon atoms, more preferably an alkenyl group having 2 to 10 carbon atoms, further more preferably an alkenyl group of having 2 to 6 carbon atoms.

The alkynyl group may be straight-chain or branched alkynyl group having, for example, 2 to 20 carbon atoms, and specific examples thereof include ethynyl, 1-propynyl, 2-propynyl, 1-butynyl, 3-butynyl, pentynyl, hexynyl and the like. Inter alia, the alkynyl group is preferably an alkynyl group having 2 to 15 carbon atoms, more preferably an alkynyl group having 2 to 10 carbon atoms, further more preferably an alkynyl group having 2 to 6 carbon atoms.

The alkadienyl group may be, for example, straight-chain, branched, or cyclic alkadienyl group having 4 or more carbon atoms, preferably 4 to 20 carbon atoms, containing two double bonds in the chain of the aforementioned alkyl group, and specific examples thereof include 1,3-butadienyl, 2,4-butadienyl, 2,3-dimethyl-1,3-butadienyl and the like. Inter alia, the alkadienyl group is more preferably an alkadienyl group having 4 to 15 carbon atoms, further more preferably an alkadienyl group having 4 to 10 carbon atoms.

The aryl group may be, for example, an aryl group having 6 to 20 carbon atoms, and specific examples thereof include phenyl, naphthyl, anthryl, biphenyl and the like. Inter alia, the aryl group is preferably an aryl group having 6 to 15 carbon atoms.

The aralkyl group includes, for example, a group in which at least one hydrogen atom of the aforementioned alkyl group is substituted with the aryl group, for example, an aralkyl group having 7 to 20 carbon atoms, and specific examples thereof include benzyl, 2-phenylethyl, 1-phenylpropyl, 3-naphthylpropyl and the like. Inter alia, the aralkyl group is preferably an aralkyl group having 6 to 15 carbon atoms.

The substituted hydrocarbon group (hydrocarbon group having substituent(s)) includes a hydrocarbon group in which at least one hydrogen atom of the aforementioned hydrocarbon group is substituted with a substituent. Examples of the substituted hydrocarbon group include a substituted alkyl group, a substituted alkenyl group, a substituted alkynyl group, a substituted alkadienyl group, a substituted aryl group, a substituted aralkyl group and the like. The substituent will be described later.

The heterocyclic group optionally having substituent(s) as a protective group represented by $R^1$ includes a heterocyclic group and a substituted heterocyclic group. Examples of the heterocyclic group include an aliphatic heterocyclic group and an aromatic heterocyclic group.

The aliphatic heterocyclic group includes, for example, a 5 to 8-membered, preferably 5- or 6-membered monocyclic aliphatic heterocyclic group, and a polycyclic or fused aliphatic heterocyclic group, having 2 to 20 carbon atoms, which contains at least one, preferably 1 to 3 heteroatom(s) such as a nitrogen atom, an oxygen atom and/or a sulfur atom as a heteroatom. Specific examples of the aliphatic heterocyclic group include a pyrrolidyl-2-one group, a piperidino group, a piperazinyl group, a morpholino group, a morpholinyl group, a tetrahydrofuryl group, a tetrahydropyranyl group, a tetrahydrofuranyl group and the like. Inter alia, the aliphatic heterocyclic group is preferably an aliphatic heterocyclic group having 2 to 14 carbon atoms.

The aromatic heterocyclic group includes, for example, a 5- to 8-membered, preferably 5- or 6-membered monocyclic heteroaryl group, or a polycyclic or fused cyclic heteroaryl group, having 2 to 20 carbon atoms, which contains at least one, preferably 1 to 3 heteroatoms such as a nitrogen atom, an oxygen atom and/or a sulfur atom as a heteroatom, and specific examples thereof include furyl, thienyl, pyridyl, pyrimidinyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzoimidazolyl, benzooxazolyl, benzothiazolyl, acridyl, acridinyl, and the like. Inter alia, the aromatic heterocyclic group is preferably an aromatic heterocyclic group having 2 to 15 carbon atoms.

The substituted heterocyclic group (heterocyclic group having substituent(s)) includes a heterocyclic group in which at least one hydrogen atom of the aforementioned heterocyclic group is substituted with a substituent. Examples of the substituted heterocyclic group (heterocyclic group having substituent(s)) include a substituted aliphatic heterocyclic group and a substituted aromatic heterocyclic group. The substituents will be described later.

The acyl group optionally having substituent(s) as a protective group represented by $R^1$ includes an acyl group and a substituted acyl group. Examples of the acyl group include, for example, an acyl group having 1 to 20 carbon atom(s) derived from an acid such as carboxylic acids, sulfonic acids, sulfinic acids, phosphinic acids, phosphonic acids and the like, which may be straight-chain, branched, or cyclic.

The acyl group derived from carboxylic acid includes an acyl group derived from carboxylic acids such as aliphatic carboxylic acids, aromatic carboxylic acids and the like, and is represented by, for example, —$COR^c$ (wherein $R^c$ represents a hydrogen atom, a hydrocarbon group optionally having substituent(s) or a heterocyclic group optionally having substituent(s) (the hydrocarbon group optionally having substituent(s) and the heterocyclic group optionally having substituent(s) may be the same as respective groups explained as a protective group of $R^1$ in the aforementioned formula (2))). Specific examples of the acyl group derived from carboxylic acids include formyl, acetyl, propionyl, butyryl, pivaloyl, pentanoyl, hexanoyl, lauroyl, stearoyl, benzoyl, 1-naphthoyl, 2-naphthoyl and the like. Inter alia, the acyl group is preferably an acyl group having 2 to 18 carbon atoms.

The acyl group derived from sulfonic acids includes a sulfonyl group. The sulfonyl group include a substituted sulfonyl group represented by, for example, $R^d$—$SO_2$— ($R^d$ represents a hydrocarbon group optionally having substituent(s) or a heterocyclic group optionally having substituent(s) (the hydrocarbon group optionally having substituent(s) and the heterocyclic group optionally having substituent(s) may be the same as respective groups explained as a protective group of $R^1$ in the above-mentioned formula (2))). Specific examples of the sulfonyl group include methanesulfonyl, trifluoromethanesulfonyl, phenylsulfonyl, p-toluenesulfonyl and the like.

The acyl group derived from sulfinic acids includes a sulfinyl group. The sulfinyl group includes a substituted sulfinyl group represented by, for example, $R^e$—SO— ($R^e$ represents a hydrocarbon group optionally having substituent(s), a heterocyclic group optionally having substituent(s) or a substituted amino group (the hydrocarbon group optionally having substituent(s) and the heterocyclic group optionally having substituent(s) may be the same as respective groups explained as a protective group of $R^1$ in the above-mentioned formula (2), and the substituted amino group may be the same as each group explained in the substituent in the hydrocarbon group optionally having substituent(s) explained as a protective group of $R^1$ in the above-mentioned formula (2))). Specific examples of the sulfinyl group include methanesulfinyl, benzenesulfinyl, and the like.

The acyl group derived from phosphinic acids includes a phosphinyl group. The phosphinyl group includes a substituted phosphinyl group represented by, for example, ($R^f$)$_2$—PO— (two of $R^f$, the same or different, represent a hydrocarbon group optionally having substituent(s) (the hydrocarbon group optionally having substituent(s) may be the same as the hydrocarbon group optionally having substituent (s) explained as a protective group in $R^1$ in the above-mentioned formula (2))). Specific examples of the phosphinyl group include dimethylphosphinyl, diphenylphosphinyl and the like.

The acyl group derived from phosphonic acids includes a phosphonyl group. Examples of the phosphonyl group include a substituted phosphonyl group represented by, for example, ($R^gO$)$_2$—PO— (two of $R^9$, the same or different, represent a hydrocarbon group optionally having substituent(s) (the hydrocarbon group optionally having substituent(s) may be the same as the hydrocarbon group optionally having substituent(s) explained as a protective group of $R^1$ in the above-mentioned formula (2))). Specific examples of the phosphonyl group include dimethylphosphonyl, diphenylphosphonyl and the like.

The substituted acyl group (acyl group having substituent(s)) includes an acyl group in which at least one hydrogen atom of the aforementioned acyl group is substituted with a substituent. The substituents will be described later.

The alkoxycarbonyl group optionally having substituent(s) as a protective group represented by $R^1$ includes an alkoxycarbonyl group and a substituted alkoxycarbonyl group. The alkoxycarbonyl group includes, for example, an alkoxycarbonyl group having 2 to 20 carbon atoms which may be straight-chain, branched, or cyclic, and specific examples thereof include methoxycarbonyl, ethoxycarbonyl, n-propoxycarbonyl, 2-propoxycarbonyl, n-butoxycarbonyl, tert-butyloxycarbonyl, pentyloxycarbonyl, hexyloxycarbonyl, 2-ethylhexyloxycarbonyl, lauryloxycarbonyl, stearyloxycarbonyl, cyclohexyloxycarbonyl and the like.

The substituted alkoxycarbonyl group (alkoxycarbonyl group having a substitutent) includes an alkoxycarbonyl group in which at least one hydrogen atom of the aforementioned alkoxycarbonyl group is substituted with a substituent. The substituents will be described later. Specific examples of the substituted alkoxycarbonyl group include 2,2,2-trichloroethoxycarbonyl, 1,1-dimethyl-2,2,2-trichloroethoxycarbonyl and the like.

The aryloxycarbonyl group optionally having substituent (s) as a protective group represented by $R^1$ includes an aryloxycarbonyl group and a substituted aryloxycarbonyl group. The aryloxycarbonyl group includes, for example, an aryloxycarbonyl group having 7 to 20 carbon atoms, and specific examples thereof include phenoxycarbonyl, naphthyloxycarbonyl and the like.

The substituted aryloxycarbonyl group (aryloxycarbonyl group having substituent (s)) includes an aryloxycarbonyl group in which at least one hydrogen atom of the aforementioned aryloxycarbonyl group is substituted with a substituent. The substituents will be described later.

The aralkyloxycarbonyl group optionally having substituent(s) as a protective group represented by $R^1$ includes an aralkyloxycarbonyl group and a substituted aralkyloxycarbonyl group. The aralkyloxycarbonyl group includes, for example, an aralkyloxycarbonyl group having 8 to 20 carbon atoms, and specific examples thereof include benzyloxycarbonyl, phenylethoxycarbonyl, 9-fluorenylmethyloxycarbonyl and the like.

The substituted aralkyloxycarbonyl group (aralkyloxycarbonyl group having substituent(s)) includes an aralkyloxycarbonyl group in which at least one hydrogen atom of the aforementioned aralkyloxycarbonyl group is substituted with a substituent. The substituents will be described later. Specific examples of the substituted aralkyloxycarbonyl group include 4-nitrobenzyloxycarbonyl, 4-methoxybenzyloxycarbonyl, 4-methylbenzyloxycarbonyl, 3,4-dimethoxybenzyloxycarbonyl and the like.

The aminosulfonyl group as a protective group represented by $R^1$ includes an aminosulfonyl group represented by, for example, $R^i$—$SO_2$— ($R^i$ represents an amino group or a substituted amino group). The substituted amino group represented by $R^i$ may be the same as a substituted amino group as a substituent described later. Specific examples of the aminosulfonyl group include aminosulfonyl, dimethylaminosulfonyl, diethylaminosulfonyl, diphenylaminosulfonyl and the like.

The alkoxysulfonyl group as a protective group represented by $R^1$ includes an alkoxysulfonyl group represented by, for example, $R^j$—$SO_2$— ($R^j$ represents an alkoxy group optionally having substituent(s), an arylxoxy group optionally having substituent(s) or an aralkyloxy group optionally having substituent(s)). The alkoxy group optionally having substituent(s), the aryloxy group optionally having substituent(s) and the aralkyloxy group optionally having substituent(s) represented by $R^j$ may be the same as an alkoxy group optionally having substituent(s), an aryloxy group optionally having substituent(s) and an aralkyloxy group optionally having substituent(s) as a substituent described later. Specific examples of the alkoxysulfonyl group include methoxysulfonyl, ethoxysulfonyl, phenoxysulfonyl, benzyloxysulfonyl and the like.

The substituent includes, for example, a hydrocarbon group optionally having substituent (s), a halogen atom, a halogenated hydrocarbon group, a heterocyclic group optionally having substituent (s), an alkoxy group optionally having a substituent, an aryloxy group optionally having substituent(s), an aralkyoxy group optionally having substituent(s), a heteroaryloxy group optionally having substituent(s), an alkylthio group optionally having substituent(s), an arylthio group optionally having substituent(s), an aralkylthio group optionally having substituent(s), a heteroarylthio group optionally having substituent (s), an acyl group optionally having substituent (s), an acyloxy group optionally having substituent(s), an alkoxycarbonyl group optionally having substituent(s), an aryloxycarbonyl group optionally having substituent(s), an aralkyloxycarbonyl group optionally having substituent (s), an alkylenedioxy group optionally having substituent(s), a nitro group, an amino group, a substituted amino group, a cyano group, a sulfo group, a substituted silyl group, a hydroxy group, a carboxy group, an alkoxythiocarbonyl group optionally having substituent(s), an aryloxythiocarbonyl group optionally having substituent(s), an aralkyloxythiocarbonyl group optionally having substituent(s), an alkylthiocarbonyl group optionally having substituent(s), an arylthiocarbonyl group optionally having substituent(s), an aralkylthiocarbonyl group optionally having substituent(s), a carbamoyl group optionally having a substituent, a substituted phosphino group, an aminosulfonyl group, an alkoxysulfonyl group and the like.

The hydrocarbon group optionally having substituent(s), the heterocyclic group optionally having substituent(s), the acyl group optionally having substituent(s), the alkoxycarbonyl group optionally having substituent(s), the aryloxycarbonyl group optionally having substituent(s), the aralkyloxycarbonyl group optionally having substituent(s), the aminosulfonyl group and the alkoxysulfonyl group, as a substituent, may be the same as respective groups explained in the aforementioned protective group.

The halogen atom as a substituent includes a fluorine atom, a chlorine atom, a bromine atom, an iodine atom and the like.

The halogenated hydrocarbon group as a substituent includes a group in which at least one hydrogen atom of the aforementioned hydrocarbon group is halogenated (e.g. fluorinated, chlorinated, brominated, iodinated etc.). The halogenated hydrocarbon includes, for example, a halogenated alkyl group, a halogenated aryl group, a halogenated aralkyl group and the like.

The halogenated alkyl group includes, for example, a halogenated alkyl group having 1 to 20 carbon atom(s), and specific examples thereof include chloromethyl, bromomethyl, 2-chloroethyl, 3-bromopropyl, fluoromethyl, fluoroethyl, fluoropropyl, fluorobutyl, fluoropentyl, fluorohexyl, fluoroheptyl, fluorooctyl, fluorononyl, fluorodecyl, difluoromethyl, difluoroethyl, fluorocyclohexyl, trifluoromethyl, 2,2,2-trifluoroethyl, 3,3,3-trifluoropropyl, pentafluoroethyl, 3,3,4,4,4-pentafluorobutyl, perfluoro-n-propyl, perfluoroisopropyl, perfluoro-n-butyl, perfluoroisobutyl, perfluoro-tert-butyl, perfluoro-sec-butyl, perfluoropentyl, perfluoroisopentyl, perfluoro-tert-pentyl, perfluoro-n-hexyl, perfluoroisohexyl, perfluoroheptyl, perfluorooctyl, perfluorononyl, perfluorodecyl, 2-perfluorooctylethyl, perfluorocyclopropyl, perfluorocyclopentyl, perfluorocyclohexyl and the like. Inter alia, the halogenated alkyl group is preferably a halogenated alkyl group having 1 to 10 carbon atom(s).

The halogenated aryl group includes, for example, an aryl group having 6 to 20 carbon atoms, and specific examples thereof include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trifluoromethylphenyl, 3-trifluoromethylphenyl, 4-trifluoromethylphenyl, 2-trichloromethylphenyl, 3-trichloromethylphenyl, 4-trichloromethylphenyl, perfluorophenyl, perfluorophenyl, perfluoronaphthyl, perfluoroanthryl, perfluorobiphenyl and the like. Inter alia, the aryl group is preferably a halogenated aryl group having 6 to 15 carbon atoms.

The halogenated aralkyl group includes, for example, a group in which at least one hydrogen atom of the aforementioned aralkyl group is substituted with the halogen atom, for example, a halogenated aralkyl group having 7 to 20 carbon atoms, and specific examples thereof include 2-fluorobenzyl, 3-fluorobenzyl, 4-fluorobenzyl, 2-chlorobenzyl, 3-chlorobenzyl, 4-chlorobenzyl, 4-bromobenzyl, 4-iodobenzyl, 2-trifluoromethylbenzyl, 3-trifluoromethylbenzyl, 4-trifluoromethylbenzyl, 4-trichloromethylbenzyl, perfluorobenzyl and the like. Inter alia, the halogenated aralkyl group is preferably a halogenated aralkyl group having 6 to 15 carbon atoms.

The alkoxy group optionally having substituent(s) as a substituent includes an alkoxy group and a substituted alkoxy group. The alkoxy group includes, for example, an alkoxy group having 1 to 20 carbon atom(s), which may be straight-chain, branched, or cyclic, and specific examples thereof include methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, heptyloxy, octyloxy, nonyloxy, decyloxy, cyclohexyloxy and the like. Inter alia, the alkoxy group is preferably an alkoxy group having 1 to 10 carbon atom(s), more preferably an alkoxy group having 1 to 6 carbon atom(s).

The substituted alkoxy group (alkoxy group having substituent(s)) includes an alkoxy group in which at least one hydrogen atom of the aforementioned alkoxy group is substituted with the aforementioned substituent.

The aryloxy group optionally having substituent(s) as a substituent includes an aryloxy group and a substituted aryloxy group. The aryloxy group includes, for example, an aryloxy group having 6 to 20 carbon atoms, and specific examples thereof include phenyloxy, naphthyloxy, anthryloxy and the like. Inter alia, the aryloxy group is preferably an aryloxy group having 6 to 14 carbon atoms.

The substituted aryloxy group (aryloxy group having substituent(s)) includes an aryloxy group in which at least one hydrogen atom of the aforementioned aryloxy group is substituted with the substituent.

The aralkyloxy group optionally having substituent(s) as a substituent includes an aralkyloxy group and a substituted aralkyloxy group. The aralkyloxy group includes, for example, an aralkyloxy group having 7 to 20 carbon atoms, and specific examples thereof include benzyloxy, 1-phenylethoxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyoxy and the like. Inter alia, the aralkyloxy group is preferably an aralkyloxy group having 7 to 12 carbon atoms.

The substituted aralkyloxy group (aralkyloxy group having substituent(s)) includes an aralkyloxy group in which at least one hydrogen atom of the aforementioned aralkyloxy group is substituted with the aforementioned substituent.

The heteroaryloxy group optionally having substituent(s) as a substituent includes a heteroaryloxy group and a substituted heteroaryloxy group. The heteroaryloxy group includes, for example, a heteroaryloxy group having 2 to 20 carbon atoms, preferably 2 to 15 carbon atoms containing at least one, preferably 1 to 3 heteroatom(s) such as a nitrogen atom, an oxygen atom, a sulfur atom and the like as a heteroatom, and specific examples thereof include 2-pyridyloxy, 2-pyrazyloxy, 2-pyrimidyloxy, 2-quinolyloxy and the like.

The substituted heteroaryloxy group (heteroaryloxy group having substituent (s)) includes a heteroaryloxy group in which at least one hydrogen atom of the aralkyloxy group is substituted with the aforementioned substituent.

The alkylthio group optionally having substituent(s) as a substituent includes an alkylthio group and a substituted alkylthio group. The alkylthio group includes, for example, an alkylthio group, which may be straight-chain, branched, or cyclic, having 1 to 20 carbon atom(s), and specific examples thereof include methylthio, ethylthio, n-propylthio, 2-propylthio, n-butylthio, 2-butylthio, isobutylthio, tert-butylthio, pentylthio, hexylthio, cyclohexylthio and the like. Inter alia, the alkylthio group is preferably an alkylthio group having 1 to 10 carbon atom(s), more preferably an alkylthio group having 1 to 6 carbon atom(s).

The substituted alkylthio group (alkylthio group having substituent(s)) includes an alkylthio group in which at least one hydrogen atom of the aforementioned alkylthio group is substituted with the aforementioned substituent.

The arylthio group optionally having substituent(s) as a substituent includes an arylthio group and a substituted arylthio group. The arylthio group includes, for example, an arylthio group having 6 to 20 carbon atoms, and specific examples thereof include phenylthio, naphthylthio and the like. Inter alia, the arylthio group is preferably an arylthio group having 6 to 14 carbon atoms.

The substituted arylthio group (arylthio group having substituent(s)) includes an arylthio group in which at least one hydrogen atom of the aforementioned arylthio group is substituted with the aforementioned substituent.

The aralkylthio group optionally having substituent(s) as a substituent includes an aralkylthio group and a substituted aralkylthio group. The aralkylthio group includes, for example, an aralkylthio group having 7 to 20 carbon atoms, and specific examples thereof include benzylthio, 2-phenethylthio and the like. Inter alia, the aralkylthio group is preferably an aralkylthio group having 7 to 12 carbon atoms.

The substituted aralkylthio group (aralkylthio group having substituent(s)) includes an aralkylthio group in which at least one hydrogen atom of the aforementioned aralkylthio group is substituted with the aforementioned substituent.

The heteroarylthio group optionally having substituent (s) as a substituent includes a heteroarylthio group and a substituted heteroarylthio group. The heteroarylthio group includes, for example, a heteroarylthio group having 2 to 20 carbon atoms, preferably 2 to 15 carbon atoms, containing at least one, preferably 1 to 3 heteroatom(s) such as a nitrogen atom, an oxygen atom, a sulfur atom and the like as a heteroatom, and specific examples thereof include 4-pyridylthio, 2-benzimidazolylthio, 2-benzoxazolylthio, 2-benzthiazolylthio and the like.

The substituted heteroarylthio group (heteroarylthio group having substituent(s)) includes a heteroarylthio group in which at least one hydrogen atom of the aforementioned heteroarylthio group is substituted with the aforementioned substituent.

The acyloxy group optionally having substituent(s) as a substituent includes an acyloxy group and a substituted acyloxy group. The acyloxy group includes, for example, an acyloxy group having 2 to 20 carbon atoms derived from carboxylic acids such as aliphatic carboxylic acids, aromatic carboxylic acids and the like, and specific examples thereof include acetoxy, propionyloxy, butyryloxy, pivaloyloxy, pentanoyloxy, hexanoyloxy, lauroyloxy, stearoyloxy, benzoyloxy and the like. Inter alia, the acyloxy group is preferably an acyloxy group having 2 to 18 carbon atoms.

Examples of the substituted acyloxy group (acyloxy group having substituent(s)) include an acyloxy group in which at least one hydrogen atom of the aforementioned acyloxy group is substituted with the aforementioned substituent.

Examples of the substituted amino group as a substituent include an amino group in which one or two hydrogen atoms of the amino group are substituted with a substituent such as a protective group and the like. As a protective group, any protective group can be used as far as it is used as an amino protective group, and specific examples thereof include those described as an amino protective group in "PROTECTIVE GROUPS IN ORGANIC SYNTHESIS THIRD EDITION (JOHN WILEY & SONS, INC. (1999))". Specific examples of the amino protective group include a hydrocarbon group optionally having substituent(s), an acyl group optionally having substituent(s), an alkoxycarbonyl group optionally having substituent(s), an aryloxycarbonyl group optionally having substituent(s), an aralkyloxycarbonyl group optionally having substituent (s) and the like. The hydrocarbon group optionally having substituent(s), the acyl group optionally having substituent(s), the alkoxycarbonyl group optionally having substituent(s), the aryloxycarbonyl group optionally having substituent(s) and the aralkyloxycarbonyl group optionally having substituent(s) may be the same as those explained in the aforementioned protective group.

Specific examples of the amino group substituted with the alkyl group, that is, an alkyl-substituted amino group include a mono- or di-alkylamino group such as N-methylamino, N,N-dimethylamino, N,N-diethylamino, N,N-diisopropylamino, N-methyl-N-(2-propyl)amino, N-cyclohexylamino and the like.

Specific examples of the amino group substituted with the aryl group, that is, an aryl-substituted amino group include a mono- or di-arylamino group such as N-phenylamino, N,N-diphenylamino, N-naphthylamino, N-naphthyl-N-phenylamino and the like.

Specific examples of the amino group substituted with the aralkyl group, that is, an aralkyl-substituted amino group include a mono- or di-aralkylamino group such as N-benzylamino, N,N-dibenzylamino and the like.

In addition, the substituted amino group includes a di-substituted amino group such as N-methyl-N-phenylamino, N-benzyl-N-methylamino and the like.

Specific examples of the amino group substituted with the acyl group, that is, an acylamino group include formylamino, acetylamino, propionylamino, pivaloylamino, pentanoylamino, hexanoylamino, benzoylamino, —$NHSO_2CH_3$, —$NHSO_2C_6H_5$, —$NHSO_2C_6H_4CH_3$, —$NHSO_2CF_3$, —$NHSO_2N(CH_3)_2$ and the like.

Specific examples of the amino group substituted with the alkoxycarbonyl group, that is, an alkoxycarbonylamino group include methoxycarbonylamino, ethoxycarbonylamino, n-propoxycarbonylamino, n-butoxycarbonylamino, tert-butoxycarbonylamino, pentyloxycarbonylamino, hexyloxycarbonylamino and the like.

The amino group substituted with an aryloxycarbonyl group, that is, an aryloxycarbonylamino group includes, for example, an amino group in which one hydrogen atom of the amino group is substituted with the aforementioned aryloxycarbonyl group, and specific examples thereof include phenoxycarbonylamino, naphthyloxycarbonylamino and the like.

Specific examples of the amino group substituted with the aralkyloxycarbonyl group, that is, an aralkyloxycarbonylamino group include benzyloxycarbonylamino and the like.

The alkylenedioxy group optionally having substituent(s) as a substituent includes, for example, such that the adjacent two hydrogen atoms of an aromatic ring in the aforementioned aryl or aralkyl group are substituted with an alkylenedioxy group optionally having a substitutent. The alkylenedioxy group optionally having substituent(s) includes an alkylenedioxy group and a substituted alkylenedioxy group. The alkylenedioxy group includes, for example, an alkylenedioxy group having 1 to 3 carbon atom(s), and specific examples thereof include methylenedioxy, ethylenedioxy, trimethylenedioxy, propylenedioxy and the like.

The substituted silyl group as a substituent includes, for example, a tri-substituted silyl group in which three hydrogen atoms of a silyl group are substituted with a substituent such as an alkyl group, a substituted alkyl group, an aryl group, a substituted aryl group, an aralkyl group, a substituted aralkyl group, an alkoxy group, a substituted alkoxy group and the like. The alkyl group, the substituted alkyl group, the aryl group, the substituted aryl group, the aralkyl group, the substituted aralkyl group, the alkoxy group, and the substituted alkoxy group may be the same as respective groups explained above. Specific examples of the substituted silyl group include trimethylsilyl, triethylsilyl, tri(2-propyl)silyl, tert-butyldimethylsilyl, tert-butyldiphenylsilyl, triphenylsilyl, tert-butylmethoxyphenylsilyl, tert-butoxydiphenylsilyl and the like.

The alkoxythiocarbonyl group optionally having substituent(s) as a substituent includes an alkoxythiocarbonyl group and a substituted alkoxythiocarbonyl group. The alkoxythiocarbonyl group includes, for example, an alkoxythiocarbonyl group having 2 to 20 carbon atoms, which may be straight-chain, branched, or cyclic, and specific examples thereof include methoxythiocarbonyl, ethoxythiocarbonyl, n-propoxythiocarbonyl, 2-propoxythiocarbonyl, n-butoxythiocarbonyl, tert-butoxythiocarbonyl, pentyloxythiocarbonyl, hexyloxythiocarbonyl, 2-ethylhexyloxythiocarbonyl, lauryloxythiocarbonyl, stearyloxythiocarbonyl, cyclohexyloxythiocarbonyl and the like.

The substituted alkoxythiocarbonyl group (alkoxythiocarbonyl group having substituent(s)) includes an alkoxythiocarbonyl group in which at least one hydrogen atom of the aforementioned alkoxythiocarbonyl group is substituted with the aforementioned substituent.

The aryloxythiocarbonyl group optionally having substituent(s) as a substituent includes an aryloxythiocarbonyl group and a substituted aryloxythiocarbonyl group. The aryloxythiocarbonyl group includes, for example, an aryloxythiocarbonyl group having 7 to 20 carbon atoms, and specific examples thereof include phenoxythiocarbonyl, naphthyloxythiocarbonyl and the like.

The substituted aryloxythiocarbonyl group (aryloxythiocarbonyl group having substituent(s)) includes an aryloxythiocarbonyl group in which at least one hydrogen atom of the aryloxythiocarbonyl group is substituted with the aforementioned substituent.

The aralkyloxythiocarbonyl group optionally having substituent(s) as a substituent includes an aralkyloxythiocarbonyl group and a substituted aralkyloxythiocarbonyl group. The aralkyloxythiocarbonyl group includes, for example, an aralkyloxythiocarbonyl group having 8 to 20 carbon atoms, and specific examples thereof include benzyloxythiocarbonyl, phenethyloxythiocarbonyl, 9-fluorenylmethyloxythiocarbonyl and the like.

The substituted aralkyloxythiocarbonyl group (aralkyloxythiocarbonyl group having substituent (s)) includes an aralkyloxythiocarbonyl group in which at least one hydrogen atom of the aforementioned aralkyloxythiocarbonyl group is substituted with the aforementioned substituent.

The alkylthiocarbonyl group optionally having substituent(s) as a substituent includes an alkylthiocarbonyl group and a substituted alkylthiocarbonyl group. The alkylthiocarbonyl group includes, for example, an alkylthiocarbonyl group having 2 to 20 carbon atoms, which may be straight-chain, branched, or cyclic, and specific examples thereof include methylthiocarbonyl, ethylthiocarbonyl, n-propylthiocarbonyl, 2-propylthiocarbonyl, n-butylthiocarbonyl, tert-butylthiocarbonyl, pentylthiocarbonyl, hexylthiocarbonyl, 2-ethylhexylthiocarbonyl, laurylthiocarbonyl, stearylthiocarbonyl, cyclohexylthiocarbonyl and the like.

The substituted alkylthiocarbonyl group (alkylthiocarbonyl group having substituent(s)) includes an alkylthiocarbonyl group in which at least one hydrogen atom of the alkylthiocarbonyl group is substituted with the aforementioned substituent.

The arylthiocarbonyl group optionally having substituent(s) as a substituent includes an arylthiocarbonyl group and a substituted arylthiocarbonyl group. The arylthiocarbonyl group includes, for example, an arylthiocarbonyl group having 7 to 20 carbon atoms, and specific examples thereof include phenylthiocarbonyl, naphthylthiocarbonyl and the like.

The substituted arylthiocarbonyl group (arylthiocarbonyl group having substituent(s)) includes an arylthiocarbonyl group in which at least one hydrogen atom of the arylthiocarbonyl group is substituted with the aforementioned substituent.

The aralkylthiocarbonyl group optionally having substituent(s) as a substituent includes an aralkylthiocarbonyl group and a substituted aralkylthiocarbonyl group. The aralkylthiocarbonyl group includes, for example, an aralkylthiocarbonyl group having 8 to 20 carbon atoms, and specific examples thereof include benzylthiocarbonyl, phenethylthiocarbonyl, 9-fluorenylmethylthiocarbonyl and the like.

The substituted aralkylthiocarbonyl group (aralkylthiocarbonyl group having substituent(s)) includes an aralkylthiocarbonyl group in which at least one hydrogen atom of the aforementioned aralkylthiocarbonyl group is substituted with the aforementioned substituent.

The carbamoyl group optionally having substituent(s) as a substituent includes a carbamoyl group and a substituted carbamoyl group. The substituted carbamoyl group includes the carbamoyl group in which one or two hydrogen atoms of an amino group in the carbamoyl group are substituted with a substituent such as a hydrocarbon group optionally having substituent(s) and the like. The hydrocarbon group optionally having substituent(s) may be the same as the hydrocarbon group optionally having substituent(s) explained as a protective group of $R^1$ in the formula (2). Specific examples of the substituted carbamoyl group include N-methylcarbamoyl, N,N-diethylcarbamoyl, N-phenylcarbamoyl and the like.

The substituted phosphino group as a substituent includes a phosphino group in which one or two hydrogen atoms of the phosphino group are substituted with a substituent such as a hydrocarbon group optionally having substituent (s) and the like. The hydrocarbon group optionally having substituent(s) may be the same as the hydrocarbon group optionally having substituent(s) explained as a protective group of $R^1$ in the formula (2). Specific examples of the substituted phosphino group include dimethylphosphino, diethylphosphino, diphenylphosphino, methylphenylphosphino and the like.

Inter alia, the protective group represented by $R^1$ is preferably the acyl group optionally having substituent (s), the alkoxycarbonyl group optionally having substituent(s), the aryloxycarbonyl group optionally having substituent(s), and the aralkyloxycarbonyl group optionally having substituent(s).

As a group having no α-proton represented by $R^2$, a group which does not isomerize an imine compound represented by the above-mentioned formula (2) is preferable. The group having no α-proton include, for example, a tertiary alkyl group optionally having substituent(s), an aryl group optionally having substituent (s), a heterocyclic group optionally having substituent(s) and an acyl group optionally having substituent(s).

The tertiary alkyl group optionally having substituent(s) includes a tertiary alkyl group and a substituted tertiary alkyl group.

The tertiary alkyl group includes, for example, a tertiary alkyl group having 4 to 20 carbon atoms, and specific examples thereof include tert-butyl, tert-pentyl, tert-hexyl and the like.

The substituted tertiary alkyl group (tertiary alkyl group having substituent(s)) includes a tertiary alkyl group in which at least one hydrogen atom of the tertiary alkyl group is substituted with a substituent. The substituent may be the same as the substituent explained in the protective group of $R^1$. As the substituted tertiary alkyl group, for example, a substituted tertiary alkyl group which is substituted with the aryl group includes, for example, an aralkyl group having 9 to 20 carbon atoms, and specific examples thereof include α,α-dimethylbenzyl and the like. Inter alia, said aralkyl group is preferably an aralkyl group having 9 to 15 carbon atoms.

The aryl group optionally having substituent(s) may be the same as the aryl group optionally having substituent(s) explained in the hydrocarbon group optionally having substituent(s) in the protective group in $R^1$. In addition, the heterocyclic group optionally having substituent(s) and the acyl group optionally having substituent(s) may be the same as respective groups explained in the protective group of $R^1$.

The acyl group optionally having substituent(s) in the group having no α-proton includes, for example, an acyl optionally having substituent(s) explained in the protective group of $R^1$ and the like, and includes a group represented by, for example, $R^b CO$— ($R^b$ represents a hydrocarbon group optionally having substituent (s), a heterocyclic group optionally having substituent(s), an alkoxy group optionally having substituent(s), an aryloxy group optionally having substituent(s), an aralkyloxy group optionally having substituent(s), a heteroaryloxy group optionally having substituent(s), an alkylthio group optionally having substituent(s), an arylthio group optionally having substituent(s), an aralkylthio group optionally having substituent(s), a heteroarylthio group optionally having substituent (s) or a substituted amino group). The hydrocarbon group optionally having a substitutent and the heterocyclic group optionally having substituent(s) represented by $R^b$ may be the same as the hydrocarbon group optionally having substituent(s) and the heterocyclic group optionally having substituent(s) explained in the protective group of $R^1$. In addition, the alkoxy group optionally having substituent(s), the aryloxy group optionally having substituent(s), the aralkyloxy group optionally having substituent(s), the heteroaryloxy group optionally having substituent(s), the alkylthio group optionally having substituent (s), the arylthio group optionally having substituent(s), the aralkylthio group optionally having substituent(s), the heteroarylthio group optionally having substituent(s) and the substituted amino group may be the same as respective groups explained in the substituent of the hydrocarbon group optionally having substituent(s) in the protective group of $R^1$.

Examples of the unsaturated hydrocarbon group represented by $R^2$ include an alkenyl group optionally having substituent(s), an alkynyl group optionally having substituent(s) and an alkadienyl group optionally having substituent(s). The alkenyl group optionally having substituent(s), the alkynyl group optionally having substituent (s) and the alkadienyl group optionally having substituent(s) may be the same as respective groups explained in the hydrocarbon group optionally having substituent(s) in a protective group in $R^1$.

Specific examples of the imine compound represented by the above-mentioned formula (2) used in the present invention include, for example, the following compounds:

Exemplified Compound 2-1:

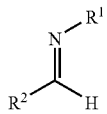

$R^1$: Ac, Bz, Boc, Z, Fmoc, Troc, etc.
$R^2$: Ph, 4-Me—Ph, 4-Cl—Ph,
   Nap, Py, t-Bu, —CH=CH—CH$_2$,
   1-Propynyl, Ac, —COOMe, —COOEt,
   —COOBn, etc.

In the above specific examples, Ac represents an acetyl group, Bz represents a benzoyl group, Boc represents a tert-butoxycarbonyl group, Z represents a benzyloxycarbonyl group, Fmoc represents a fluorenylmethoxycarbonyl group, Troc represents a 2,2,2-trichloroethoxycarbonyl group, Ph represents a phenyl group, Nap represents a naphthyl group, Py represents a pyridyl group, t-Bu represents a tert-butyl group, Me represents a methyl group, Et represents an ethyl group, and Bn represents a benzyl group, respectively (hereinafter the same).

The nucleophilic compound (provided that trialkylsilyl vinyl ethers are excluded) used in the present invention include, for example, a compound represented by the formula (3):

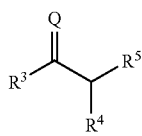

(3)

(wherein $R^3$ represents a hydrogen atom, a hydrocarbon group optionally having substituent(s), a heterocyclic group optionally having substituent(s), an alkoxy group optionally having substituent(s), an aryloxy group optionally having substituent(s), an aralkyloxy group optionally having substituent(s) or a substituted amino group; $R^4$ and $R^5$ each independently represent a hydrogen atom, a hydrocarbon group optionally having substituent(s), a heterocyclic group optionally having substituent(s), $EWG^1$ ($EWG^1$ represents an electron-withdrawing group), an alkoxy group optionally having substituent(s), an aryloxy group optionally having substituent(s), an aralkyloxy group optionally having substituent(s), an alkylthio group optionally having substituent(s), an arylthio group optionally having substituent(s), an aralkylthio group optionally having substituent(s), or a hydroxy group; Q represents a group giving a tautomer of the compound represented by the formula (3); and $R^3$ and $R^4$, $R^3$ and $R^5$, or $R^4$ and $R^5$ may be taken together to form a ring),
a compound represented by the formula (5):

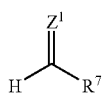

(5)

(wherein $R^7$ represents a hydrogen atom, a hydrocarbon group optionally having substituent(s), a heterocyclic group optionally having substituent(s), an alkoxy group optionally having substituent(s), an aryloxy group optionally having substituent(s) or an aralkyloxy group optionally having substituent(s), an alkylthio group optionally having substituent(s), an arylthio group optionally having substituent(s), an aralkylthio group optionally having substituent(s) or $EWG^2$ ($EWG^2$ represents an electron-withdrawing group), and $Z^1$ represents $N_2$, $P(R^8)_3$ (three of $R^8$, the same or different, represent a hydrogen atom, a hydrocarbon group optionally having substituent(s), a heterocyclic group optionally having substituent(s), an alkoxy group optionally having substituent(s), an aryloxy group optionally having substituent(s) or an aralkyloxy group optionally having substituent(s)) or $CR^9R^{10}$ ($R^9$ and $R^{10}$ each independently represent a hydrogen atom, a hydrocarbon group optionally having substituent(s), a heterocyclic group optionally having substituent(s), an alkoxy group optionally having substituent(s), an aryloxy group optionally having substituent(s), an aralkyloxy group optionally having substituent(s), an alkylthio group optionally having substituent(s), an arylthio group optionally having substituent(s), an aralkylthio group optionally having substituent(s), an amino group or a substituted amino group; provided that either one of $R^9$ and $R^{10}$ represents an alkoxy group optionally having substituent(s), an aryloxy group optionally having substituent(s), an aralkyloxy group optionally having substituent(s), an alkylthio group optionally having substituent(s), an arylthio group optionally having substituent(s), an aralkylthio group optionally having substituent(s), an amino group or a substituted amino group)),
a compound represented by the formula (7):

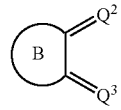

(7)

(wherein ring B represents an aliphatic ring or an aliphatic heterocycle; $Q^2$ and $Q^3$ each independently represent an oxygen atom, $NR^{17}$ ($R^{17}$ represents a hydrogen atom or a protective group) or a sulfur atom), for example, a benzene represented by the formula (21):

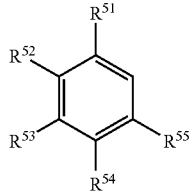

(21)

(wherein $R^{51}$ to $R^{55}$ each independently represent a hydrogen atom or a substituent; provided that $R^{53}$ and $R^{52}$, $R^{52}$ and $R^{53}$, $R^{53}$ and $R^{54}$, or $R^{54}$ and $R^{55}$ may be taken together to form a ring), and the like.

In the formula (3), the hydrocarbon group optionally having substituent(s) and the heterocyclic group optionally having substituent(s) represented by $R^3$, $R^4$ and $R^5$ may be the same as respective groups explained as the protective group of $R^1$ in the above-mentioned formula (2).

The alkoxy group optionally having substituent(s), the aryloxy group optionally having substituent(s), the aralkyloxy group optionally having substituent(s), and the substituted amino group represented by $R^3$, and the alkoxy group optionally having substituent(s), the aryloxy group optionally having substituent(s), the aralkyloxy group optionally having substituent(s), the alkylthio group optionally having substituent(s), the arylthio group optionally having substituent(s) and the aralkylthio group optionally having substituent(s) represented by $R^4$ and $R^5$ may be the same as respective groups explained in a substituent in the hydrocarbon group optionally having substituent(s) and the like explained as the protective group of $R^1$ in the above-mentioned formula (2).

$EWG^1$ represented by $R^4$ and $R^5$ represents an electron-withdrawing group. The electron-withdrawing group include, an acyl group optionally having substituent(s), an alkoxycarbonyl group optionally having substituent(s), an aryloxycarbonyl group optionally having substituent(s), an aralkyloxycarbonyl group optionally having substituent(s), an alkoxythiocarbonyl group optionally having substituent(s), an aryloxythiocarbonyl group optionally having substituent(s), an aralkyloxythiocarbonyl group optionally having substituent(s), an alkylthiocarbonyl group optionally having substituent(s), an arylthiocarbonyl group optionally having substituent(s), an aralkylthiocarbonyl group optionally having substituent(s), a carbamoyl group optionally having substituent(s), a cyano group, a nitro group, a halogen atom and the like.

The acyl group optionally having substituent(s), the alkoxycarbonyl group optionally having substituent(s), the aryloxycarbonyl group optionally having substituent(s), the aralkyloxycarbonyl group optionally having substituent(s), the alkylthiocarbonyl group optionally having substituent(s), the arylthiocarbonyl group optionally having substituent(s), the aralkylthiocarbonyl group optionally having substituent(s), the alkoxythiocarbonyl group optionally having substituent(s), the aryloxythiocarbonyl group optionally having substituent(s), the aralkyloxythiocarbonyl group optionally having substituent(s), the alkylthiocarbonyl group optionally having substituent(s), the arylthiocarbonyl group optionally having substituent(s), the aralkylthiocarbonyl group optionally having substituent(s), the carbamoyl group optionally having substituent(s) and the halogen atom in the electron-withdrawing group may be the same as respective groups explained in the substituent of the hydrocarbon group optionally having substituent (s) and the like explained as the protective group of $R^1$ in the above-mentioned formula (2).

When the electron-withdrawing group is an alkoxycarbonyl group optionally having substituent(s), an aryloxycarbonyl group optionally having substituent(s), an aralkyloxycarbonyl group optionally having substituent(s), an alkoxythiocarbonyl group optionally having substituent(s), an aryloxythiocarbonyl group optionally having substituent(s), an aralkyloxythicarbonyl group optionally having substituent(s), an alkylthiocarbonyl group optionally having substituent(s), an arylthiocarbonyl group optionally having substituent(s), an aralkylthiocarbonyl group optionally having substituent(s), a carbamoyl group optionally having substituent(s) or the like, the electron-withdrawing group is represented by the formula, for example, $R^h$—C(=$Z^1$)— ($R^h$ represents an alkoxy group optionally having substituent(s), an alkoxy group optionally having substituent(s), an aryloxy group optionally having substituent(s), an aralkyloxy group optionally having substituent(s), an alkylthio group optionally having substituent (s), an arylthio group optionally having substituent(s), an aralkylthio group optionally having substituent(s), an amino group, a substituted amino group or the like, and $Z^1$ represents an oxygen atom or a sulfur atom (the alkoxy group optionally having substituent(s), the aryloxy group optionally having substituent(s), the aralkyloxy group optionally having substituent(s), the alkylthio group optionally having substituent(s), the arylthio group optionally having substituent(s), the aralkylthio group optionally having substituent(s) and the substituted amino group may be the same as respective groups explained in the substituents of the hydrocarbon group optionally having substituent(s) and the like explained as a protective group of $R^1$ in the above-mentioned formula (2))).

The group giving a tautomer of the compound represented by the above-mentioned formula (3) represented by Q is not particularly limited as far as it is a group capable of giving a compound such that a compound represented by the above-mentioned formula (3) is a tautomer represented, for example, by the formula (3-1):

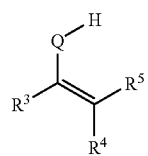

(3-1)

(wherein R to $R^5$ and Q are the same as defined above).

Specific examples of the group represented by Q capable of giving a tautomer of a compound represented by the formula (3) include, for example, an oxygen atom, $NR^6$ ($R^6$ represents a hydrogen atom or a protective group) or a sulfur atom and the like.

The protective group represented by $R^6$ in $NR^6$ may be the same as the protective group explained in $R^1$ in the above-mentioned formula (2).

In the formula (3), when $R^3$ and $R^4$, $R^3$ and $R^5$, or $R^4$ and $R^5$ are taken together to form a ring, the formed ring, which may be monocyclic, polycyclic, or fused cyclic, include a 4- to 8-membered aliphatic ring. In addition, —O—, —NH—, a carbonyl group (C=O), a thiocarbonyl group (C=S) or the like may be contained in the carbon chain constituting a ring. Specific examples of the ring in the case of ring formation include a cyclopentane ring, a cyclohexane ring, for example, a 5- to 7-membered lactone ring, for example, a 5- to 7-membered lactam ring and the like.

In the formula (3), it is preferable that either one of $R^4$ and $R^5$ is $EWG^1$ ($EWG^1$ is the same as defined above). In addition, in the case where $R^3$ and $R^4$, $R^3$ and $R^5$, or $R^4$ and $R^5$ are taken together to form a ring, $R^5$ is $EWG^1$ when $R^3$ and $R^4$ are taken together to form a ring, and $R^4$ is $EWG^1$ when $R^3$ and $R^5$ are taken together to form a ring. Further, when $R^4$ and $R^5$ are taken together to form a ring, the formed ring may have $EWG^1$, or may present a group derived from $EWG^1$. The group derived from $EWG^1$ includes a carbonyl group, a thiocarbonyl group and the like.

Specific examples of the compound represented by the formula (3) used in the present invention include the following compounds:

Exemplified Compound 3-1:

1) Exemplified Compound 3-1-1:

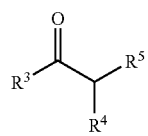

$R^3$: H, Me, Et, iPr, Ph, 4-Me—Ph, 4-Cl—Ph, Nap, Py, OMe, OEt, SMe, SEt, NMe$_2$, NEt$_2$, etc.
$R^4$: H, Me, Et, iPr, Ph, 4-Me—Ph, 4-Cl—Ph, Nap, Py, etc.
$R^5$: $EWG^1$
$EWG^1$: —CHO, Ac, Bz,
—COOMe, —COOEt, —COOBu$^t$, —COOBn,
—COSMe, —CONH$_2$, —CONMe$_2$, —CONEt$_2$,
—CN, —NO$_2$, —PO(OMe)$_2$, —SO$_2$Me, etc.

1) Exemplified Compound 3-1-2:

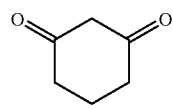

Exemplified Compound 3-2:

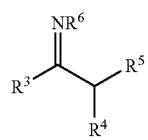

-continued

R³: H, Me, Et, iPr, Ph, 4-Me—Ph, 4-Cl—Ph,
Nap, Py, OMe, OEt, SMe, SEt, NMe₂, NEt₂, etc.
R⁴: H, Me, Et, iPr, Ph, 4-Me—Ph, 4-Cl—Ph,
Nap, Py, etc.
R⁵: EWG¹
  EWG¹: —CHO, Ac, Bz,
    —COOMe, —COOEt, —COOBuᵗ, —COOBn,
    —COSMe, —CONH₂, —CONMe₂, —CONEt₂,
    —CN, —NO₂, —PO(OMe)₂, —SO₂Me, etc.
R⁶: H, Me, Et, iPr, Ph, 4-Me—Ph, 4-Cl—Ph,
Nap, Py, COMe, COPh, COOMe, COOPh, COOCH₂Ph,
COOBuᵗ, CONMe₂, etc.

Exemplified Compound 3-3:

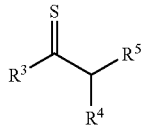

R³: H, Me, Et, iPr, Ph, 4-Me—Ph, 4-Cl—Ph,
Nap, Py, OMe, OEt, SMe, SEt, NMe₂, NEt₂, etc.
R⁴: H, Me, Et, iPr, Ph, 4-Me—Ph, 4-Cl—Ph,
Nap, Py, etc.
R⁵: EWG¹
  EWG¹: —CHO, Ac, Bz,
    —COOMe, —COOEt, —COOBuᵗ, —COOBn,
    —COSMe, —CONH₂, —CONMe₂, —CONEt₂,
    —CN, —NO₂, —PO(OMe)₂, —SO₂Me, etc.

In the above specific examples, $^i$Pr represents a 2-propyl group, and Buᵗ represents a tert-butyl group, respectively (hereinafter the same).

In the formula (5), the hydrocarbon group optionally having substituent(s), the heterocyclic group optionally having substituent(s), the alkoxy group optionally having substituent(s), the aryloxy group optionally having substituent(s), the aralkyloxy group optionally having substituent(s), the alkylthio group optionally having substituent(s), the arylthio group optionally having substituent(s) and the aralkylthio group optionally having substituent(s) represented by R⁷ may be the same as respective groups explained in R⁴ and R⁵ in the above-mentioned formula (3). In addition, an electron-withdrawing group represented by EWG² may be the same as an electron-withdrawing group represented by EWG¹ explained in R⁴ and R⁵ in the above-mentioned formula (3).

In P(R⁸)₃ in Z¹, three of R⁸, the same or different, represent a hydrogen atom, a hydrocarbon group optionally having substituent(s), a heterocyclic group optionally having substituent(s), an alkoxy group optionally having substituent(s), an aryloxy group optionally having substituent(s) or an aralkyloxy group optionally having substituent(s). Said hydrocarbon group optionally having substituent(s) and said heterocyclic group optionally having substituent(s) may be the same as respective groups explained as a protective group of R¹ in the above-mentioned formula (2). In addition, the alkoxy group optionally having substituent(s), the aryloxy group optionally having substituent(s), and the aralkyloxy group optionally having substituent(s) may be the same as respective groups explained as a substituent in the protective group of R¹.

In CR⁹R¹⁰, the hydrocarbon group optionally having substituent(s) and the heterocyclic group optionally having substituent(s) represented by R⁹ and R¹⁰ may be the same as respective groups explained as the protective group of R¹ in the above-mentioned formula (2). In addition, the alkoxy group optionally having substituent (s), the aryloxy group optionally having substituent(s), the aralkyloxy group optionally having substituent(s), the alkylthio group optionally having substituent(s), the arylthio group optionally having substituent(s), the aralkylthio group optionally having substituent(s) and the substituted amino group may be the same as respective groups explained as a substituent in the hydrocarbon group optionally having substituent(s) in the protective group of R¹ in the above-mentioned formula (2). In addition, in CR⁹R¹⁰, either one of R⁹ and R¹⁰ represents an alkoxy group optionally having substituent(s), an aryloxy group optionally having substituent(s), an aralkyloxy group optionally having substituent(s), an alkylthio group optionally having substituent (s), an arylthio group optionally having substituent (s), an aralkylthio group optionally having substituent(s), an amino group or a substituted amino group.

Meantime, R⁷ in the formula (5) is preferably an electron-withdrawing group represented by EWG².

Specific examples of the compound represented by the formula (5) include the following compounds:

Exemplified Compound 6-1:
1) Exemplified Compound 6-1-1:

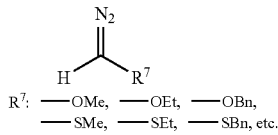

R⁷: —OMe, —OEt, —OBn,
    —SMe, —SEt, —SBn, etc.

2) Exemplified Compound 6-1-2:

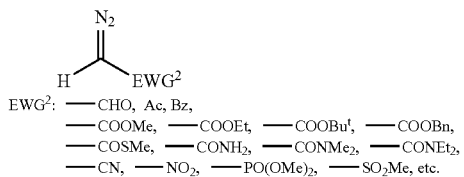

EWG²: —CHO, Ac, Bz,
    —COOMe, —COOEt, —COOBuᵗ, —COOBn,
    —COSMe, —CONH₂, —CONMe₂, —CONEt₂,
    —CN, —NO₂, —PO(OMe)₂, —SO₂Me, etc.

Exemplified Compound 6-2:

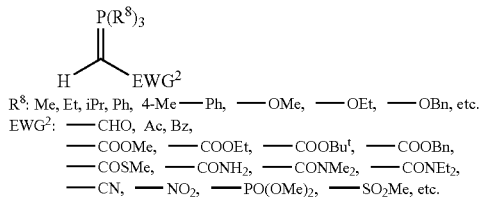

R⁸: Me, Et, iPr, Ph, 4-Me—Ph, —OMe, —OEt, —OBn, etc.
EWG²: —CHO, Ac, Bz,
    —COOMe, —COOEt, —COOBuᵗ, —COOBn,
    —COSMe, —CONH₂, —CONMe₂, —CONEt₂,
    —CN, —NO₂, —PO(OMe)₂, —SO₂Me, etc.

Exemplified Compound 6-3:

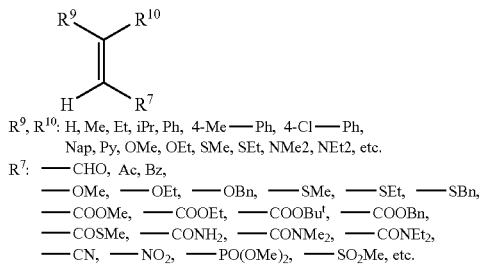

R⁹, R¹⁰: H, Me, Et, iPr, Ph, 4-Me—Ph, 4-Cl—Ph,
Nap, Py, OMe, OEt, SMe, SEt, NMe2, NEt2, etc.
R⁷: —CHO, Ac, Bz,
    —OMe, —OEt, —OBn, —SMe, —SEt, —SBn,
    —COOMe, —COOEt, —COOBuᵗ, —COOBn,
    —COSMe, —CONH₂, —CONMe₂, —CONEt₂,
    —CN, —NO₂, —PO(OMe)₂, —SO₂Me, etc.

Meantime, in the exemplified compound 6-3, it is preferable that either one of $R^9$ and $R^{10}$ is at least one group selected from the group consisting of an alkoxy group optionally having substituent(s), an aryloxy group optionally having substituent(s), an aralkyloxy group optionally having substituent(s), an alkylthio group optionally having substituent(s), an arylthio group optionally having substituent(s), an aralkylthio group optionally having substituent(s), an amino group and a substituted amino group, such as OMe, OEt, SMe, SEt, NMe, NEt and the like.

In the formula (7), the aliphatic ring represented by ring B includes, for example, an aliphatic ring having 4 to 20 carbon atoms. Also, said aliphatic ring includes a monocyclic aliphatic ring, and a polycyclic or fused aliphatic ring. Specific examples of the aliphatic ring include a cyclobutane ring, a cyclopentane ring, a cyclohexane ring, a tetrahydronaphthalene ring, a perhydronaphthalene ring and the like. Inter alia, the aliphatic ring is preferably an aliphatic heterocyclic ring having 5 to 14 carbon atoms.

The aliphatic heterocycle includes a 5- to 8-membered, preferably 5- or 6-membered, monocyclic aliphatic heterocycle, and a polycyclic or fused aliphatic heterocycle, having 2 to 20 carbon atoms, which contains at least one, preferably 1 to 3 heteroatom(s) such as a nitrogen atom, an oxygen atom and/or a sulfur atom as a heteroatom. Specific examples of the aliphatic heterocycle include a piperazine ring, a morpholine ring, a lactone ring, a lactam ring and the like. Inter alia, said aliphatic heterocycle is preferably an aliphatic heterocycle having 2 to 14 carbon atoms.

$NR^{17}$ represented by $Q^2$ and $Q^3$ may be the same as $NR^6$ represented by Q in the above-mentioned formula (3).

The compound represented by the formula (7) includes, for example, a compound represented by the formula (7-1):

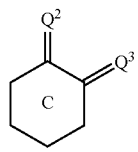

(7-1)

(wherein the ring C represents a cyclohexane ring, and $Q^2$ and $Q^3$ are the same as defined above.)

In the formula (7-1), a cyclohexane ring represented by the ring C may be monocyclic, polycyclic, or fused cyclic, and, further, the cyclohexane ring may have substituent(s) explained in the hydrocarbon group optionally having substituent(s) in the formula (2).

Specific examples of the compound represented by the formula (7-1) include the following compounds:

Exemplified Compound 7-1:

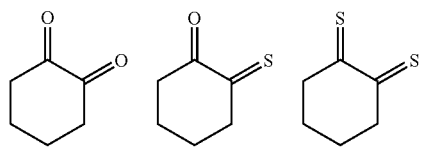

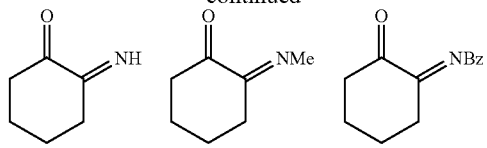

The imines and the nucleophilic compounds used in the present invention, commercially available products may be used, or those that have been appropriately prepared may be used.

The amines obtained by the process of the present invention includes, for example, an amine represented by the general formula (4):

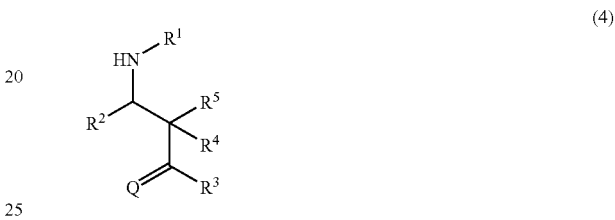

(4)

(wherein $R^1$ to $R^5$ and Q are the same as defined above),
an amine represented by the formula (6):

(6)

(wherein $R^1$, $R^2$, $R^7$ and $Z^1$ are the same as defined above),
an amine represented by the formula (8):

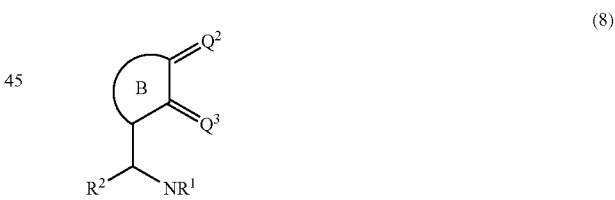

(8)

(wherein $R^1$, $R^2$, $Q^2$ and $Q^3$ are the same as defined above),
a compound represented by the formula (22):

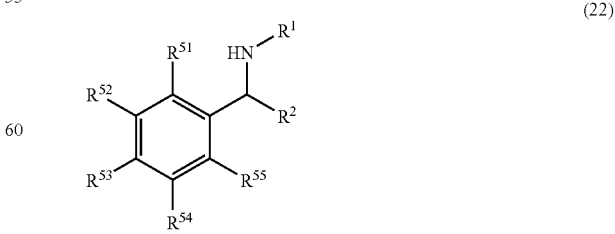

(22)

(wherein $R^1$, $R^2$ and $R^{51}$ to $R^{55}$ are the same as defined above) and the like.

These amines obtained by the process of the present invention are chiral compounds.

Also, when the optically active phosphoric acid derivative is used as the phosphoric acid derivative represented by the above-mentioned formula (1), the amine obtained by the process of the present invention is preferably an optically active amine. As the optically active amine, inter alia, the amine represented by the above-mentioned formula (4) is preferably obtained as an optically active amine represented by the formula (4a):

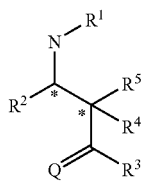

(4a)

(wherein * represents an asymmetric carbon atom, and $R^1$ to $R^5$ and Q are the same as defined above), and inter alia, the amine represented by the above-mentioned formula (6) is preferably obtained as an optically active amine represented by the formula (6a):

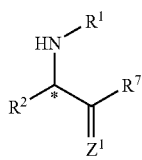

(6a)

(wherein * represents an asymmetric carbon atom, and $R^1$, $R^2$, $R^7$ and $Z^1$ are the same as defined above).

Meantime, in the formula (4a), when $R^4$ and $R^5$ are each the same group, the carbon atom to which $R^4$ and $R^5$ are bonded is not an asymmetric carbon atom.

Also, when the optically active phosphoric acid derivative is used as the phosphoric acid derivative represented by the formula (1), an optically active amine represented by the formula (8a):

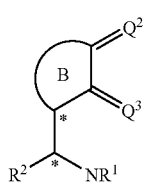

(8a)

(wherein ring B, $Q^2$, $Q^3$ and * are the same as defined above) is given as the amine represented by the above-mentioned formula (8).

Also, the amines represented by the above-mentioned formula (8) include, for example, an amine represented by the formula (8-1):

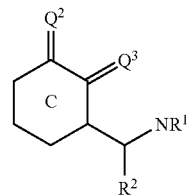

(8-1)

(wherein a ring C, $Q^2$ and $Q^3$ are the same as defined above) and the like.

Further, when the optically active phosphoric acid derivative is used as the phosphoric acid derivative represented by the formula (1), for example, an optically active amine represented by the formula (8a-1):

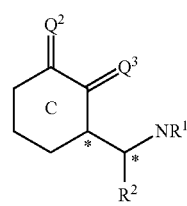

(8a-1)

(wherein ring C, $Q^2$, $Q^3$ and * are the same as defined above) is given as the amine represented by the above-mentioned formula (8a-1). Provided that, the optically active amines represented by the formula (8a-1) are also a preferable compound of the optically active amines represented by the formula (8a).

Meantime, in the process of the present invention, an optically active compound (i.e., the compound in which $R^4$ and $R^5$ are not the same group) represented by the formula (3a):

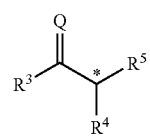

(3a)

(wherein $R^3$ to $R^5$, Q and * are the same as defined above) may be used as the nucleophilic compound among the compounds represented by the above-mentioned formula (3).

Specific examples of the amines represented by the formula (4a) obtained by the process of the present invention include, for example, compounds represented by the following formulae:

Exemplified Compound 4a-1:

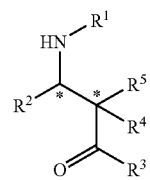

-continued

R$^1$: Ac, Bz, Boc, Z, Fmoc, Troc, etc.
R$^2$: Ph, 4-Me—Ph, 4-Cl—Ph,
  Nap, Py, t-Bu, —CH═CH—CH$_2$,
  1-Propynyl, Ac, —COOMe, —COOEt,
  —COOBn, etc.
R$^3$:, R$^4$: H, Me, Et, iPr, Ph, 4-Me—Ph, 4-Cl—Ph,
  Nap, Py, OMe, OEt, OBn, SMe, SEt, SBn, etc.
R$^5$: EWG$^1$
  EWG$^1$: —CHO, Ac, Bz,
    —COOMe, —COOEt, —COOBu$^t$, —COOBn,
    —COSMe, —CONH$_2$, —CONMe$_2$, —CONEt$_2$,
    —CN, —NO$_2$, —PO(OMe)$_2$, —SO$_2$Me, etc.

Exemplified Compound 4a-2:

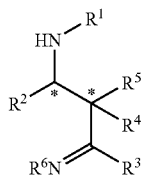

R$^1$: Ac, Bz, Boc, Z, Fmoc, Troc, etc.
R$^2$: Ph, 4-Me—Ph, 4-Cl—Ph,
  Nap, Py, t-Bu, —CH═CH—CH$_2$,
  1-Propynyl, Ac, —COOMe, —COOEt,
  —COOBn, etc.
R$^3$:, R$^4$: H, Me, Et, iPr, Ph, 4-Me—Ph, 4-Cl—Ph,
  Nap, Py, OMe, OEt, OBn, SMe, SEt, SBn, etc.
R$^5$: EWG$^1$
  EWG$^1$: —CHO, Ac, Bz,
    —COOMe, —COOEt, —COOBu$^t$, —COOBn,
    —COSMe, —CONH$_2$, —CONMe$_2$, —CONEt$_2$,
    —CN, —NO$_2$, —PO(OMe)$_2$, —SO$_2$Me, etc.
R$^6$: H, Me, Et, iPr, Ph, 4-Me—Ph, 4-Cl—Ph,
  Nap, Py, OMe, OEt, OBn, SMe, SEt, SBn, etc.

Exemplified Compound 4a-3:

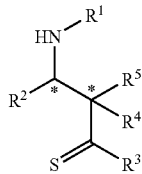

R$^1$: Ac, Bz, Boc, Z, Fmoc, Troc, etc.
R$^2$: Ph, 4-Me—Ph, 4-Cl—Ph,
  Nap, Py, t-Bu, —CH═CH—CH$_2$,
  1-Propynyl, Ac, —COOMe, —COOEt,
  —COOBn, etc.
R$^3$:, R$^4$: H, Me, Et, iPr, Ph, 4-Me—Ph, 4-Cl—Ph,
  Nap, Py, OMe, OEt, OBn, SMe, SEt, SBn, etc.
R$^5$: EWG$^1$
  EWG$^1$: —CHO, Ac, Bz,
    —COOMe, —COOEt, —COOBu$^t$, —COOBn,
    —COSMe, —CONH$_2$, —CONMe$_2$, —CONEt$_2$,
    —CN, —NO$_2$, —PO(OMe)$_2$, —SO$_2$Me, etc.

Meantime, when R$^4$ and R$^5$ are the same group, the carbon atom to which R$^4$ and R$^5$ in the amines represented by the formula (4a) obtained by the process of the present invention are bonded is not an asymmetric carbon atom.

Specific examples of the amines represented by the formula (6a) obtained by the process of the present invention include, for example, compounds represented by the following formulae:

Exemplified Compound 6a-1:
1) Exemplified Compound 6a-1-1

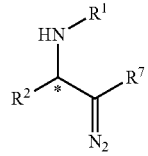

R$^1$: Ac, Bz, Boc, Z, Fmoc, Troc, etc.
R$^2$: Ph, 4-Me—Ph, 4-Cl—Ph,
  Nap, Py, t-Bu, —CH═CH—CH$_2$,
  1-Propynyl, Ac, —COOMe, —COOEt,
  —COOBn, etc.
R$^7$: —OMe, —OEt, —OBn,
  —SMe, —SEt, —SBn, etc.

2) Exemplified Compound 6a-1-2

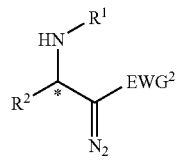

R$^1$: Ac, Bz, Boc, Z, Fmoc, Troc, etc.
R$^2$: Ph, 4-Me—Ph, 4-Cl—Ph,
  Nap, Py, t-Bu, —CH═CH—CH$_2$,
  1-Propynyl, Ac, —COOMe, —COOEt,
  —COOBn, etc.
EWG$^2$: —CHO, Ac, Bz,
  —OMe, —OEt, —OBn, —SMe, —SEt, —SBn,
  —COOMe, —COOEt, —COOBu$^t$, —COOBn,
  —COSMe, —CONH$_2$, —CONMe$_2$, —CONEt$_2$,
  —CN, —NO$_2$, —PO(OMe)$_2$, —SO$_2$Me, etc.

Exemplified Compound 6a-2:

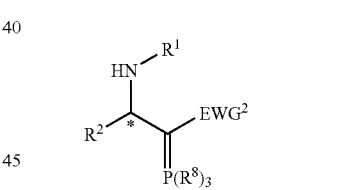

R$^1$: Ac, Bz, Boc, Z, Fmoc, Troc, etc.
R$^2$: Ph, 4-Me—Ph, 4-Cl—Ph,
  Nap, Py, t-Bu, —CH═CH—CH$_2$,
  1-Propynyl, Ac, —COOMe, —COOEt,
  —COOBn, etc.
R$^8$: Me, Et, iPr, Ph, 4-Me—Ph,
  OMe, OEt, OBn, SMe, SEt, SBn, etc.
EWG$^2$: —CHO, Ac, Bz,
  —COOMe, —COOEt, —COOBu$^t$, —COOBn,
  —COSMe, —CONH$_2$, —CONMe$_2$, —CONEt$_2$,
  —CN, —NO$_2$, —PO(OMe)$_2$, —SO$_2$Me, etc.

Exemplified Compound 6a-3:

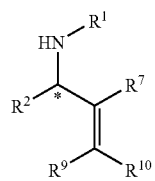

-continued

R¹: Ac, Bz, Boc, Z, Fmoc, Troc, etc.
R²: Ph, 4-Me—Ph, 4-Cl—Ph,
Nap, Py, t-Bu, —CH=CH—CH₂,
1-Propynyl, Ac, —COOMe, —COOEt,
—COOBn, etc.
R⁹, R¹⁰: H, Me, Et, iPr, Ph, 4-Me—Ph, 4-Cl—Ph,
Nap, Py, OMe, OEt, SMe, SEt, NMe2, NEt2, etc.
R¹¹: Me, Et, iPr, Ph, 4-Me—Ph, etc.
R⁷: —CHO, Ac, Bz,
—OMe, —OEt, —OBn, —SMe, —SEt, —SBn,
—COOMe, —COOEt, —COOBuᵗ, —COOBn,
—COSMe, —CONH₂, —CONMe₂, —CONEt₂,
—CN, —NO₂, —PO(OMe)₂, —SO₂Me, etc.

In the formulae (21) and (22) and the like, the substituent represented by $R^{51}$ to $R^{55}$ includes the same group as those explained in the substituent such as the aforementioned substituted hydrocarbon group and the like.

Specific examples of the benzenes represented by the formula (21) include, for example, benzene, toluene, ethylbenzene, isopropylbenzene, xylene, diethylbenzene, diisopropylbenzene, trimethylbenzene, triethylbenzene, triisopropylbenzene, methoxybenzene, ethoxybenzene, isopropoxybenzene, dimethoxybenzene, diethoxybenzene, diisopropoxybenzene, trimethoxybenzene, triethoxybenzene, triisopropoxybenzene, trifluoromethylbenzene, aniline, acetoanilide and the like.

The compound represented by the formula (22) obtained in the process of the present invention is preferably an optically active compound. Said optically active compound is represented, for example, by the formula (22a):

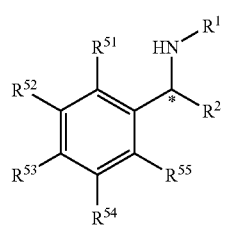

(22a)

(wherein $R^1$, $R^2$, $R^{51}$ to $R^{55}$ and * are the same as defined above)

Specific examples of the compound represented by the formula (22a) include, for example, a compound represented by the following formula:

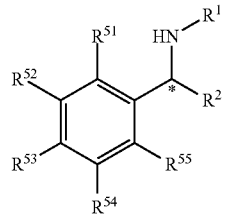

R¹: Ac, Bz, Boc, Z, Fmoc, Troc, etc.
R²: Ph, 4-Me—Ph, 4-Cl—Ph,
Nap, Py, t-Bu, —CH=CH—CH₂,
1-Propynyl, Ac, —COOMe, —COOEt,
—COOBn, etc.
R⁵¹-R⁵⁵: H, Me, Et, Pr, iPr, Ph, Cl, Br, I, OMe, OEt,
OPr, OiPr, OBn, etc.

The present invention 16) will be explained. In the unsaturated heterocyclic compound represented by the above-mentioned formula (14) as a nucleophilic compound used in the present invention, examples of the monocyclic heterocycle represented by ring E, having at least one double bond, include a 5-membered ring, a 6-membered ring and the like. Also, said ring E may have a heteroatom such as a sulfur atom, a nitrogen atom and the like, and a heteroatom group such as $NR^{27}$ ($R^{27}$ represents a hydrogen atom or a protective group) other than S (sulfur atom) or $NR^{26}$. Further, the ring E may have substituent(s). Provided that, when the ring E has substituent(s), said substituent may be the same as the substituent explained in the heterocycle optionally having substituent(s) in the above-mentioned formula (2). Examples of a protective group represented by $R^{26}$ in $NR^{26}$, and a protective group represented by $R^{27}$ in $NR^{27}$ include the same groups as the protective group explained in $R^1$ in the above-mentioned formula (2).

Specific examples of the 5-membered ring of the ring E include, for example, a thiophene ring, a pyrrole ring and the like. Specific examples of the 6-membered ring include, for example, a pyridine ring, a pyrazine ring and the like. Specific examples of the unsaturated heterocyclic compound represented by the formula (14) include, for example, the following compounds:

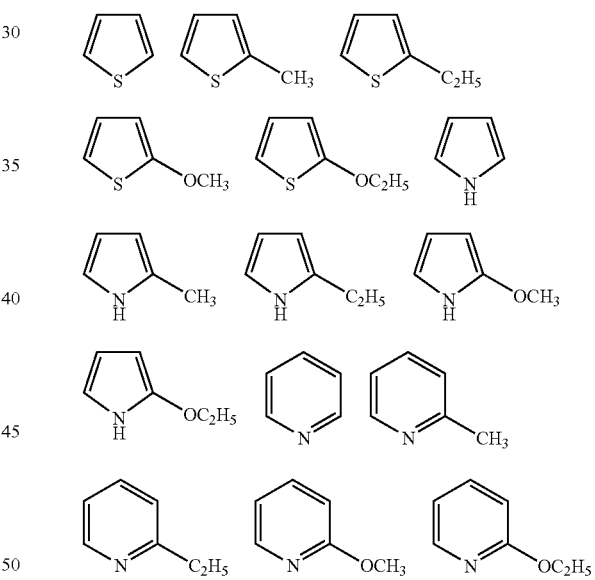

The amines represented by the above-mentioned formula (15-1) and/or the above-mentioned formula (15-2) obtained by reacting the nucleophilic compound which is the unsaturated heterocyclic compound represented by the above-mentioned formula (14), with the imine compound have a different production ratio thereof, depending on the kind of the nucleophilic compound which is the unsaturated heterocyclic compound represented by the formula (14) to be used, a catalyst, reaction conditions and the like.

The amines represented by the above-mentioned formula (15-1) and/or the above-mentioned formula (15-2) obtained by reacting a nucleophilic compound which is an unsaturated heterocyclic compound represented by the above-mentioned formula (14), with an imine compound is preferably obtained with an optically active amine represented by the formula (15-1a):

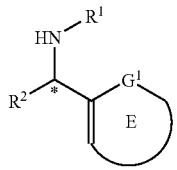

(15-1a)

and/or the formula (15-2a):

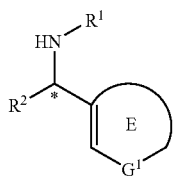

(15-2a)

(wherein * represents an asymmetric carbon atom, and $R^1$, $R^2$ $G^1$ and a ring E are the same as defined above).

When the nucleophilic compound used in the present invention is the unsaturated heterocyclic compound represented by the above-mentioned formula (16), the heteroatom represented by $G^2$ in the formula (16) includes an oxygen atom, a sulfur atom, a nitrogen atom and the like. The heteroatomic group includes $NR^{28}$ ($R^{28}$ represents a hydrogen atom or a protective group) and the like.

The heterocycle having at least one double bond represented by ring F in the formula (16) include a 5-membered ring, a 6-membered ring and the like. Said ring F may have a heteroatom such as a sulfur atom, a nitrogen atom and the like, and $NR^{29}$ ($R^{29}$ represents a hydrogen atom or a protective group) other than the aforementioned heteroatom. The heteroatomic group includes $NR^{26}$ ($R^{26}$ represents a hydrogen atom or a protective group) and the like.

Also, the protective group represented by $R^{28}$ in $NR^{28}$, and the protective group represented by $R^{29}$ in $NR^{29}$ include the same groups as the protective groups explained in $R^1$ in the above-mentioned formula (2).

Further, said ring F may have substituent(s). Provided that, the substituent when the ring F has the substituent(s) is the same as group explained in the heterocycle optionally having substituent(s) in the above-mentioned formula (2).

The ring F may be any ring as far as a heteroatom or a heteroatomic group represented by said G2 and a double bond are adjacent each other in the ring.

Specific examples of the 5-membered ring of ring F include, for example, a thiophene ring, a furan ring, a pyrrole ring and the like. Specific examples of the 6-membered ring include, for example, a pyridine ring, a pyrazine ring and the like.

A substituent in the aromatic ring optionally having substituent(s) and in the aromatic ring or the heterocycle optionally having substituent(s) represented by ring I in the formula (16) are the same as the substituent explained in the heterocycle optionally having substituent (s) in the formula (2). The aromatic ring optionally having substituent(s) includes a benzene ring and the like. The heterocycle optionally having substituent (s) includes a pyridine ring and the like. Provided that, above-mentioned formula (16) is conveniently represented by a benzene ring.

Specific examples of the unsaturated heterocyclic compound represented by the formula (16) include, for example, the following compounds:

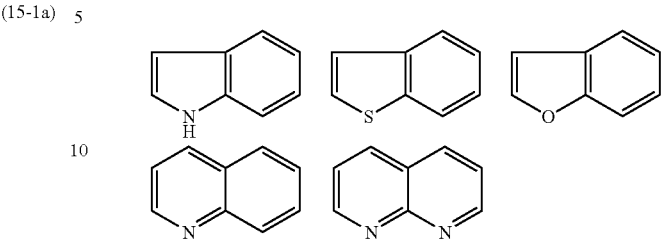

The amines represented by the above-mentioned formula (17) obtained by reacting the nucleophilic compound which is the unsaturated heterocyclic compound represented by the above-mentioned formula (16) and an imine compound is preferably obtained with an optically active amine represented by the formula (17a):

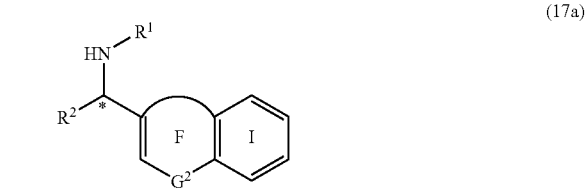

(17a)

(wherein * represents an asymmetric carbon atom, and $R^1$, $R^2$, $G^2$ and ring F are the same as defined above).

Inter alia, the above-mentioned unsaturated heterocyclic compound represented by the formula (16) is preferably an unsaturated heterocyclic compound represented by the formula (16-1):

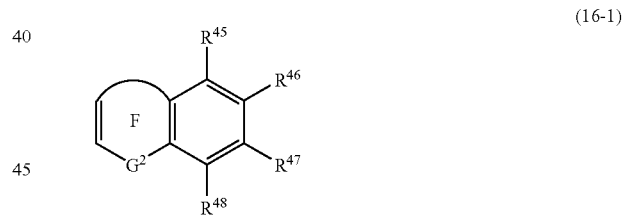

(16-1)

(wherein $R^{45}$ to $R^{48}$ each independently represent a hydrogen atom or a substituent, and $G^2$ and ring F are the same as defined above). The obtained amine represented by the formula (17-1) is preferably an amine represented by the formula:

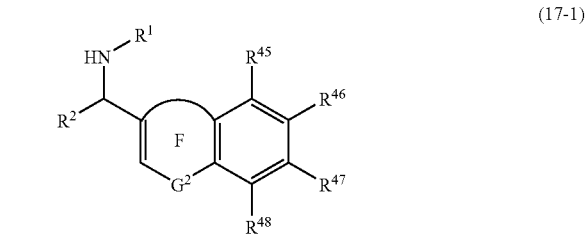

(17-1)

(wherein $R^1$, $R^2$, $R^{45}$ to $R^{48}$, $G^2$ and ring F are the same as defined above), and is more preferably an optically active amine represented by the formula (17-1a):

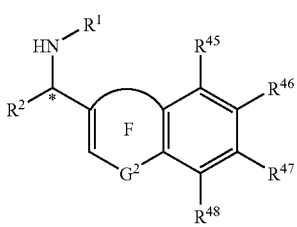

(17-1a)

(wherein $R^1$, $R^2$, $R^{45}$ to $R^{48}$, $G^2$, ring F and * are the same as defined above). Herein, the substituents represented by $R^{45}$ to $R^{48}$ are the same as defined above.

In the reaction of the imine compound represented by the above-mentioned formula (2) and the furan represented by the above-mentioned formula (12), the substituents represented by $R^{41}$ to $R^{43}$ in the formula (12) are each independently the same as defined above. $R^{41}$ is preferably an electron donating group, more preferably an electron-withdrawing group such as an alkoxy group optionally having substituent(s), an aryloxy group optionally having substituent(s), an aralkyloxy group optionally having substituent(s), a hydrocarbon group optionally having substituent(s) and the like.

Specific examples of the furans represented by the formula (12) include 2-methoxyfuran, 2-ethoxyfuran, 2-methylfuran, 2-ethylfuran, 2-propylfuran, 2-(2-propyl)furan and the like.

Also, the obtained amine represented by the above-mentioned formula (13), an optically active amine represented by the formula (13a):

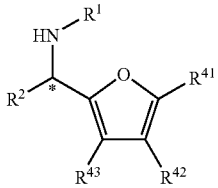

(13a)

(wherein * represents an asymmetric carbon atom, and $R^1$, $R^2$ and $R^{41}$ to $R^{43}$ are the same as defined above) is preferably obtained.

In the formula (31) and the like, the alkyl group in the alkyl-substituted phenyl group represented by $Ar^1$ to $Ar^5$, and the alkyl group represented by $R^{45}$ and $R^{46}$ in the formulae (32), (33) and the like may be, for example, an alkyl group having 1 to 6 carbon atom(s), which may be straight-chain, branched, or cyclic, and specific examples thereof include methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpentyl, 3-methylpentyl, 4-methylpentyl, cyclopropyl, cyclobutyl, cyclopentyl, cyclohexyl and the like. Inter alia, said alkyl group is preferably an alkyl group having 1 to 3 carbon atom(s).

Specific examples of the alkyl-substituted phenyl group represented by $Ar^1$ to $Ar^5$ include methylphenyl, ethylphenyl, isopropylphenyl, dimethylphenyl, diethylphenyl, diisobutylphenyl, trimethylphenyl, triethylphenyl, triisopropylphenyl, 2,4,6-trimethlphentyl and the like.

In the phosphoric acid derivative represented by the above-mentioned formula (1) used in the present invention, the spacer represented by $A^1$ includes a divalent organic group optionally having substituent(s) and the like. Said divalent organic group optionally having substituent(s) includes a divalent organic group and a divalent organic group having substituent(s) (substituted divalent organic group). Specific examples of the divalent organic group optionally having substituent(s) include an alkylene group optionally having substituent(s), an arylene group optionally having substituent(s) and the like.

The alkylene group optionally having substituent(s) includes an alkylene group and a substituted alkylene group. The alkylene group may be, for example, an alkylene group having 1 to 10 carbon atoms, which may be straight-chain, branched, or cyclic, and specific examples thereof include methylene, ethylene, trimethylene, propylene, tetramethylene, butylene, 1,2-dimethylethylene, pentylene, hexylene, 1,2-cyclohexylene and the like.

Examples of the substituted alkylene group include an alkylene group in which at least one hydrogen atom of the aforementioned alkylene group is substituted with a substituent. The substituent may be the same as the substituent explained in the hydrocarbon group optionally having substituent(s) explained as a protective group of $R^1$ in the formula (2). Specific examples of the substituted alkylene group include 1,2-diphenylethylene, 1,2-di(4-methylphenyl)ethylene, 1,2-dicyclohexylethylene, 1,3-dioxolane-4,5-diyl and the like.

The arylene group optionally having substituent(s) includes an arylene group and a substituted arylene group. The arylene group includes, for examples, an arylene group having 6 to 20 carbon atoms, and specific examples thereof include phenylene, biphenyldiyl, binaphthalenediyl and the like. The substituted arylene group includes an arylene group in which at least one hydrogen atom of the arylene group is substituted with a substituent. The substituent may be the same as the substituent explained in the hydrocarbon group optionally having substituent(s) explained as a protective group of $R^1$ in the above-mentioned formula (2).

These divalent organic groups may have at least one group such as an oxygen atom, a carbonyl group and the like at an arbitrary position of the terminal or the chain in said organic groups.

The divalent organic group having substituent(s) (substituted divalent organic group) includes a group in which at least one hydrogen atom of the aforementioned divalent organic group having substituent(s) is substituted with the aforementioned substituent.

Also, when the phosphoric acid derivative represented by the formula (1) is the optically active phosphoric acid derivative, the spacer represented by $A^1$ is preferably a spacer having an optically active site. Specific examples of said spacer having an optically active site include 1,2-dimethylethylene, 1,2-cyclohexylene, 1,2-diphenylethylene, 1,2-di(4-methylphenyl)ethylene group, 1,2-dicyclohexylethylene, 1,3-dioxolane-4,5-diyl, diphenyldiyl, binaphthalenediyl and the like. These spacers having an optically active site include an (R)-form, an (S)-form, an (R,R)-form and an (S,S)-form.

The divalent nonmetal atom represented by $X^1$ and $X^2$ includes, for example, an oxygen atom, a sulfur atom and the like. The divalent nonmetal atomic group includes, for example, $-NR^{13}-$ ($R^{13}$ represents a hydrogen atom, a hydrocarbon group optionally having substituent(s) or an acyl group optionally having substituent(s)), and $-CR^{15}R^{16}-$ {$R^{15}$ and $R^{16}$ each independently represent a hydrogen atom, a hydrocarbon group optionally having substituent(s) or $EWG^3$ ($EWG^3$ represents an electron-withdrawing group). Provided that, either one of $R^{15}$ and $R^{16}$ is $EWG^3$}.

In the divalent nonmetal atomic group, the hydrocarbon group optionally having substituent(s) and the acyl group optionally having substituent(s) in $-NR^{13}-$ may be the same as respective groups explained as a protective group of $R^1$ in the formula (2).

The hydrocarbon group optionally having substituent(s) represented by $R^{15}$ or $R^{16}$ may be the same as the hydrocarbon group optionally having substituent(s) explained as a protective group of $R^1$ in the formula (2).

$EWG^3$ may be the same as $EWG^1$ explained in $R^4$ and $R^5$ in the above-mentioned formula (3).

Specific examples of the phosphoric acid derivative represented by the formula (1) include, for example, compounds represented by the following formulae:

Exemplified Compound 1-1:

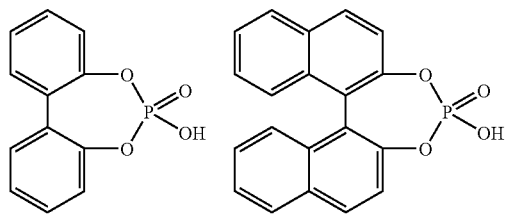

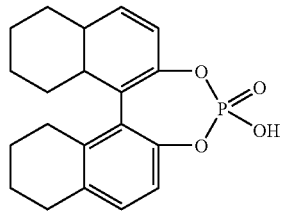

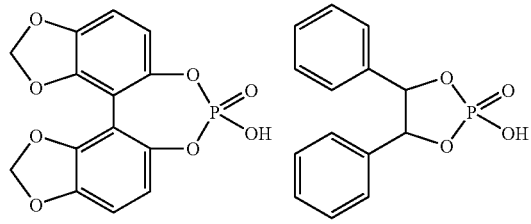

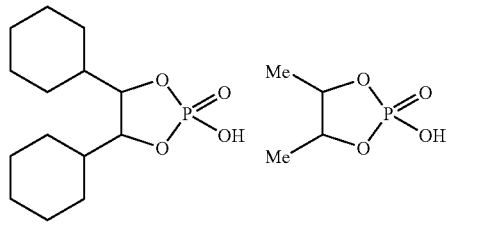

Exemplified Compound 1-2:

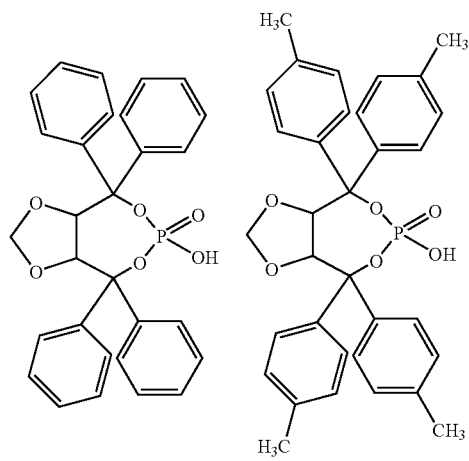

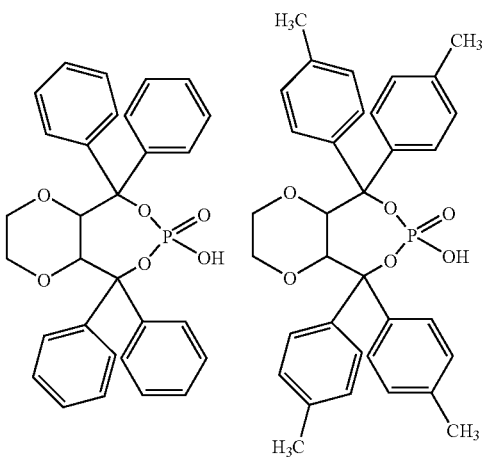

Exemplified Compound 1-3:

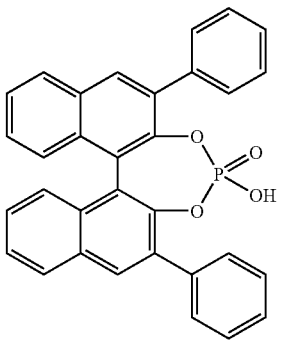

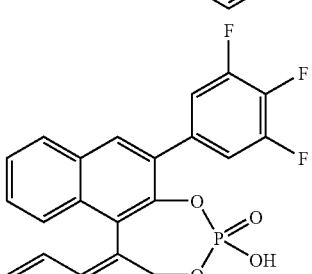

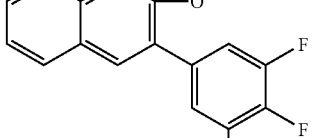

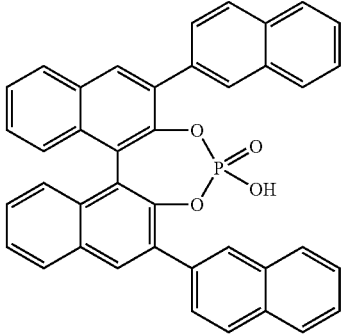

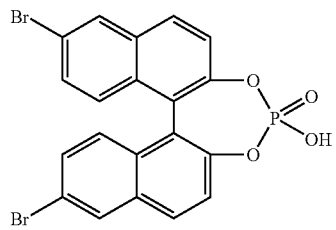
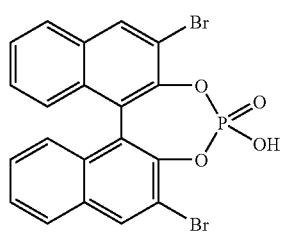
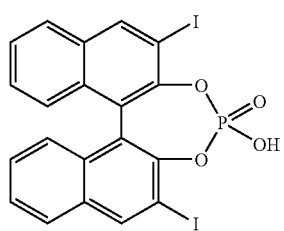
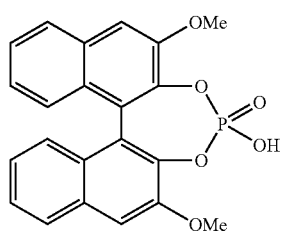
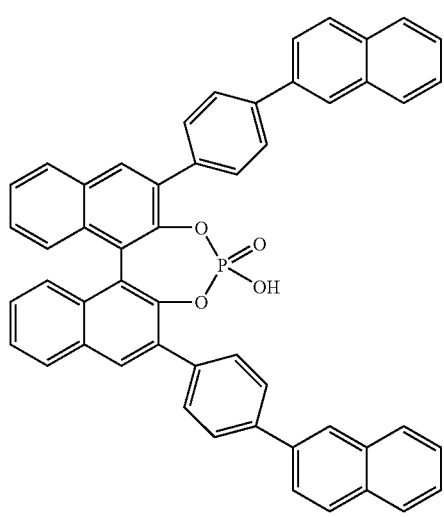
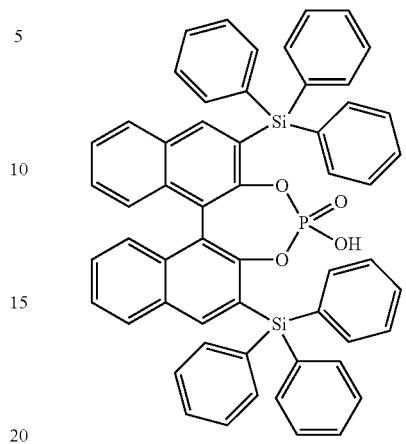
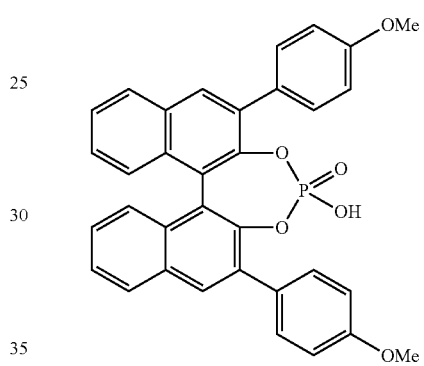
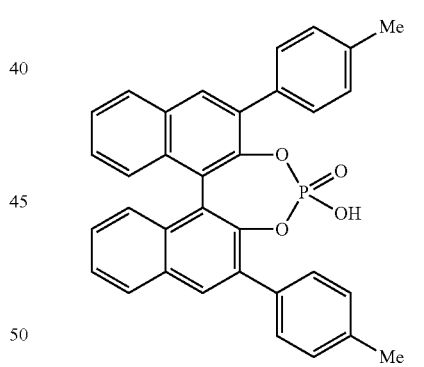
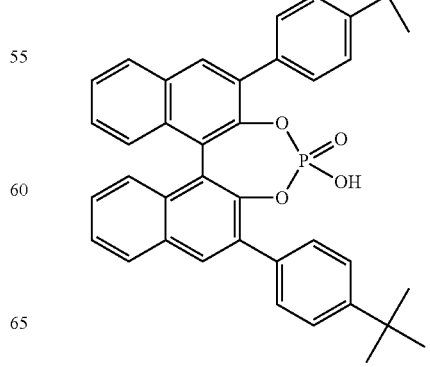

-continued
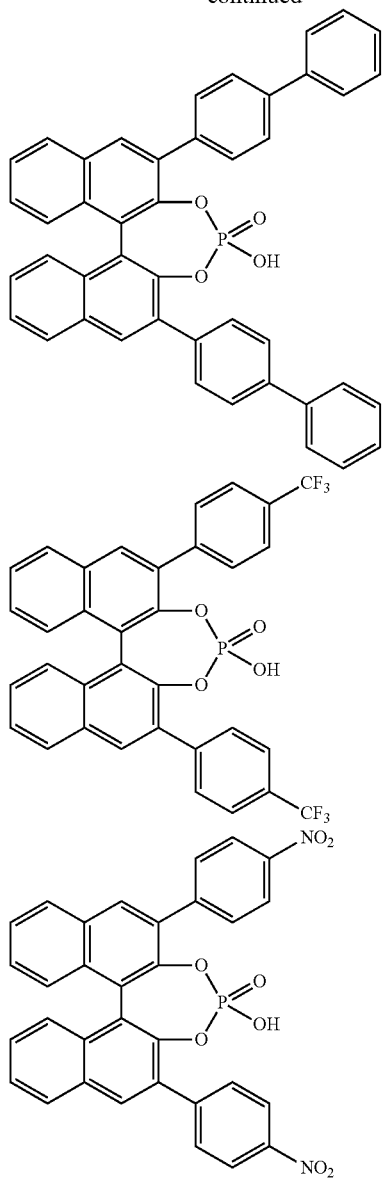
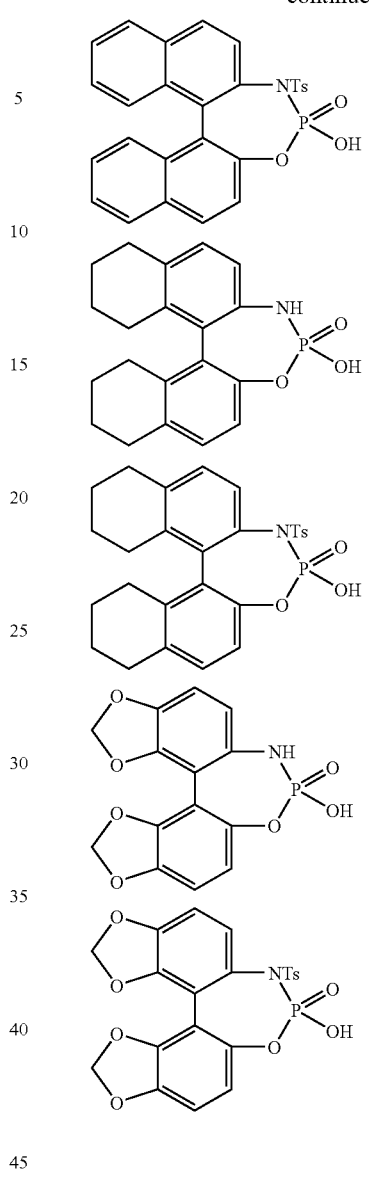
Exemplified Compound 1-4:
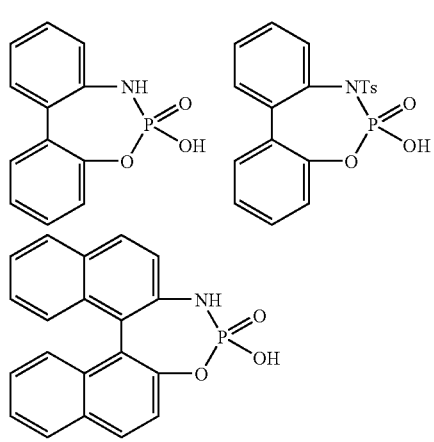
Exemplified Compound 1-5:
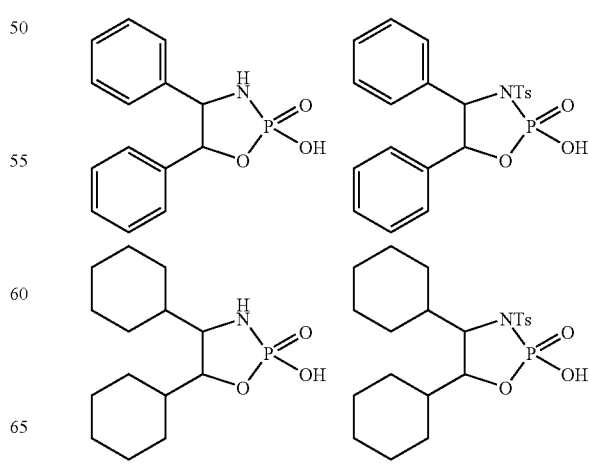

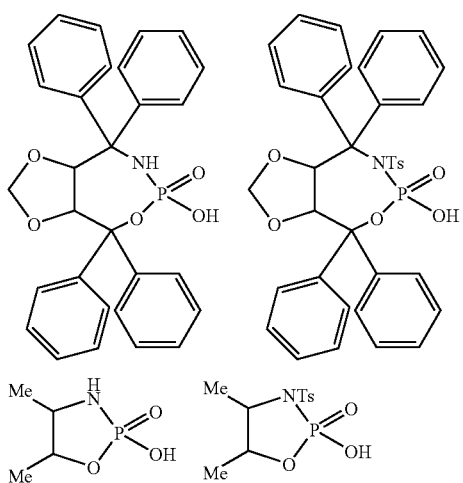
Exemplified Compound 1-6:
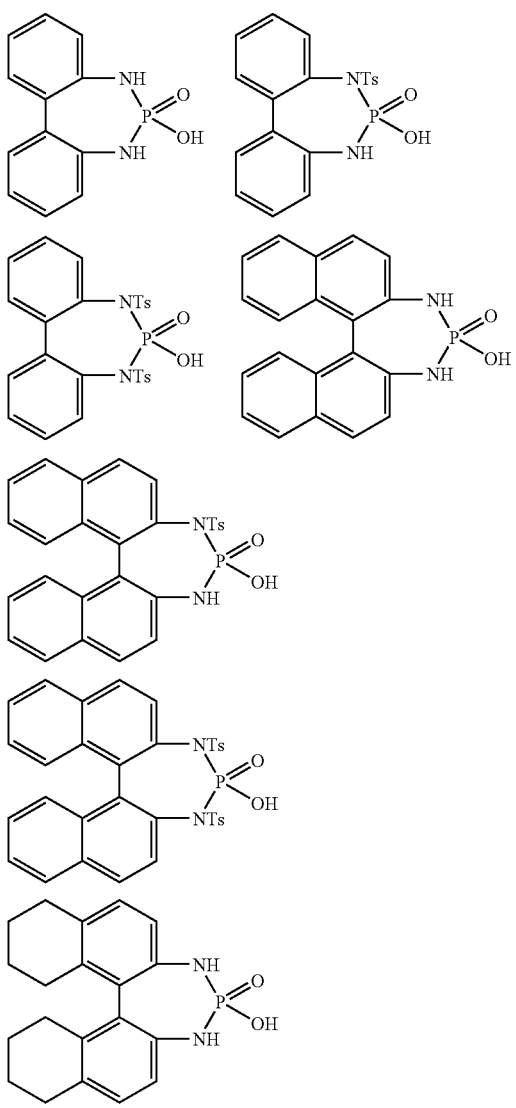
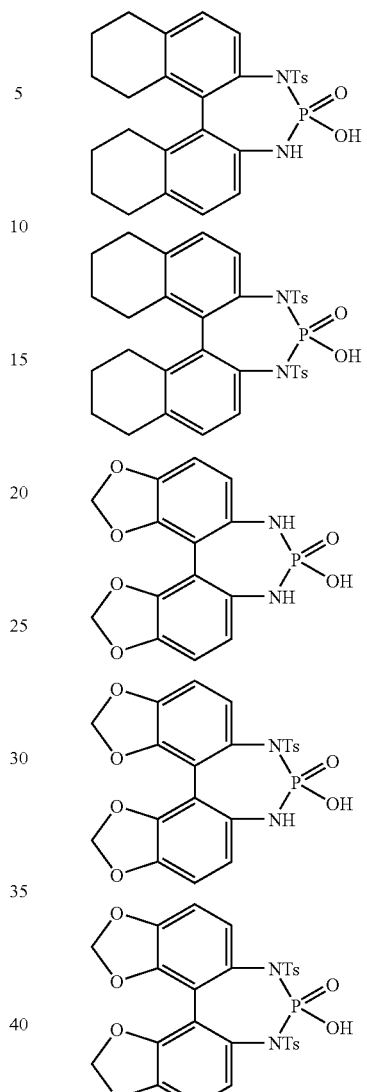
Exemplified Compound 1-7:
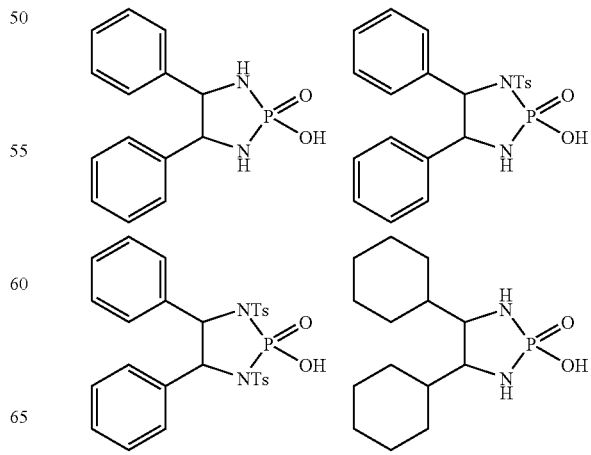

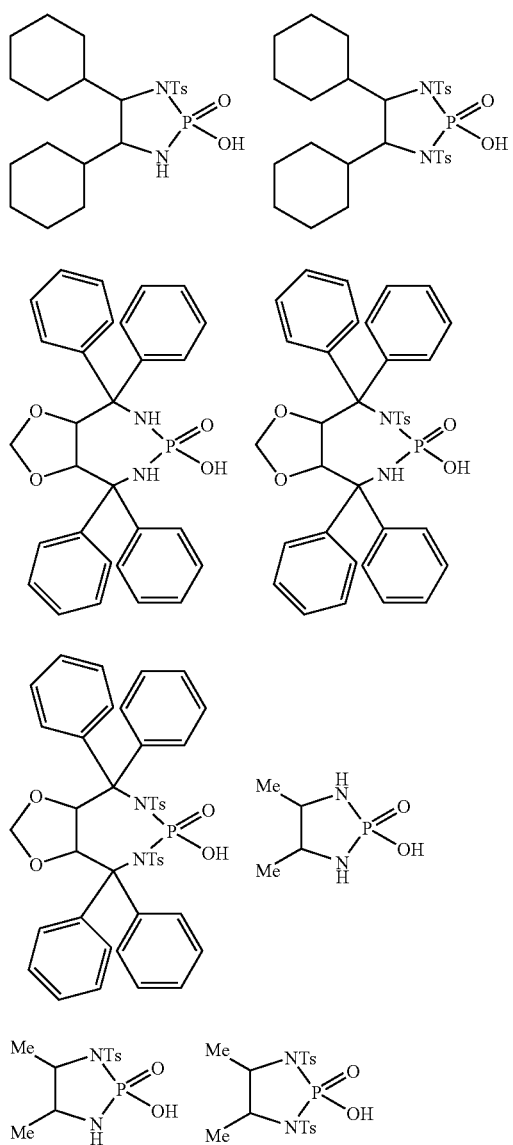
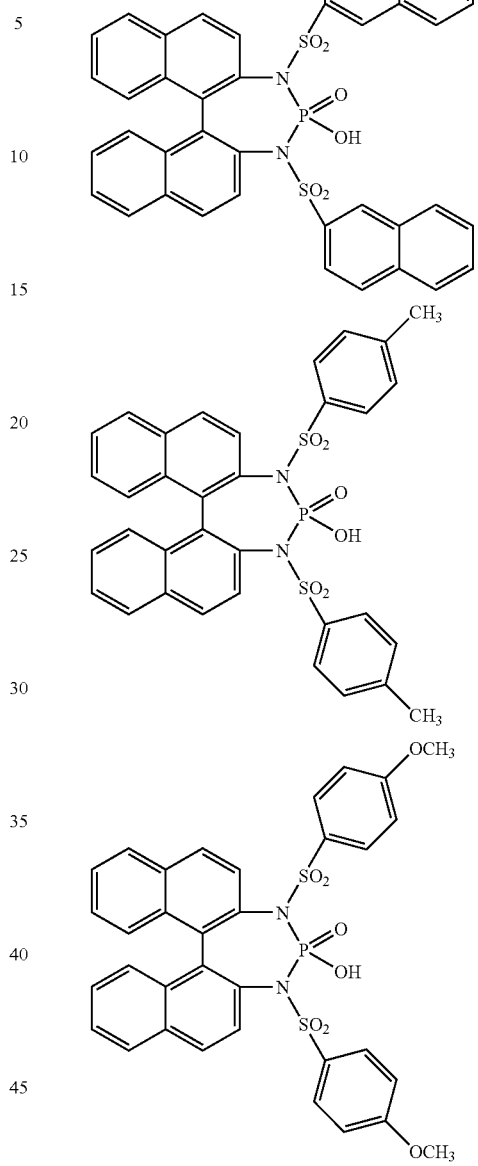
Exemplified Compound 1-8:
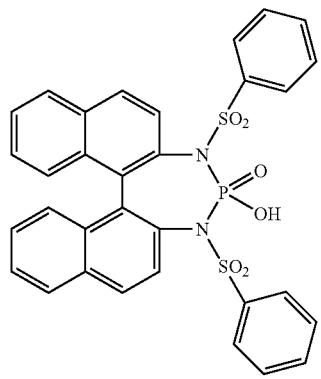
Exemplified Compound 1-9:
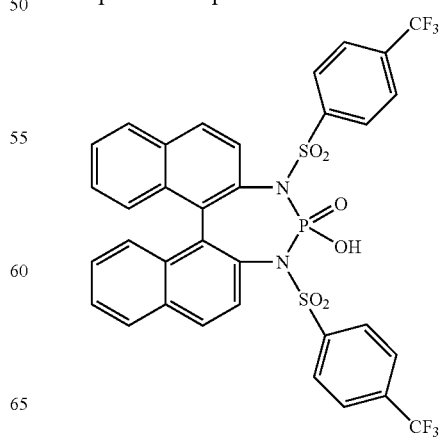

-continued
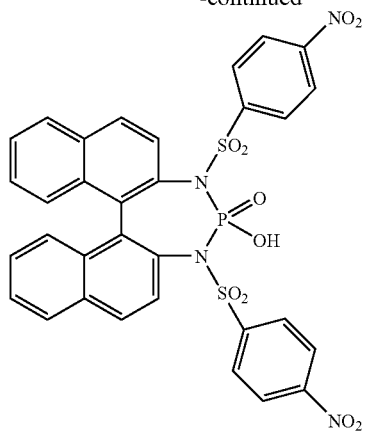
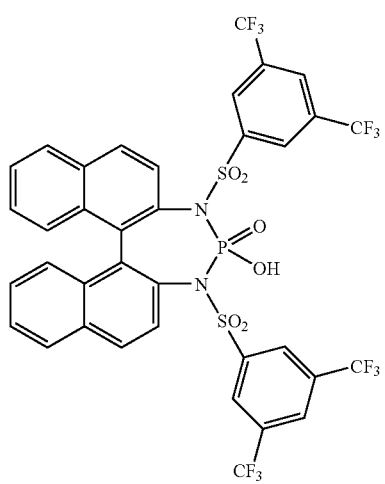
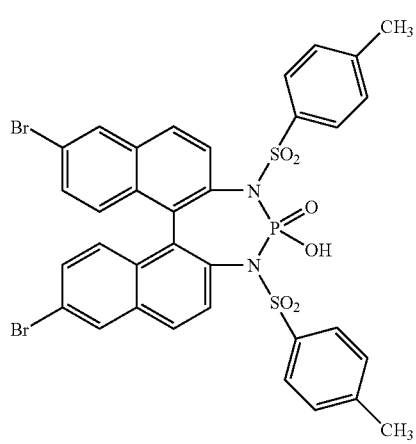
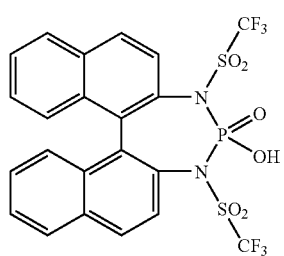
Exemplified Compound 1-10:
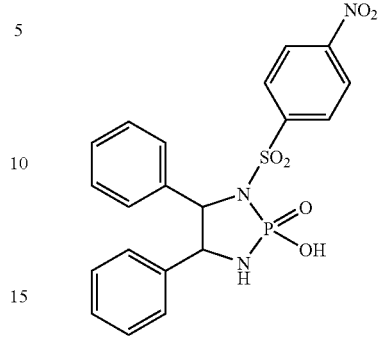
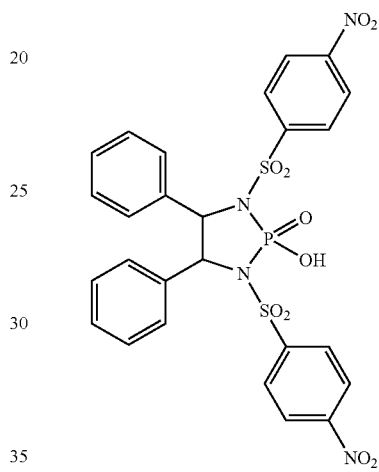
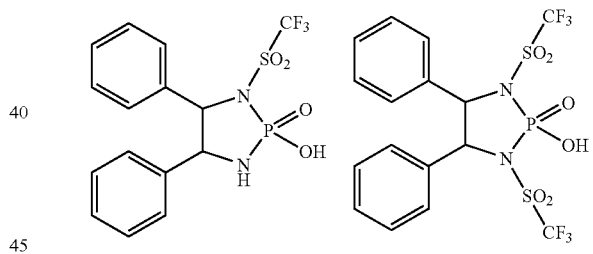
Exemplified Compound 1-11:
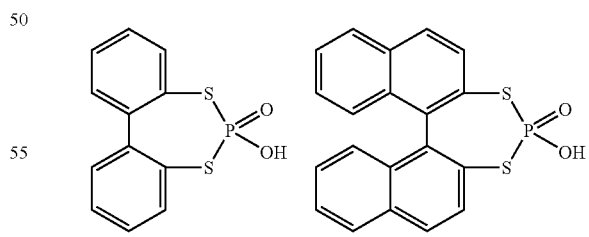
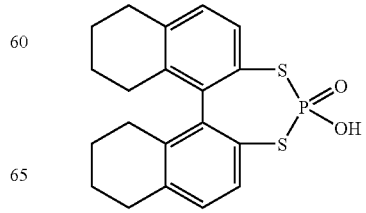
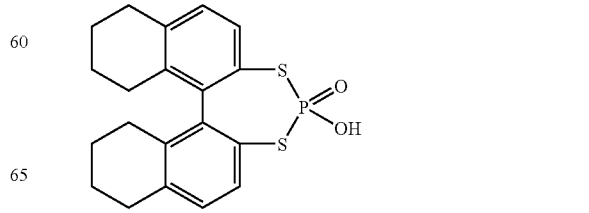

-continued
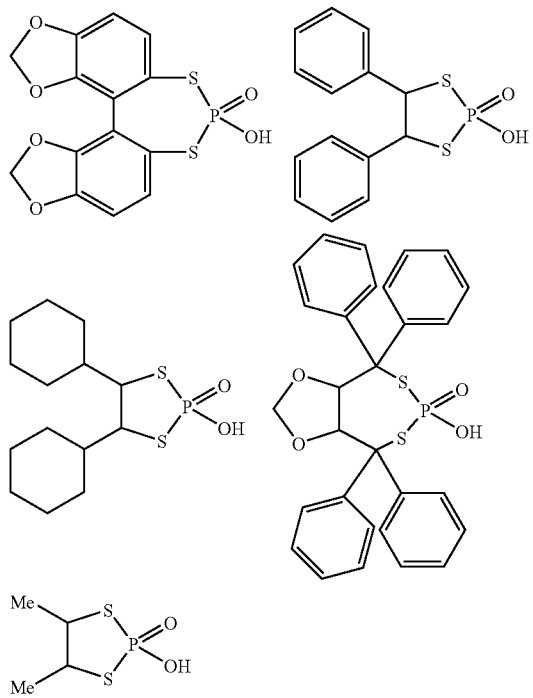
Exemplified Compound 1-12:
-continued
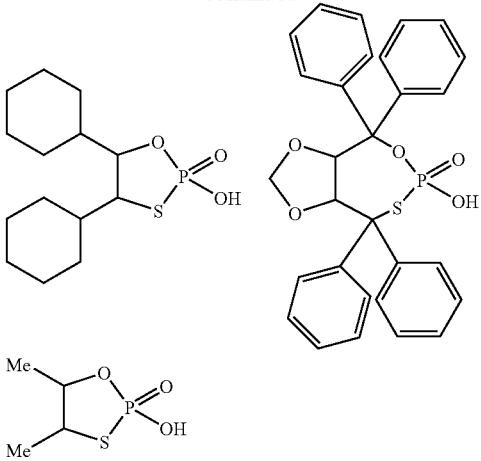
Exemplified Compound 1-13:
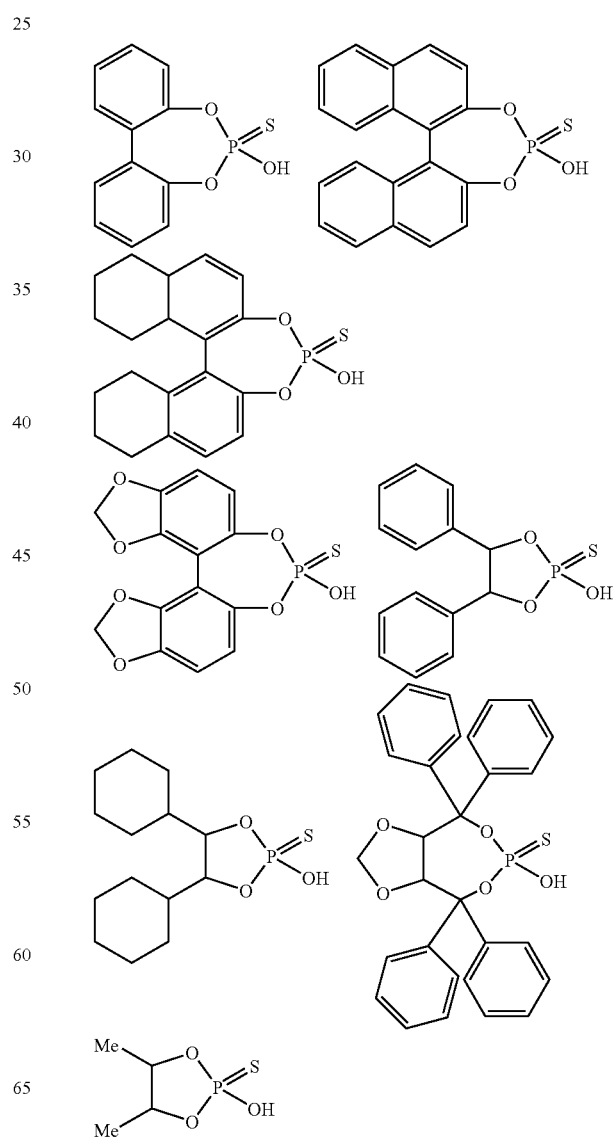

Exemplified Compound 1-14:
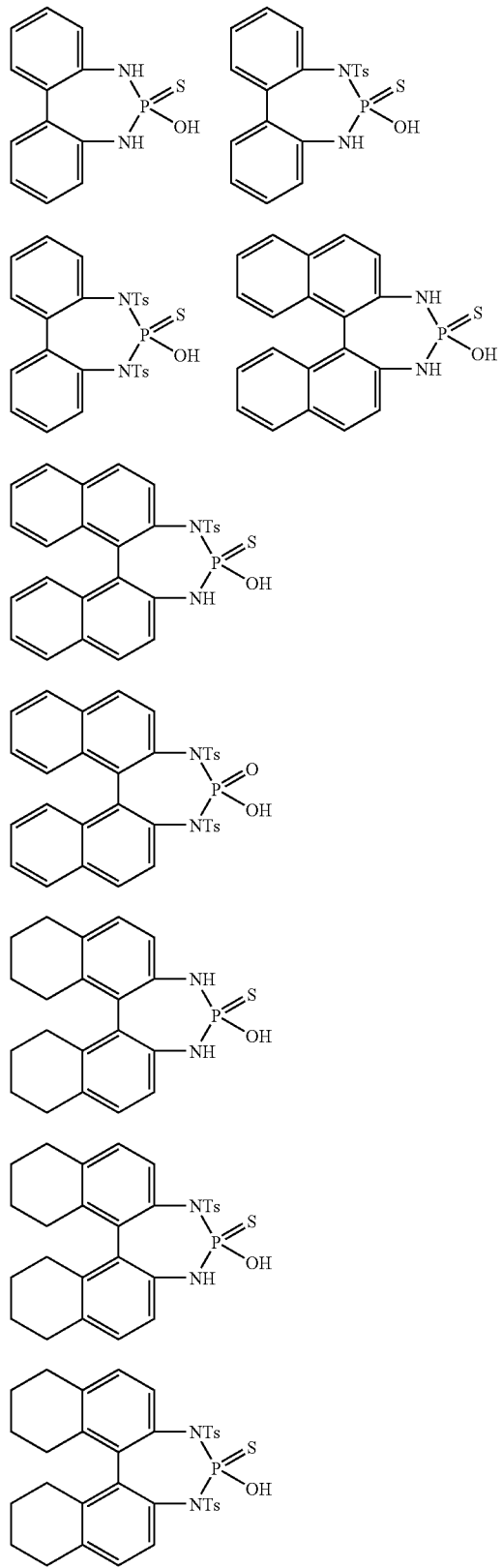
Exemplified Compound 1-15:
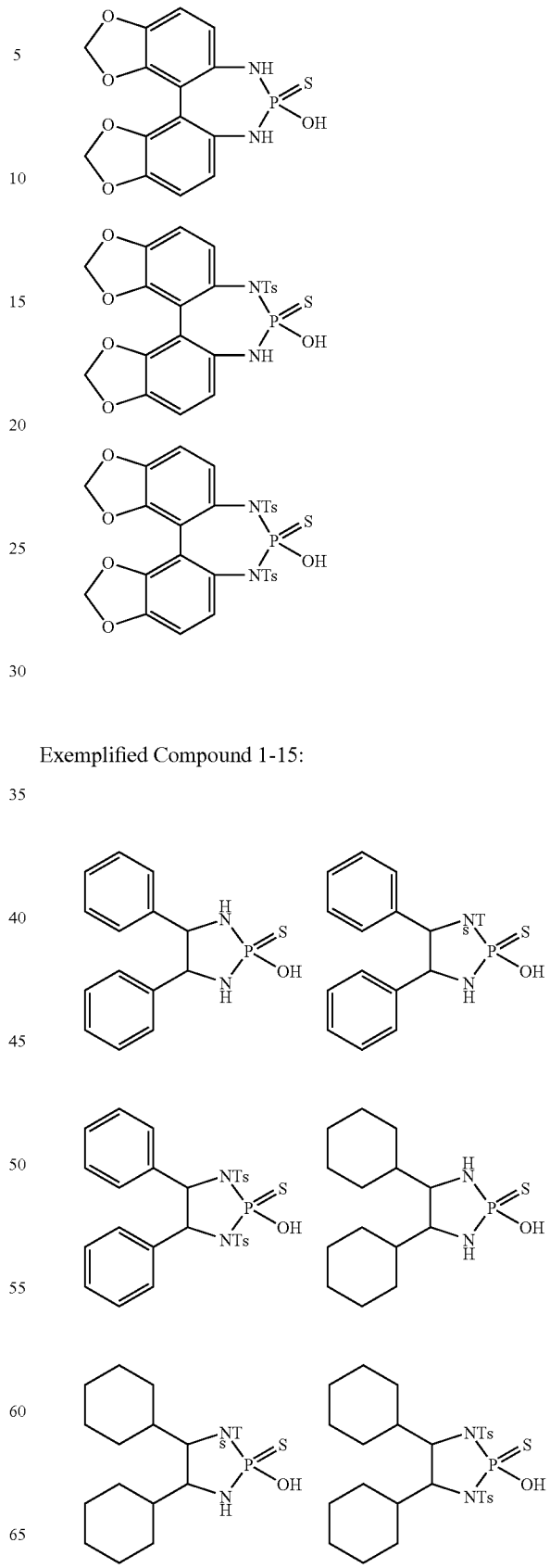

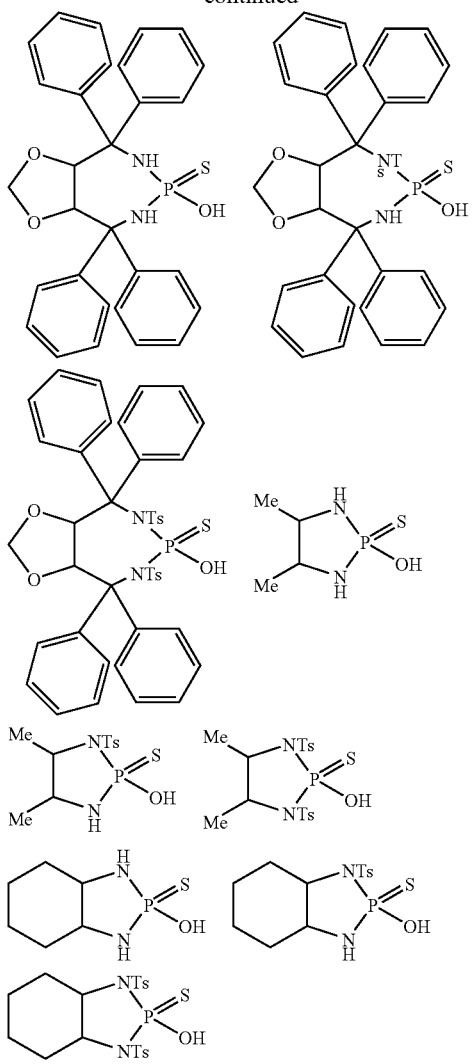

Exemplified Compound 1-16:

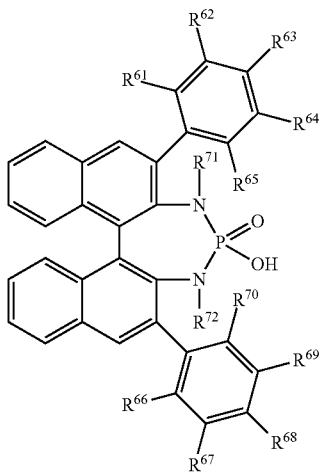

R$^{61}$-R$^{70}$: H, Me, Et, Pr, iPr, Bu, tBu, CF$_3$, Ph, Tolyl, α-Naphtyl, β-Naphtyl, Mesityl, etc.
R$^{71}$, R$^{72}$: H. Ts. Ms, etc.

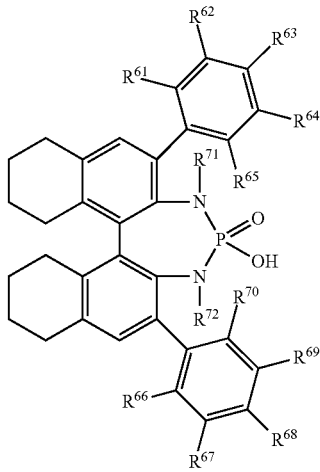

R$^{61}$-R$^{70}$: H, Me, Et, Pr, iPr, Bu, tBu, CF$_3$, Ph, Tolyl, α-Naphtyl, β-Naphtyl, Mesityl, etc.
R$^{71}$, R$^{72}$: H. Ts. Ms, etc.

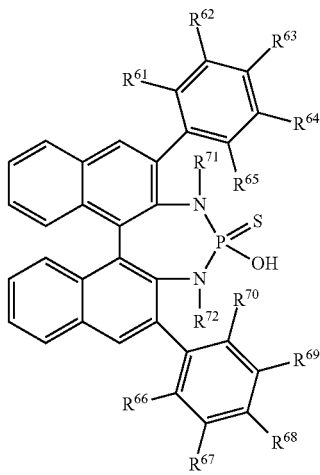

R$^{61}$-R$^{70}$: H, Me, Et, Pr, iPr, Bu, tBu, CF$_3$, Ph, Tolyl, α-Naphtyl, β-Naphtyl, Mesityl, etc.
R$^{71}$, R$^{72}$: H. Ts. Ms, etc.

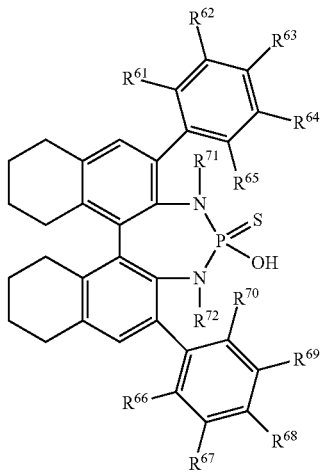

R$^{61}$-R$^{70}$: H, Me, Et, Pr, iPr, Bu, tBu, CF$_3$, Ph, Tolyl, α-Naphtyl, β-Naphtyl, Mesityl, etc.
R$^{71}$, R$^{72}$: H. Ts. Ms, etc.

These phosphoric acid derivatives represented by the formula (1) and the like used in the present invention include phosphoric acid derivatives in which —OH of the phosphoric acid moiety is a metal salt or an ammonium salt.

The metal salt includes salts of an alkali metal such as lithium, sodium, potassium, rubidium, caesium and the like, an alkali earth metal such as magnesium, calcium, strontium, barium and the like, and the like.

The ammonium salt includes salts of ammonia, aliphatic amines such as, for example, methylamine, ethylamine, propylamine, butylamine, cyclohexylamine, dimethylamine, diethylamine, diisopropylamine, triethylamine, tripropylamine, diisopropylethylamine, di(2-ethylhexyl)amine, hexadecylamine, tri-n-butylamine, N-methylmorpholine and the like, aromatic amines such as, for example, N,N-dimethylaniline, pyridine, 4-dimethylaminopyridine and the like, saturated heterocyclic amines such as, for example, piperidine and the like, and the like.

In the process of the present invention, when an optically active compound is prepared, the phosphoric acid derivative represented by the formula (1) is preferably an optically active phosphoric acid derivative represented by the formula (1-1):

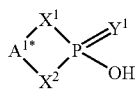

(1-1)

(wherein $A^1$ represents a spacer having an optically active site, and $X^1$, $X^2$ and $Y^1$ are the same as defined above).

In the formula (1-1), the spacer having an optically active site represented by $A^{1*}$ includes a spacer having an optically active site among the spacers represented by $A^1$ in the above-mentioned formula (1).

Specific examples of the optically active phosphoric acid derivative represented by the above-mentioned formula (1-1) include a compound which is optically active form among the phosphoric acid derivatives exemplified as a specific example of the phosphoric acid derivative represented by the above-mentioned formula (1). Representative examples of the optically active phosphoric acid derivative represented by the formula (1-1) include, for example, compounds represented by the following formulae:

Exemplified Compound 1-1-1:

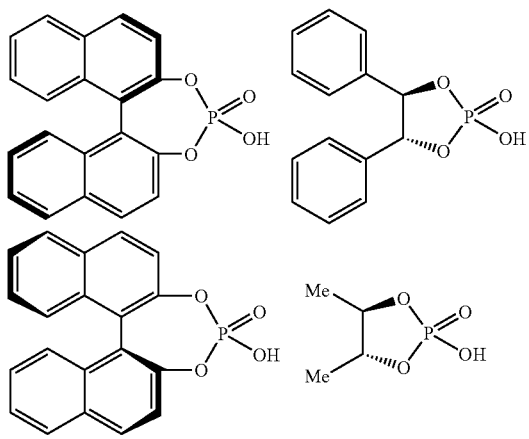

Exemplified Compound 1-1-2:

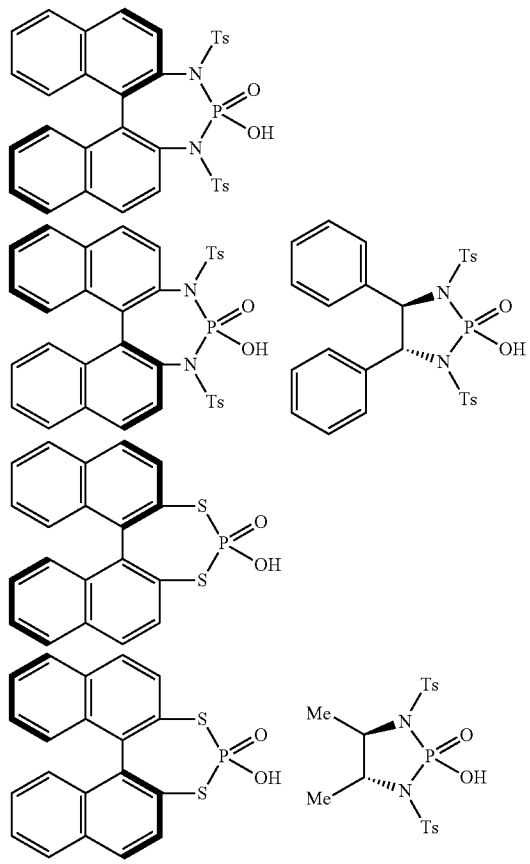

Exemplified Compound 1-1-3:

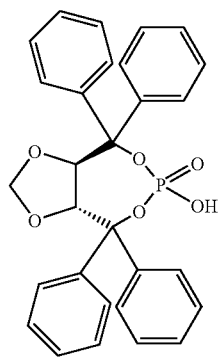

The phosphoric acid derivative represented by the formula (1) is preferably a phosphoric acid derivative represented by the above-mentioned formula (1a):

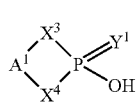

(1a)

(wherein $A^1$ represents a spacer; $X^3$ and $X^4$ each independently represent an oxygen atom, $-NR^{13}-$ ($R^{13}$ represents a hydrogen atom, a hydrocarbon group optionally having substituent (s) or an acyl group optionally having substituent(s)), a sulfur atom or —CR$^{15}$R$^{16}$— {R$^{15}$ and R$^{16}$ each independently represent a hydrogen atom, a hydrocarbon group optionally having substituent(s) or EWG$^3$ (EWG$^3$ represents an electron-withdrawing group), provided that either one of R$^5$ and R$^6$ is EWG$^3$}, and Y$^1$ represents an oxygen atom or a sulfur atom; provided that when i) X$^3$=X$^4$, then X$^3$ and X$^4$ are —NR$^{13}$— (R$^{13}$ represents a hydrogen atom, a hydrocarbon group optionally having substituent(s) or an acyl group optionally having substituent(s)), a sulfur atom or —CR$^{15}$R$^{16}$— and, when X$^3$ and X$^4$ are —NR$^{13}$—, then the —NR$^{13}$— is —NR$^a$— (R$^a$ represents an acyl group derived from sulfonic acid), and that when ii) X$^3$ and X$^4$ are different, either one of X$^3$ and X$^4$ is —NR$^{13}$—, and the —NR— is —NR$^a$— (R$^a$ represents an acyl group derived from sulfonic acid), and the other is an oxygen atom, —NR$^{13}$— (R$^{13}$ represents a hydrogen atom, a hydrocarbon group optionally having substituent(s) or an acyl group optionally having substituent(s)), a sulfur atom or —CR$^{15}$R$^{16}$—), a phosphoric acid derivative represented by the formula (1b):

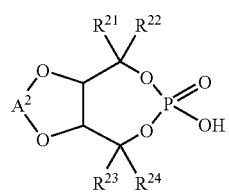

(1b)

(wherein A$^2$ represents a spacer; and R$^{21}$ to R$^{24}$ each independently represent a hydrocarbon group optionally having substituent (s) or a heterocyclic group having substituent(s)), and the like.

Also, examples of the phosphoric acid derivative of the formula (1) include a novel phosphoric acid derivative represented by the following formula (11):

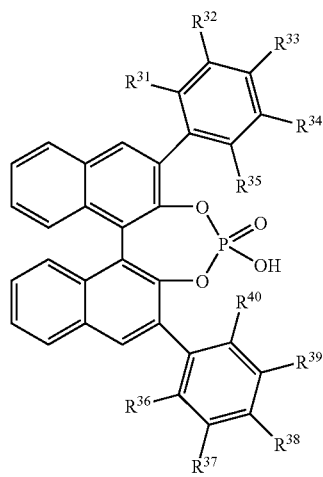

(11)

(wherein R$^{31}$ to R$^{40}$ each independently represent a substituent other than an alkyl-substituted phenyl group, provided that at least one of R$^{31}$ to R$^{35}$ and at least one of R$^{36}$ to R$^{40}$ are an aryl group optionally having substituent(s) (provided that alkyl-substituted phenyl group is excluded)).

Specific examples of the phosphoric acid derivative represented by the above-mentioned formula (11) include, for example, the following compounds:

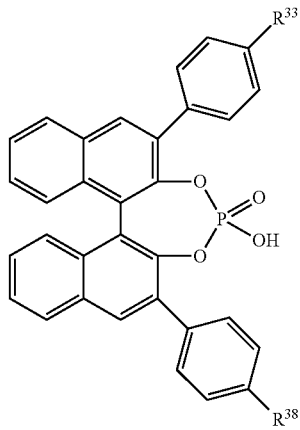

R$^{33}$, R$^{38}$: Ph, α-Naphtyl, β-Naphtyl etc., and

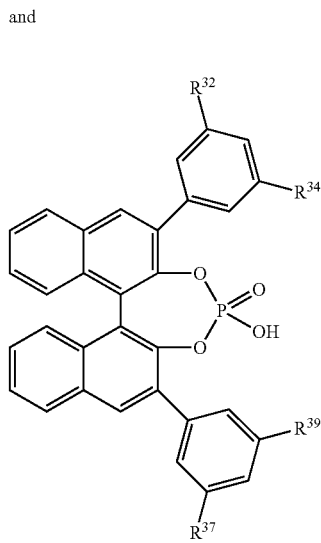

R$^{32}$, R$^{34}$, R$^{37}$, R$^{39}$: Ph, α-Naphtyl, β-Naphtyl etc.

In addition, representative examples of the phosphoric acid derivative of the formula (1) also include the formula (11'):

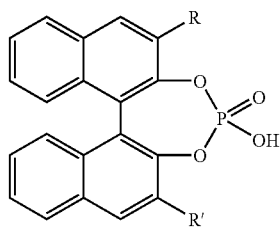

(11')

(wherein R and R' the same or different represent a hydrogen atom, a bromine atom, an iodine atom, a methoxy group, a triphenylsilyl group, a naphthyl group, a phenyl group, or a phenyl group having 1 to 3 substituent(s) (wherein the substituent is a substituent selected from a fluorine atom, a methoxy group, a methyl group, a tert-butyl group, a phenyl group, a trifluoromethyl group, and a naphthyl group).

Specific examples of the phosphoric acid derivative of the formula (11') include corresponding derivatives among compounds exemplified in the Exemplified compound 1-1, and compounds exemplified in the Exemplified compounds 1-3 and 1-16.

In the formula (1a), $X^3$ and $X^4$ each independently represent an oxygen atom, $-NR^{13}-$ ($R^{13}$ represents a hydrogen atom, a hydrocarbon group optionally having substituent(s) or an acyl group optionally having substituent(s)), a sulfur atom or $-CR^{15}R^{16}-$ {$R^{15}$ and $R^{16}$ each independently represent a hydrogen atom, a hydrocarbon group optionally having substituent(s) or $EWG^3$ ($EWG^3$ represents an electron-withdrawing group), provided that either one of $R^{15}$ and $R^{16}$ is $EWG^3$}, and $Y^1$ represents an oxygen atom or a sulfur atom. Provided that, i) when $X^3=X^4$, then $X^3$ and $X^4$ are $-NR^{13}-$ ($R^{13}$ represents a hydrogen atom, a hydrocarbon group optionally having substituent(s) or an acyl group optionally having substituent(s)), a sulfur atom or $-CR^{15}R^{16}-$ and when $X^3$ and $X^4$ are $-NR^{13}-$, then said $-NR^{13}-$ is $-NR^a-$ ($R^a$ represents an acyl group derived from sulfonic acid), and, ii) when $X^3$ and $X^4$ are different, then either one of $X^3$ and $X^4$ is $-NR^{13}-$, and said $-NR^{13}-$ is $-NR^a-$ ($R^a$ represents an acyl group derived from sulfonic acid), and the other is an oxygen atom, $-NR^{13}-$ ($R^{13}$ represents a hydrogen atom, a hydrocarbon group optionally having substituent(s) or an acyl group optionally having substituent(s)), a sulfur atom or $-CR^{15}R^{16}$.

The acyl group derived from sulfonic acid represented by $R^a$ may be the same as the acyl group derived from sulfonic acid explained in the acyl group optionally having substituent(s) explained in a protective group of $R^1$ in the above-mentioned formula (2).

Specific examples of the phosphoric acid derivative represented by the formula (1a) include, for example, compounds exemplified in the above-mentioned Exemplified compounds 1-4 to 1-15 and the like.

Specific examples of the phosphoric acid derivative represented by the formula (1b) include the compounds exemplified in the above-mentioned Exemplified compound 1-2.

The above-mentioned phosphoric acid derivatives represented by the formula (1a) and the formula (1b) is preferably an optically active phosphoric acid derivative represented by the formula (1a-1):

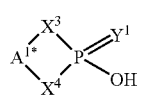

(1a-1)

(wherein $A^{1*}$, $X^3$, $X^4$ and $Y^1$ are the same as defined above, provided that when $X^3$ is $-NR^{13}-$, then $R^{13}$ in the $NR^{13}$ and $A^{1*}$ are not taken together to form a ring), and an optically active phosphoric acid derivative represented by the formula (1b-1):

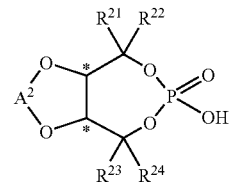

(1b-1)

(wherein $A^{2*}$ represents a spacer having an optically active site, and $R^{21}$ to $R^{24}$ are the same as defined above).

Specific examples of the phosphoric acid derivative represented by the formula (1a-1) include, for example, compounds which are an optically active form among the phosphoric acid derivatives exemplified in the above-mentioned Exemplified compounds 1-4 to 1-15. Representative examples of the optically active phosphoric acid derivative represented by the above-mentioned formula (1a-1) include, for example, a compound represented by the above-mentioned Exemplified compound 1-1-2.

Specific examples of the phosphoric acid derivative represented by the formula (1b-1) include, for example, compounds which are an optically active form among the phosphoric acid derivatives exemplified in the above-mentioned Exemplified compound 1-2. Representative examples of the optically active phosphoric acid derivative represented by the above-mentioned formula (1b-1) include, for example, the compound represented by above-mentioned Exemplified compound 1-1-3.

The phosphoric acid derivative represented by the formula (11) is preferably an optically active phosphoric acid derivative. Said optically active phosphoric acid derivative is represented, for example, by the formula (11a):

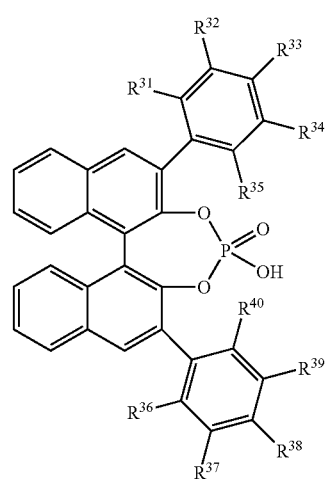

(11a)

wherein $R^{31}$ to $R^{40}$ each independently represent a substituent, provided that at least one of $R^{31}$ to $R^{35}$ and at least one of $R^{36}$ to $R^{40}$ are an aryl group optionally having substituent(s).

In addition, it is preferable to use the phosphoric acid derivative represented by the formula (11') which is optically active.

Specific examples of the phosphoric acid derivative represented by the formula (31) include, for example, phosphoric acid derivatives represented by the following formula (32), (33) and the like:

(32)

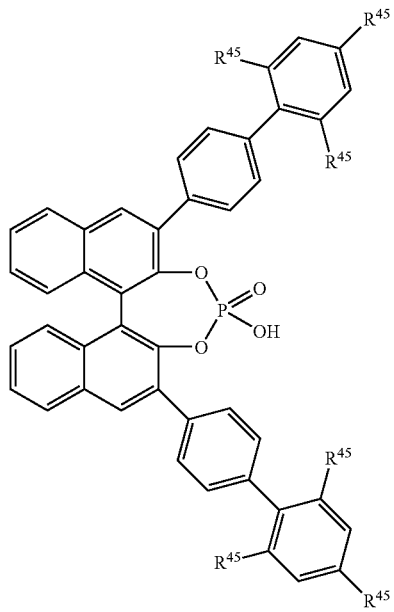

(wherein $R^{45}$ represents an alkyl group) and (33)

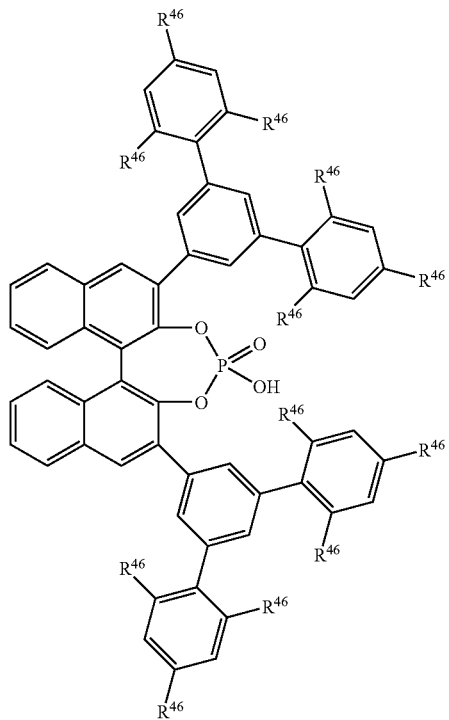

wherein $R^{46}$ represents an alkyl group.

Specific examples of the phosphoric acid derivative represented by the formula (32) include, for example, the following phosphoric acid derivative:

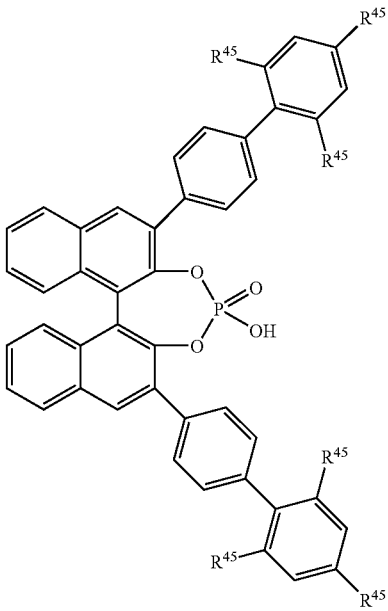

$R^{45}$: $CH_3$, $C_2H_5$, $C_3H_7$, $C_4H_9$, $C_5H_{11}$, $C_6H_{13}$, etc.

Specific examples of the phosphoric acid derivative represented by the formula (33) include, for example, the following phosphoric acid derivative:

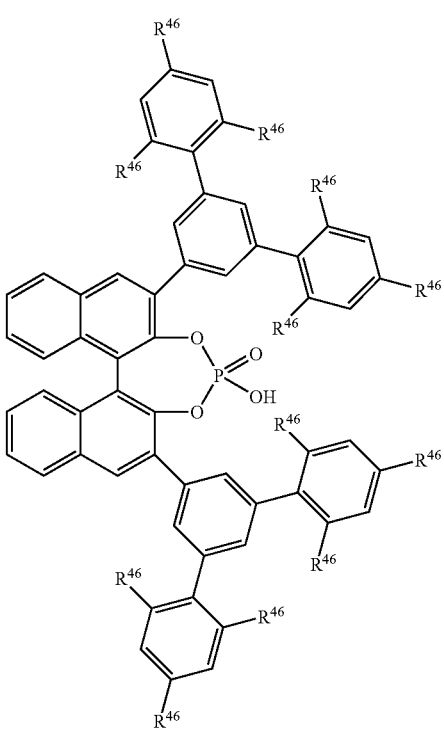

$R^{46}$: $CH_3$, $C_2H_5$, $C_3H_7$, $C_4H_9$, $C_5H_{11}$, $C_6H_{13}$, etc.

The phosphoric acid derivative represented by the formula (31) is preferably an optically active phosphoric acid derivative. Said optically active phosphoric derivative includes, for example, a phosphoric acid derivative represented by the formulae (31a) or (31b):

cally active phosphoric acid derivatives includes the following formulae (32a), (32b), (33a) and (33b), respectively.

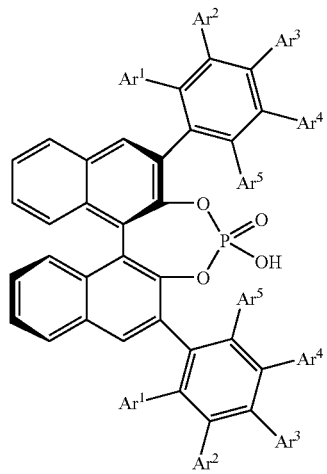

(31a)

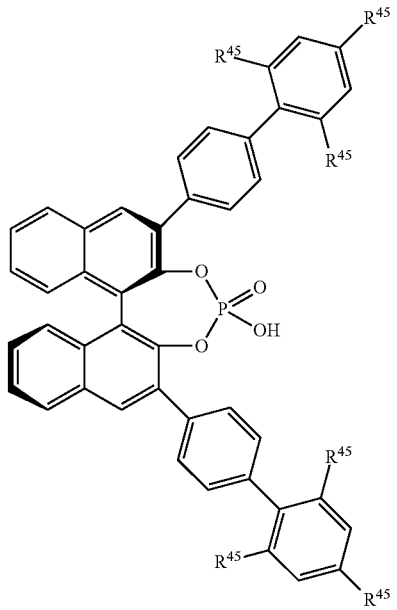

(32a)

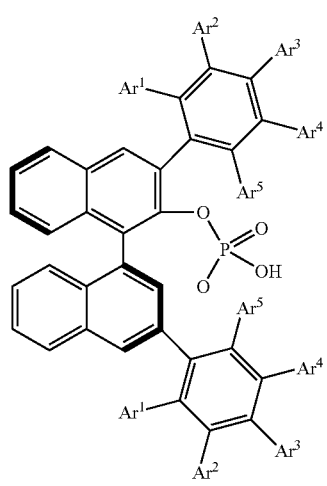

(31b)

(wherein $Ar^1$ to $Ar^5$ are the same as defined above).

The phosphoric acid derivative represented by the above-mentioned formula (32) and the phosphoric acid derivative represented by the above-mentioned formula (33) are preferably an optically active phosphoric acid derivative. Said opti-

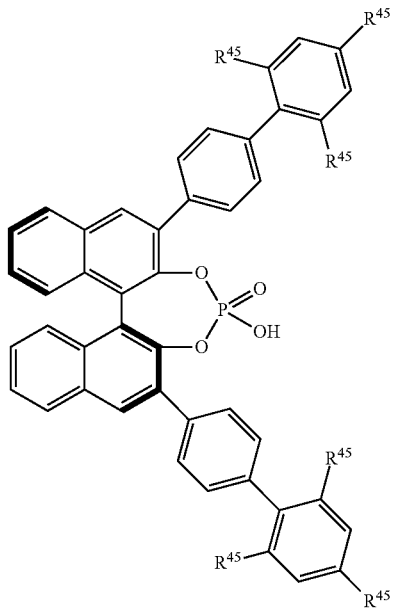

(32b)

(wherein $R^{45}$ is the same as defined above)

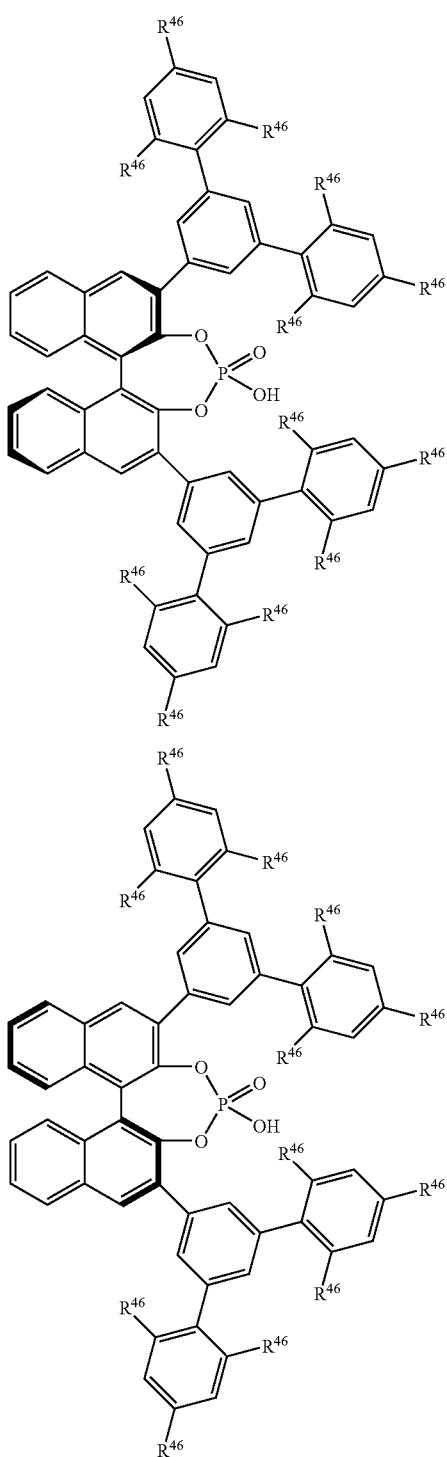

(wherein $R^{46}$ is the same as defined above).

Specific examples of these optically active phosphoric acid derivatives include a respective optically active form of the phosphoric acid derivatives exemplified above.

The phosphoric acid derivative represented by the formula (1) can be produced, for example, as follows:

For example, the phosphoric acid derivative represented by the above-mentioned formula (1) can be obtained by reacting a compound represented by the formula (10):

$$H-X^1-A^1-X^2-H \tag{10}$$

(wherein $A^1$, $X^1$ and $X^2$ are the same as defined above) with a phosphorylating agent.

The compound represented by the formula (10) includes, for example, diols, aminoalcohols, diamines, dithiols, mercaptoalcohols, mercaptoamines and the like.

The diols include, for example, a diol represented by the formula (10-1):

$$HO-A^1-OH \tag{10-1}$$

(wherein $A^1$ is the same as defined above).

Specific examples of the diols include ethylene glycol, propylene glycol, catechol, 1,2-cyclohexanediol, 1,2-diphenylethylene glycol, 2,2'-dihydroxybiphenyl, 1,1'-bi-2-naphthol, 5,5',6,6',7,7',8,8'-octahydro(1,1-binaphthalene)-2,2'-diol and the like.

The aminoalcohols include, for example, an aminoalcohol represented by the formula (10-2):

$$HO-A^1-NHR^{z1} \tag{10-2}$$

(wherein $R^{z1}$ represents a hydrogen atom, a hydrocarbon group optionally having substituent(s) or an acyl group optionally having substituent(s), and $A^1$ is the same as defined above).

The hydrocarbon group optionally having substituent(s) and the acyl group optionally having substituent(s) represented by the aforementioned $R^{z1}$, and after-mentioned $R^{z2}$ to $R^{z4}$ may be the same as respective groups explained in $R^{13}$ in the $-NR^{13}$.

Specific examples of the aminoalcohols include 2-aminoethanol, 1-amino-2-propanol, o-aminophenol, 1-amino-1,2-diphenylethyl alcohol, 2-amino-2'-hydroxybiphenyl, 2-amino-2'-hydroxybinaphthyl, 2-(N-(4-toluenesulfonyl)amino)-2'-hydroxybiphenyl, 2-(N-(4-toluenesulfonyl)amino)-2'-hydroxybinaphthyl and the like.

The diamines include, for example, a diamine represented by the formula (10-3):

$$R^{z2}HN-A^1-NHR^{z3} \tag{10-3}$$

(wherein $R^{z2}$ and $R^{z3}$ each independently represent a hydrogen atom, a hydrocarbon group optionally having substituent (s) or an acyl group optionally having substituent(s), and $A^1$ is the same as defined above).

Specific examples of the diamines include N-unsubstituted diamines such as ethylenediamine, 1,2-diaminocyclohexane, 1,2-dicyclohexylethylenediamine, 1,2-phenylenediamine, 2,2'-diaminobinaphthyl, 1,2-diphenylethylenediamine, 1,2-dinaphthylethylenediamine and the like; N-mono-substituted diamines such as
N-benzenesulfonyl-1,2-phenylenediamine,
N-methanesulfonyl-1,2-phenylenediamine,
N-(4-toluenesulfonyl)-1,2-phenylenediamine,
N-benzenesulfonyl-1,2-diphenylethylenediamine,
N-methanesulfonyl-1,2-diphenylethylenediamine,
N-(4-toluenesulfonyl)-1,2-diphenylethylenediamine and the like; N-di-substituted-diamines such as
N,N'-dibenzenesulfonyl-1,2-phenylenediamine,
N,N'-dimethanesulfonyl-1,2-phenylenediamine,
N,N'-di(4-toluenesulfonyl)-1,2-phenylenediamine,
N,N'-dibenzenesulfonyl-1,2-diphenylethylenediamine,
N,N'-dimethanesulfonyl-1,2-diphenylethylenediamine,
N,N'-di(4-toluenesulfonyl)-1,2-diphenylethylenediamine,
N,N'-dibenzenasulfonyl-1,2-dicyclohexylethylenediamine, N,N'-dimethanesulfonyl-1,2-dicyclohexylethylenediamine,
N,N'-di(4-toluenesulfonyl)-1,2-dicyclohexylethylenediamine,
2,2-di(N,N'-dibenzenesulfonyl)aminobinaphthyl,
2,2-di(N,N'-dimethanesulfonyl)aminobinaphthyl,
2,2-di(N,N'-di(4-toluenesulfonyl))aminobinaphthyl and the like, and the like.

The dithiols include, for example, a dithiol represented by the formula (10-4):

HS-A$^1$-SH  (10-4)

(wherein A$^1$ is the same as defined above).

Specific examples of the dithiols include ethanedithiol, 1,2-propanedithiol and the like.

The mercaptoalcohols include, for example, a mercaptoalcohol represented by the formula (10-5):

HS-A$^1$-OH  (10-5)

(wherein A$^1$ is the same as defined above).

Specific examples of the mercaptoalcohols include 2-mercaptoethanols, 2-hydroxythiophenol and the like.

The mercaptoamines include, for example, a mercaptoamine represented by the formula (10-6):

HS-A$^1$-NHR$^{z4}$  (10-6)

(wherein R$^{z4}$ represents a hydrogen atom, a hydrocarbon group optionally having substituent(s) or an acyl group optionally having substituent(s), and A$^1$ is the same as defined above).

Specific examples of the mercaptoamines include 2-aminothiophenol, 2-(N-(4-toluenesulfonyl)amino)thiophenol and the like.

These compounds represented by the formula (10) are preferably an optically active compound represented by the formula (10a):

H—X$^1$-A$^{1*}$-X$^2$—H  (10a)

(wherein A$^{1*}$, X$^1$ and X$^2$ are the same as defined above) to be used in order to obtain the optically active phosphoric acid derivative represented by the above-mentioned formula (1-1) as compounds represented by the above-mentioned formula (1). In addition, the compounds represented by the formulae (10-1) to (10-6) are also the same.

The optically active compound represented by the above-mentioned formula (10a) includes any optically active compounds as far as it is an optically active form among compounds, such as diols, aminoalcohols, diamines, dithiols, mercaptoalcohols, mercaptoamines and the like, exemplified as the compound represented by the above-mentioned formula (10). The optically active compound represented by the formula (10a) are exemplified the diols, the aminoalcohols and the diamines as representative examples, and specific example thereof include optically active diols such as
(1R,2R)-1,2-cyclohexanediol, (1R,2S)-1,2-cyclohexanediol,
(1S,2R)-1,2-cyclohexanediol, (1S,2S)-1,2-cyclohexanediol,
(1R,2R)-1,2-diphenylethylene glycol,
(1R,2S)-1,2-diphenylethylene glycol,
(1S,2R)-1,2-diphenylethylene glycol,
(1S,2S)-1,2-diphenylethylene glycol, 2,2'-dihydroxybiphenyl,
(R)-1,1'-2-naphthol, (S)-1,1'-bi-2-naphthol,
(R)-5,5',6,6',7,7',8,8'-octahydro-(1,1-binapathalene)-2,2'-diol,
(S)-5,5',6,6',7,7',8,8'-octahydro(1,1-binaphthalene)-2,2'-diol
and the like; optically active aminoalcohols such as
(1R,2R)-1-amino-1,2-diphenylethyl alcohol,
(1R,2S)-1-amino-1,2-diphenylethyl alcohol,
(1S,2R)-1-amino-1,2-diphenylethyl alcohol,
(1S,2S)-1-amino-1,2-diphenylethyl alcohol and the like;
optically active diamines such as
(1R,2R)-1,2-diaminocyclohexane,
(1R,2S)-1,2-diaminocyclohexane,
(1S,2R)-1,2-diaminocyclohexane,
(1S,2S)-1,2-diaminocyclohexane,
(1R,2R)-1,2-dicyclohexylethylenediamine,
(1R,2S)-1,2-dicyclohexylethylenediamine,
(1S,2R)-1,2-dicyclohexylethylenediamine,
(1S,2S)-1,2-dicyclohexylethylenediamine,
(R)-2,2'-diamino-1,1'-binaphthyl,
(S)-2,2'-diamine-1,1'-binaphythyl,
(1R,2R)-1,2-diphenylethylenediamine,
(1R,2S)-1,2-diphenylethylenediamine,
(1S,2R)-1,2-diphenylethylenediamine,
(1S,2S)-1,2-diphenylethylenediamine,
(1R,2R)—N-(4-toluenesulfonyl)-1,2-phenylenediamine,
(1R,2S)—N-(4-toluenesulfonyl)-1,2-phenylenediamine,
(1S,2R)—N-(4-toluenesulfonyl)-1,2-phenylenediamine,
(1S,2S)—N-(4-toluenesulfonyl)-1,2-phenylenediamine,
(1R,2R)—N,N'-di(4-toluenesulfonyl)-1,2-diphenylethylenediamine,
(1R,2S)—N,N'-di(4-toluenesulfonyl)-1,2-diphenylethylenediamine,
(1S,2R)—N,N'-di(4-toluenesulfonyl)-1,2-diphenylethylenediamine,
(1S,2S)—N,N'-di(4-toluenesulfonyl)-1,2-diphenylethylenediamine,
(R)-2,2-di(N,N'-di(4-toluenesulfonyl))aminodinaphthyl,
(S)-2,2-di(N,N'-di(4-toluenesulfonyl))aminodinaphothyl
and the like; and the like.

These compounds represented by the above-mentioned formula (10) may be used commercially available products and compounds appropriately produced. Also, when for example, diamines, aminoalcohols or mercaptoamines are used as the compound represented by the formula (10), a diamine, an aminoalcohol, or a mercaptoamine, wherein the amino group moiety is unsubstituted, is reacted with a phosphorylating agent, and then the hydrocarbon group optionally having substituent(s) and/or the acyl group optionally having substituent(s) may be introduced into the amino group, or the compound represented by the above-mentioned formula (10) wherein a hydrocarbon group optionally having substituent(s) and/or an acyl group optionally having substituent(s) is/are introduced into the amino group moiety may be reacted with a phosphorylating agent.

The phosphorylating agent used in producing the phosphoric acid derivative represented by the formula (1) include phosphorus oxyhalides such as, for example, phosphorus oxychloride, phosphorus oxybromide and the like; phosphorus halides such as, for example, phosphorus (IV) chloride, phosphorus (IV) bromide and the like; dihalogenophosphines such as, for example, dichloroallyloxyphosphine, dichloromethylphosphine and the like; and the like. These phosphorylating agents may be used alone or appropriate in combination of two or more kinds thereof.

Since the amount of the compound represented by the above-mentioned formula (10) and the phosphorylating agent to be used differs depending on the kind of the compound represented by the above-mentioned formula (10) and the phosphorylating agent to be used, they are not particularly limited, but the amount of the phosphorylating agent is appropriately selected from a range of usually about 1.0 to 5.0 equivalent, preferably about 1.5 to 2.5 equivalent relative to the compound represented by the formula (10) as a substrate.

A production of the phosphoric acid derivative may be carried out in the presence of a base, if necessary. The base includes an inorganic base, an organic base and the like. The inorganic base includes potassium carbonate, potassium hydroxide, lithium hydroxide, sodium hydrogen carbonate, sodium carbonate, potassium hydrogen carbonate, sodium hydroxide, magnesium carbonate, calcium carbonate and the like. The organic base includes alkali metal salts/alkaline earth metal salts such as potassium naphthalenide, sodium acetate, potassium acetate, magnesium acetate, calcium acetate and the like; organic amines such as triethylamine, diisopropylethylamine, N,N-dimethylaniline, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine and the like; metal hydrides such as sodium hydride, potassium hydride and the like; organic metal compounds such as methylmagnesium bromide, ethylmagnesium bromide, propylmagnesium bromide, methyllithium, ethyllithium, propyllithium, n-butyllithium, tert-butyllithium and the like; a quaternary ammonium salt; and the like.

Since the amount of the base to be used differs depending on the kind of the compound represented by the formula (10) and the phosphorylating agent to be used, the amount is not particularly limited, but it is appropriately selected from a range of usually 1.0 to 5.0 equivalent, preferably about 1.5 to 2.5 equivalent relative to the predicted equivalent of the generated acid.

A process for producing the phosphoric acid derivative may be carried out in the presence of a solvent, if necessary. The solvent includes, for example, for example, aliphatic hydrocarbons such as pentane, hexane, heptane, octane, decane, cyclohexane and the like; aromatic hydrocarbons such as benzene, toluene, xylene and the like; halogenated hydrocarbons such as dichloromethane, 1,2-dichloroethane, chloroform, carbon tetrachloride, o-dichlorobenzene and the like; ethers such as diethyl ether, diisopropyl ether, tert-butyl methyl ether, dimethoxyethane, ethylene glycol diethyl ether, tetrahydrofuran, 1,4-dioxane, 1,3-dioxolane and the like; ketones such as acetone, methyl ethyl ketone, methyl isobutyl ketone, cyclohexanone and the like; esters such as methyl acetate, ethyl acetate, n-butylacetate, methyl propionate and the like; amides such as formamide, N,N-dimethylformamide, N,N-dimethylacetamide and the like; sulfoxides such as dimethyl sulfoxide and the like; cyano-containing organic compounds such as acetonitrile and the like; N-methylpyrrolidone and the like. These solvents may be used alone or appropriate in combination of two or more kinds thereof.

Since the amount of the solvent to be used differs depending on the kind of the compound represented by the formula (10) and the phosphorylating agent to be used, it is not particularly limited, but may be appropriately selected from a range of usually 0.1 to 1 M, preferably about 0.1 to 0.5 M relative to the compound represented by the formula (10) as a substrate.

Meantime, in the process for producing the phosphoric acid derivatives may be added in addition to the aforementioned base and solvent other component(s), if necessary. Also, the production of the phosphoric acid derivative may be carried out in the base without using the solvent.

The reaction temperature is appropriately selected from a range of usually about −78 to 100° C., preferably about 0 to 50° C.

The reaction time is appropriately selected from a range of usually about 10 minutes to 10 days, preferably about 1 hour to 7 days.

When the dihalogenoallyloxyphosphines are used as a phosphorylating agent, the phosphoric acid derivative represented by the formula (1) can be obtained by producing a phosphoric acid derivative represented by the formula (9):

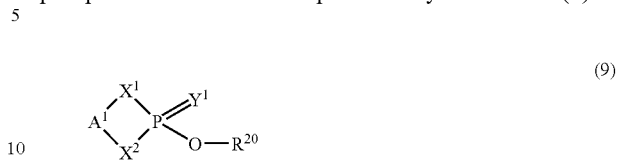

(wherein $R^{20}$ represents an allyl group optionally having substituent(s) or a benzyl group optionally having substituent(s), and $A^1$, $X^1$, $X^2$ and $Y^1$ are the same as defined above), preferably an optically active phosphoric acid derivative represented by the formula (9a):

(wherein $A^{1*}$, $X^1$, $X^2$, $Y^1$ and $R^{20}$ are the same as defined above) as an intermediate, and then reacting said obtained optically active phosphoric acid derivative represented by the formula (9a), optionally in the presence of a transition metal catalyst and optionally in the presence of a nucleophilic agent.

The allyl group optionally having substituent(s) represented by $R^{20}$ includes an allyl group and a substituted allyl group.

The substituted allyl group includes an allyl group in which at least one hydrogen atom of the allyl group is substituted with substituent(s). Said substituent may be the same as the substituent explained in the hydrocarbon group optionally having substituent(s) explained as a protective group of $R^1$ in the above-mentioned formula (2). The substituted allyl group includes, for example, a substituted allyl group having 3 to 20 carbon atoms, and specific examples thereof include croty, prenyl, methallyl, cinnamyl and the like.

The benzyl group optionally having substituent (s) includes a benzyl group and a substituted benzyl group.

The substituted benzyl group includes a benzyl group in which at least one hydrogen atom of the benzyl group is substituted with a substituent. The substituent may be the same as the substituent explained in the hydrocarbon group optionally having substituent(s) explained as a protective group of $R^1$ in the above-mentioned formula (2). The substituted benzyl group includes a substituted benzyl group having 6 to 20 carbon atoms.

Specific examples of the phosphoric acid derivative represented by the formula (9) include, for example, the following compounds:

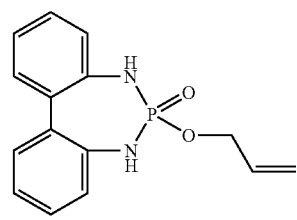

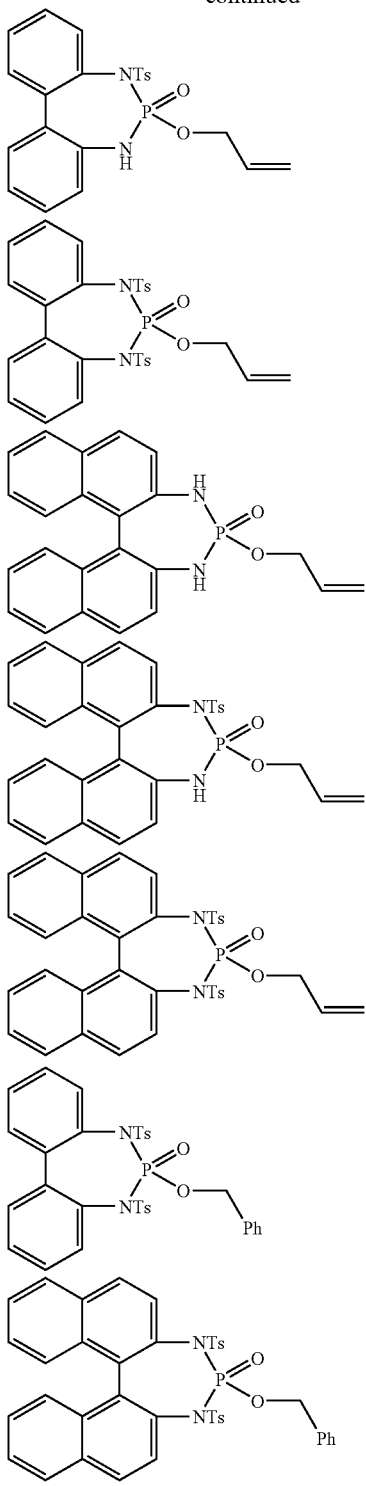

These phosphoric acid derivatives represented by the above-mentioned formula (9) include preferably an optically active phosphoric acid derivative. Specific examples of said optically active phosphoric acid derivative include an optically active form of the phosphoric acid derivative represented by the formula (9) exemplified above.

The transition metal catalyst includes a catalyst of a high periodic transition metal, and examples of the high periodic transition metal includes palladium, platinum, rhodium, nickel, ruthenium, molybdenum and the like.

These transition metal catalysts may be used at any oxidation state of 0 to tetravalent. In such the case, the transition metal catalyst may have various halide ions, hydroxide ion and the like as a counter anion.

Also, these transition metal catalysts may have an appropriate ligand, if necessary. Said ligand includes trivalent phosphorus ligands such as trialkylphosphine, triarylphosphine, trialkyl phosphite and the like, various heterocyclic carbene ligands, amine type ligands, sulfur type ligands and the like. These transition metal catalysts and ligands may be used alone or in appropriate combination with two or more kinds thereof.

Since the amount of the transition metal catalyst to be used differs, depending on the kind of the compound represented by the formula (9) and the transition metal catalyst to be used, it is not particularly limited, but is appropriately selected from a range of usually about 0.0001 to 1.0 equivalent, preferably about 0.01 to 0.1 equivalent relative to the compound represented by the formula (9).

The nucleophilic agent includes carboxylic acids, phenols, ammonium salts, alcohols, and compounds having an active methylene moiety.

Examples of the carboxylic acids include formic acid, acetic acid, propionic acid and the like. The phenols include phenol, catechol and the like. The ammonium salts include ammonium halide salts having at least two hydrogen atoms such as diethylammonium, diisopropylammonium and the like. Examples of the alcohols include methanol, ethanol, 2-propanol, n-butanol, 2-ethoxyethanol, benzylalcohol and the like. The compounds having an active methylene moiety include the compound represented by the above-mentioned formula (3).

As these nucleophilic agents, it may be possible to use an agent which has been prepared in advance or an agent which has been prepared by mixing an acid and a base in a reaction system.

Since the amount of the nucleophilic agent to be used differs depending on the kind of the compound represented by the formula (9) and the transition metal catalyst to be used, it is not particularly limited, but the amount of the nucleophilic agent is appropriately selected from a range of usually about 1.0 to 10.0 equivalents, preferably about 1.2 to 2.5 equivalents relative to the compound represented by the formula (9).

This reaction can be performed in the presence of a base, if necessary. The kind of the base and its amount used are the same as described above.

Also, this reaction may be performed in the presence of a solvent, if necessary. The kind of the solvent is the same as described above.

Since an amount of the solvent to be used differs depending on the kind of the compound represented by the formula (9) and the transition metal catalyst to be used, it is not particularly limited, but is appropriately selected from a range of usually about 0.01 to 10 M, preferably about 0.1 to 0.5 M relative to the compound represented by the formula (9).

Since the reaction temperature is different depending on the kind of the compound represented by the above-mentioned formula (9) and the transition metal catalyst to be used, it is not particularly limited, but is appropriately selected from a range of usually about 0 to 200° C., preferably about 0 to 100° C.

The reaction time is appropriately selected from a range of usually about 10 minutes to 10 days, preferably about 1 hour to 7 days.

The production process of the phosphoric acid derivatives can be carried out optionally in an inert gas atmosphere. The inert gas includes a nitrogen gas, an argon gas and the like.

The obtained phosphoric acid derivative may be used as it is in the process of the present invention, or may be used after post-treatment, purification, isolation or the like as necessary. Specific means of post-treatment, purification, isolation and the like include means known per se such as solvent extraction, liquid nature conversion, dissolution, salting out, crystallization, recrystallization, various chromatographies and the like.

Next, the production process of the present invention will be explained using the following reaction scheme.

1) Reaction of an Imine Compound with a Compound Represented by the Formula (3):

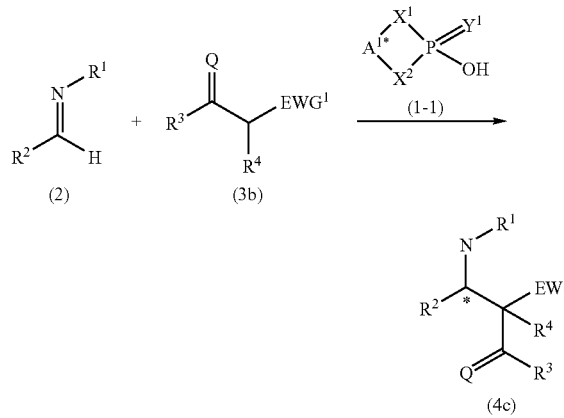

Scheme 1

Scheme 1 is a reaction equation showing a reaction of obtaining an optically active amine represented by the formula (4c) as the amines using an imine compound represented by the formula (2) as the imine compound, using a compound represented by the formula (3b) in which $R^5$ in the compound represented by the formula (3) is $EWG^1$ as the nucleophilic compound, and using the optically active phosphoric acid derivative represented by the formula (1-1) as the phosphoric acid derivative represented by the formula (1), respectively.

That is, the optically active amines represented by the formula (4c) can be obtained by reacting the imine compound represented by the formula (2) with the compound represented by the formula (3b) in the presence of the optically active phosphoric acid derivative represented by the formula (1-1).

Since the amount of each of the imine compound represented by the formula (2) and the compound represented by the formula (3b) to be used differs, depending on the kind of the imine compound represented by the formula (2), the compound represented by the formula (3b), and the optically active phosphoric acid derivative represented by the formula (1-1) to be used, such amount is not particularly limited, but the amount of the compound represented by the formula (3b) is appropriately selected from a range of usually about 0.9 to 2.0 equivalents, preferably about 1.0 to 1.5 equivalents relative to the imine compound represented by the formula (2).

The present production process may be performed optionally in the presence of a solvent. The solvent includes, for example, aliphatic hydrocarbons such as pentane, hexane, heptane, octane, decane, cyclohexane and the like; aromatic hydrocarbons such as benzene, toluene, xylene and the like; halogenated hydrocarbons such as dichloromethane, 1,2-dichloroethane, chloroform, deuterochloroform (chloroform-d), carbon tetrachloride, o-dichlorobenzene and the like; ethers such as diethyl ether, diisopropyl ether, tert-butyl methyl ether, dimethoxyethane, ethylene glycol diethyl ether, tetrahydrofuran, 1,4-dioxane, 1,3-dioxolane and the like; ketones such as acetone, heavy acetone (deuteroacetone), methyl ethyl ketone, methyl isobutyl ketone, cyclohexanone and the like; tertiary alcohols such as tert-butanol and the like; esters such as methyl acetate, ethyl acetate, n-butyl acetate, methyl propionate and the like; amides such as formamide, N,N-dimethylformamide, N,N-dimethylacetamide and the like; sulfoxides such as dimethyl sulfoxide, deuterodimethyl sulfoxide (dimethyl sulfoxide-$d_6$, etc.), cyano-containing organic compounds such as acetonitrile and the like; N-methylpyrrolidone; and the like. These solvents may be used alone or in appropriate combination with two or more solvents thereof.

Since the amount of a solvent when it is used differs depending on the kind of the imine compound represented by the formula (2) and the compound represented by the formula (3b) to be used, such amount is not particularly limited, but the amount of a substrate concentration of the imine compound represented by the formula (2) is appropriately selected from a range of usually about 0.01 to 1 M, preferably about 0.05 to 0.2 M.

The reaction temperature is appropriately selected from a range of usually about −78° C. to 100° C., preferably about 0° C. to 50° C., more preferably a range of around room temperature.

The reaction time is appropriately selected from a range of usually about 10 minutes to 10 days, preferably about 1 hour to 7 days.

2) Reaction of an Imine Compound and a Compound Represented by the Formula (5)

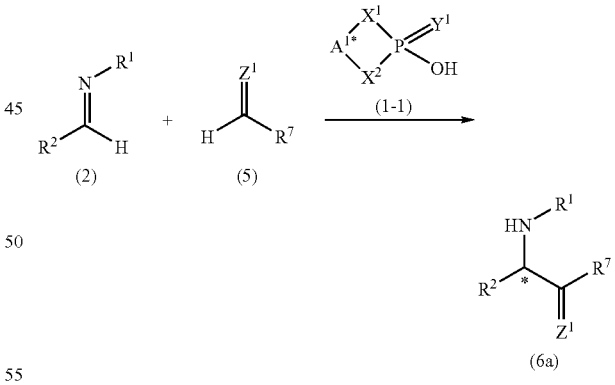

Scheme 2

Scheme 2 is a reaction equation showing a reaction obtaining an optically active amine represented by the formula (6a) as the amine using an imine compound represented by the formula (2) as the imine compound, using a compound represented by the formula (5) as the nucleophilic compound, and using an optically active phosphoric acid derivative represented by the formula (1-1) as the phosphoric acid derivative represented by the formula (1), respectively.

That is, the optically active amine represented by the formula (6a) can be obtained by reacting the imine compound represented by the formula (2) with the compound represented by the formula (5) in the presence of the optically active phosphoric acid derivative represented by the formula (1-1).

Since the amount of the imine compound represented by the formula (2) and the compound represented by the formula (5) to be used differs depending on the kind of the imine compound represented by the formula (2), the compound represented by the formula (5), and the optically active phosphoric acid derivative represented by the formula (1-1), such amount is not particularly limited, but the amount of the compound represented by the formula (5) is appropriately selected from a range of usually about 0.9 to 2.5 equivalents, preferably about 1.0 to 1.5 equivalents relative to the imine compound represented by the formula (2).

The present production process may be performed in the presence of a solvent, if necessary. The solvent includes solvents exemplified in the above scheme 1.

Since the amount of the solvent when it is used differs, depending on kinds of the imine compound represented by the formula (2) and the compound represented by the formula (5) to be used, the amount is not particularly limited, but a substrate concentration of such imine compound represented by the formula (2) is appropriately selected from a range of usually about 0.01 to 1 M, preferably about 0.05 to 0.2 M.

The reaction temperature is appropriately selected from a range of usually about 0° C. to 100° C., preferably about 0° C. to 50° C., more preferably a range of around room temperature.

The reaction time is appropriately selected from a range of usually about 10 minutes to 10 days, preferably about 1 hour to 7 days.

3) Reaction of an Imine Compound and a Compound Represented by the Formula (7)

by the formula (7-1) in the presence of the optically active phosphoric acid derivative represented by the formula (1-1).

Since the amount of each of the imine compound represented by the formula (2) and the compound represented by the formula (7-1) are different, depending on the kind of the imine compound represented by the formula (2), the compound represented by the formula (7-1), and the optically active phosphoric acid derivative represented by the formula (1-1) to be used, such amount is not particularly limited, but the compound represented by the formula (7-1) is appropriately selected from a range of usually about 0.9 to 2.5 equivalents, preferably about 1.0 to 1.5 equivalents relative to the imine compound represented by the formula (2).

The present production process may be performed in the presence of a solvent, if necessary. The solvent includes solvents exemplified in the above scheme 1.

Since the amount of the solvent when it is used differs, depending on the kind of the imine compound represented by the formula (2) and the compound represented by the formula (7-1) to be used, such amount is not particularly limited, but the amount of a substrate concentration of the imine compound represented by the formula (2) is appropriately selected from a range of usually about 0.01 to 1 M, preferably about 0.05 to 0.5 M.

The reaction temperature is appropriately selected from a range of usually about −50° C. to 100° C., preferably about −20° C. to 50° C., more preferably a range of around room temperature.

The reaction time is appropriately selected from a range of usually about 10 minutes to 10 days, preferably about 30 minutes to 7 days.

4) Reaction of an Imine Compound and Benzenes Represented by the Formula (21)

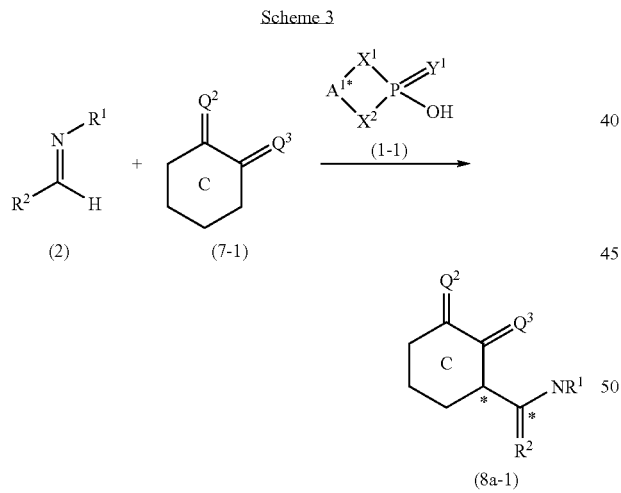

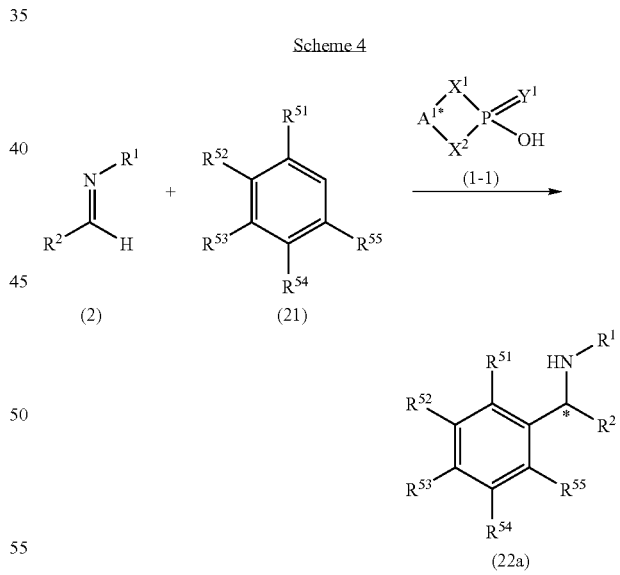

Scheme 3 is a reaction equation showing a reaction of an obtaining optically active amine represented by the formula (8a-1) as the amine using an imine compound represented by the general formula (2) as the imine compound, using a compound represented by the formula (7-1) among the compounds represented by the formula (7) as the nucleophilic compound, and using an optically active phosphoric acid derivative represented by the formula (1-1) as the phosphoric acid derivative represented by the formula (1), respectively.

That is, the optically active amine represented by the formula (8a-1) can be obtained by reacting the imine compound represented by the formula (2) and the compound represented Scheme 4 is a reaction equation showing a reaction of obtaining an optically active amine represented by the formula (22a) as the amine using an imine compound represented by the formula (2) as the imine compound, using a benzene represented by the formula (21) as the nucleophilic compound, and using an optically active phosphoric acid derivative represented by the formula (1-1) as the phosphoric acid derivative, respectively.

That is, an optically active amine represented by the formula (22a) can be obtained by reacting the imine compound represented by the formula (2) and the benzene represented by the formula (21) in the presence of the optically active phosphoric acid derivative represented by the formula (1-1).

Since the amount of each of the imine compound represented by the formula (2) and the benzene represented by the formula (21) to be used differs, depending on the kind of the imine compound represented by the formula (2), the benzene represented by the formula (21), and the optically active phosphoric acid derivative represented by the formula (1-1) to be used, such amount is not particularly limited, but the amount of the benzene represented by the formula (21) is appropriately selected from a range of usually about 0.9 to 2.5 equivalents, preferably about 1.0 to 1.5 equivalents relative to the imine compound represented by the formula (2).

The present production process may be performed in the presence of a solvent, if necessary. The solvent includes those exemplified in the above scheme 1.

Since the amount of the solvent when it is used differs, depending on the kind of the imine compound represented by the formula (2) and the benzene represented by the formula (21) to be used, such amount is not particularly limited, but the amount of a substrate concentration of the imine compound represented by the formula (2) is appropriately selected from a range of usually about 0.01 to 1 M, preferably about 0.05 to 0.5 M.

The reaction temperature is appropriately selected from a range of usually about −50° C. to 100° C., preferably about −20° C. to 50° C., more preferably a range of around room temperature.

The reaction time is appropriately selected from a range of usually about 10 minutes to 10 days, preferably about 30 minutes to 7 days.

5) Reaction of an Imine Compound and an Unsaturated Heterocyclic Compound Represented by the Formula (14)

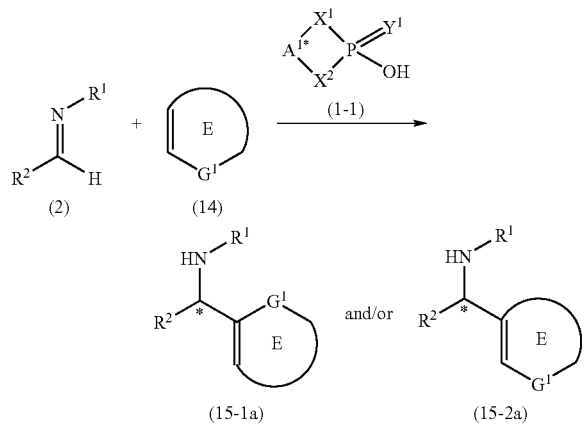

Scheme 5

Scheme 5 is a reaction equation showing a reaction of obtaining an optically active amine represented by the formula (15-1a) and/or an optically active amine represented by the formula (15-2a) as the amines using an imine compound represented by the formula (2) as the imine compound, using an unsaturated heterocyclic compound represented by the formula (14) as the nucleophilic compound, and using an optically active phosphoric acid derivative represented by the formula (1-1) as the optically active phosphoric acid derivative represented by the formula (1), respectively.

That is, the optically active amine represented by the formula (15-1a) and/or the optically active amine represented by the formula (15-2a) can be obtained by reacting the imine compound represented by the formula (2) and the unsaturated heterocyclic compound represented by the formula (14) in the presence of the optically active phosphoric acid derivative represented by the formula (1-1).

Since the amount of the imine compound represented by the formula (2) and the unsaturated heterocyclic compound represented by the formula (14) to be used differs, depending on the kind of the imine compound represented by the formula (2), the unsaturated heterocyclic compound represented by the formula (14) and the optically active phosphoric acid derivative represented by the formula (1-1) to be used, such amount is not particularly limited, but the amount of the unsaturated heterocyclic compound represented by the formula (14) is appropriately selected from a range of usually about 0.9 to 2.5 equivalents, preferably about 1.0 to 1.5 equivalents relative to the imine compound represented by the formula (2).

The present process may be performed in the presence of a solvent, if necessary. The solvent includes those exemplified in the above scheme 1.

Since the amount of the solvent when it is used differs, depending on the kind of the imine compound represented by the formula (2) and the unsaturated heterocyclic compound represented by the formula (14) to be used, such amount is not particularly limited, but the amount of a substrate concentration of the imine compound represented by the formula (2) is appropriately selected from a range of usually about 0.01 to 1 M, preferably about 0.05 to 0.5 M.

The reaction temperature is appropriately selected from a range of usually about −80° C. to 100° C., preferably about −50° C. to 50° C., more preferably a range around about −35° C.

The reaction time is appropriately selected from a range of usually about 10 minutes to 10 days, preferably about 30 minutes to 7 days.

6) Reaction of an Imine Compound and an Unsaturated Heterocyclic Compound Represented by the Formula (16)

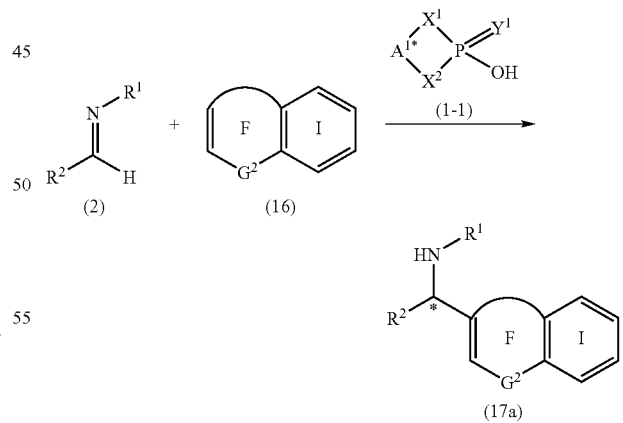

Scheme 6

Scheme 6 is a reaction equation showing a reaction of obtaining an optically active amine represented by the formula (17a) as the amine using an imine compound represented by the formula (2) as the imine compound, using an unsaturated heterocyclic compound represented by the formula (16) as the nucleophilic compound, and using an optically active phosphoric acid derivative represented by the formula (1-1) as the phosphoric acid derivative represented by the formula (1), respectively.

That is, optically active amines represented by the formula (17a) can be obtained by reacting the imine compound represented by the formula (2) with the unsaturated heterocyclic compound represented by the formula (16) in the presence of the optically active phosphoric acid derivative represented by the formula (1-1).

Since the amount of each of the imine compound represented by the formula (2) and the unsaturated heterocyclic compound represented by the formula (16) to be used differs, depending on kinds of the imine compound represented by the formula (2), the unsaturated heterocylic compound represented by the formula (16) and the optically active phosphoric acid derivative represented by the formula (1-2) to be used, such amount is not particularly limited, but the amount of the unsaturated heterocyclic compound represented by the formula (16) is appropriately selected from a range of usually about 0.9 to 2.5 equivalents, preferably about 1.0 to 1.5 equivalents relative to the imine compound represented by the formula (2).

The present process may be performed in the presence of a solvent, if necessary. The solvent includes those exemplified in the scheme 1.

Since the amount of the solvent when it is used differs, depending on the kind of the imine compound represented by the formula (2) and the unsaturated heterocyclic compound represented by the formula (16) to be used, such amount is not particularly limited, but the amount of a substrate concentration of the imine compound represented by the formula (2) is appropriately selected from a range of usually about 0.01 to 1 M, preferably about 0.05 to 0.5 M.

The reaction temperature is appropriately selected from a range of usually about $-80°$ C. to $100°$ C., preferably about $-60°$ C. to room temperature, more preferably a range of around about $-40°$ C.

The reaction time is appropriately selected from a range of about 10 minutes to 10 days, preferably about 30 minutes to 7 days.

7) Reaction of an Imine Compound and a Furan Represented by the Formula (12)

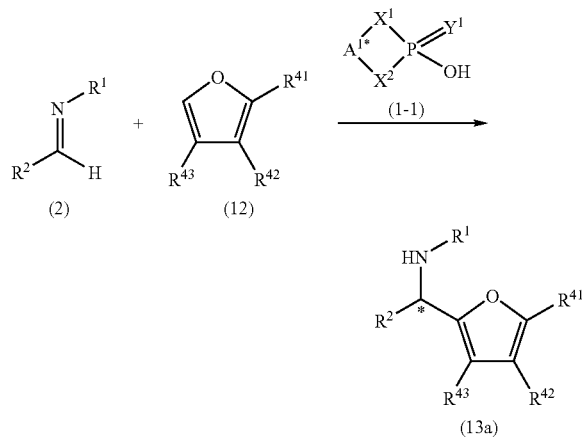

Scheme 7

Scheme 7 is a reaction equation showing a reaction of obtaining an optically active amine represented by the formula (13a) as the amine using an imine compound represented by the formula (2) as the imine compound, using a furan represented by the formula (12) as the nucleophilic compound, and using an optically active phosphoric acid derivative represented by the formula (1-1) as the phosphoric acid derivative represented by the formula (1), respectively.

That is, the optically active amine represented by the formula (13a) can be obtained by reacting the imine compound represented by the formula (2) and the furan represented by the formula (12) in the presence of the optically active phosphoric acid derivative represented by the formula (1-1).

Since the amount of each of the imine compound represented by the formula (2) and the furan represented by the formula (12) are different depending on kinds of the imine compound represented by the formula (2), and the optically active phosphoric acid derivative represented by the formula (1-1) to be used, such amount is not particularly limited, but the amount of the furan represented by the formula (12) is appropriately selected from a range of usually about 0.9 to 5.0 equivalents, preferably about 1.0 to 3.0 equivalents relative to the imine compound represented by the formula (2).

The present process may be performed in the presence of a solvent, if necessary. The solvent includes those exemplified in the scheme 1.

Since the amount of the solvent when it is used differs, depending on the kind of the imine compound represented by the formula (2) and the furan represented by the formula (12) to be used, such amount is not particularly limited, but the amount of a substrate concentration of the imine compound represented by the formula (2) is appropriately selected from a range of usually about 0.01 to 1 M, preferably about 0.05 to 0.5 M.

The reaction temperature is appropriately selected from a range of usually about $-50°$ C. to $100°$ C., preferably about $-20°$ C. to $50°$ C., more preferably a range of around room temperature.

The reaction time is appropriately selected from a range of usually about 10 minutes to 10 days, preferably about 30 minutes to 7 days.

The process of the present invention explained in the schemes 1 to 7 can be performed in an inert gas atmosphere. Examples of the inert gas include a nitrogen gas, an argon gas and the like.

The resulting optically active amines may be subjected to post-treatment, purification, isolation or the like, if necessary.

The thus obtained amines are useful as an intermediate for medicines, agricultural chemicals or the like.

EXAMPLES

The present invention will be explained in detail below by way of Examples and Comparative Examples, but the present invention is not limited at all by them. Respective abbreviations used in Examples mean as follows.

Ac: acetyl
anth: anthryl
BINOL: 1,1'-bi-2-naphthol
Bn: benzene
Boc: tert-butoxycarbonyl
Bs: benzenesulfonyl
Bz: benzyl
$CDCl_3$: heavy chloroform (deuterochloroform)
cHex: cyclohexane
DCE: 1,2-dichloroethane
DCM: dichloromethane
Et: ethyl
$Et_2O$: diethyl ether
t-Bu: tert-butyl
i-Pr: isopropyl i-Pr₂O: diisopropyl ether
Me: methyl
MeCN: acetonitrile
MeO: methoxy
mes: mesityl
Naph: naphthyl
Ph: phenyl
Py: pyridine
t-Bu: tert-butyl
TCE: 1,1,2,2-tetrachloroethane
TES: triethylsilyl
Tf: trifluoromethanesulfonyl
THF: tetrahydrofuran
TMS: trimethylsilyl
tol: tolyl
TPS: triphenylsilyl
Ts: tosyl Example 1

Synthesis of the Following Phosphoric Acid Derivative 1

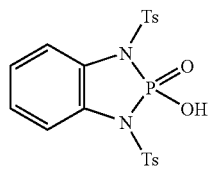

Phosphoric Acid Derivative 1

(1) Synthesis of N,N'-di-p-toluenesulfonyl-1,2-phenylenediamine

To a solution in which 1,2-phenylenediamine (0.5 mmol) was dissolved in pyridine (1 mL) was added p-toluenesulfonyl chloride (1.1 mmol) at room temperature, and the mixture was reacted for 6 hours with stirring. After completion of the reaction, the reaction mixture was diluted with dichloromethane, and back extracted using 1N hydrochloric acid to remove pyridine. After the organic layer was dried with anhydrous sodium sulfate, and concentrated. The obtained solid was washed using diethyl ether on a Buchner funnel, and dried under reduced pressure to obtain an objective substance as a white solid in a yield of more than 95% yield.

(2) Synthesis of Phosphoric Acid Derivative 1

Under nitrogen atmosphere, to a solution in which N,N'-di p-toluenesulfonyl-1,2-phenylenediamine (0.5 mmol) obtained in Example 1(1) was dissolved in pyridine (1 mL) was added dropwise phosphorus oxychloride (0.75 mmol) at room temperature. The mixture was stirred for 12 hours with stirring. After completion of the reaction, water was added thereto, and the mixture was further stirred for 30 minutes. The obtained suspension was diluted with ethyl acetate, and back extracted using 1N hydrochloric acid to remove pyridine. Purification by column chromatography in a conventional method afforded an objective substance as a white solid in more than 90% yield.

¹HNMR (CDCl₃, 270 MHz): δ 2.30 (6H, s), 6.90 (2H, m), 7.22 (4H, d, J=8.5 Hz), 7.35 (2H, m), 8.08 (4H, d, J=8.5 Hz).

Example 2

Synthesis of the Following Optically Active Phosphoric Acid Derivative 2

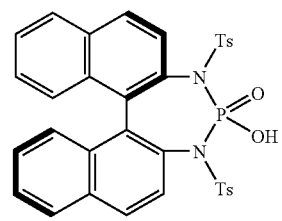

Phosphoric Acid Derivative 2

(1) Synthesis of N,N'-di-p-toluenesulfonyl-1,1'-binaphthyl-2,2'-diamine

Under nitrogen atmosphere, to a solution in which 1,1'-binaphthyl-2,2'-diamine (0.5 mmol) was dissolved in pyridine (1 mL) was added p-toluenesulfonyl chloride (1.1 mmol) at room temperature, and the mixture was reacted for 5 to 12 hours with stirring. After completion of the reaction, the resulting red suspension was diluted with ethyl acetate, and back-extracted with 1N hydrochloric acid to remove pyridine. The resulting organic layer was dried with sodium sulfate to remove the solvent, and the residue was purified by column chromatography to obtain an objective substance as a pale yellow to white solid in more than 95% yield.

(2) Synthesis of the Following Optically Active Phosphoric Acid Ester

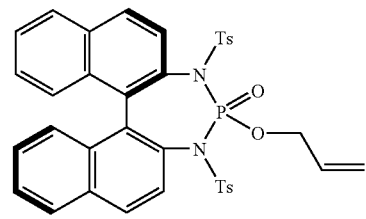

A solution in which N,N'-di-p-toluenesulfonyl-1,1'-binaphthyl-2,2'-diamine (0.1 mmol) obtained in Example 2 (1) was dissolved in anhydrous tetrahydrofuran (5 mL) under nitrogen atmosphere was cooled to 0° C., and to this solution were added dropwise a solution of dichloroallyloxyphosphine in tetrahydrofuran (0.1 M, 2 mL, 0.2 mmol) and triethylamine (0.6 mmol). The mixture was stirred at room temperature for several hours, and cooled to 0° C. again. Then, 3% aqueous hydrogen peroxide (1 mL) was added dropwise thereto to perform the reaction at 0° C. for 1 to 2 hours with stirring. After completion of the reaction, the organic layer was dried, and concentrated, and the resultant solid was purified by column chromatography to obtain an objective substance as a pale yellow to white solid in more than 80% yield.

(3) Synthesis of Optically Active Phosphoric Acid Derivative 2

Optically active phosphoric acid ester (0.1 mmol) obtained in Example 2(2), triphenylphosphine (0.02 mmol) and tetrakistriphenylphosphine palladium (0.005 mmol) were mixed, and anhydrous tetrahydrofuran (1.4 mL) was added thereto under nitrogen atmosphere to obtain a solution, which was then degassed. To this solution were added triethylamine (0.3 mmol) and formic acid (0.3 mmol) at room temperature, and the mixture was made to react for 12 hours with stirring. After completion of the reaction, the obtained suspension was concentrated under reduced pressure, and the obtained solid residue was purified by column chromatography to give an objective substance in more than 80% yield.

$^1$HNMR (CDCl$_3$, 270 MHz): δ 1.84 (6H, s), 6.24 (4H, d, J=8.2 Hz), 6.87 (2H, d, J=8.6 Hz), 7.02 (2H, t, J=7.3 Hz), 7.13 (4H, d, J=8.2 Hz), 7.32 (2H, t, J=7.3 Hz), 7.68 (2H, d, J=8.4 Hz), 7.94 (2H, d, J=8.9 Hz), 8.10 (2H, d, J=8.4 Hz).

Examples 3 to 8

Synthesis of the Following Optically Active Phosphoric Acid Derivatives

According to the same manner as described in Example 2 except that a sulfonyl compound shown in the following Table 1 was used in place of p-toluenesulfonyl chloride in Example 2, optically active phosphoric acid derivatives represented by the following formula were produced.

TABLE 1

| Example | Sulfonyl compound | Product | Yield(Weight)/mg | Yield/% |
|---|---|---|---|---|
| 3 | CF$_3$SO$_2$Cl | E$^1$ = CF$_3$<br>E$^2$ = H | 48.8 | 80 |
| 4 | PhSO$_2$Cl | E$^1$ = Ph<br>E$^2$ = H | 59.5 | 95 |
| 5 | β-NaphSO$_2$Cl | E$^1$ = β-Naph<br>E$^2$ = H | 67.6 | 93 |
| 6 | p-NO$_2$C$_6$H$_4$SO$_2$Cl | E$^1$ = p-NO$_2$C$_6$H$_4$<br>E$^2$ = H | 63.3 | 83 |
| 7 | p-CH$_3$OC$_6$H$_4$SO$_2$Cl | E$^1$ = p-CH$_3$OC$_6$H$_4$<br>E$^2$ = H | 67.3 | 98 |
| 8 | 3,5-CF$_3$C$_6$H$_4$SO$_2$Cl | E$^1$ = 3,5-CF$_3$C$_6$H$_4$<br>E$^2$ = H | 79.1 | 88 |
| 9 | p-CH$_3$C$_6$H$_4$SO$_2$Cl | E$^1$ = p-CH$_3$C$_6$H$_4$<br>E$^2$ = Br | 69.1 | 85 |

Example 3

$^1$NMR (CDCl$_3$, 270 MHz): 7.37 (2H, t, J=8.2 Hz), 7.45 (2H, d, J=8.2 Hz), 7.60 (2H, t, J=8.2 Hz), 7.71 (2H, dd, J=1.9, 8.2 Hz), 7.97 (4H, d, J=8.2 Hz).

Example 4

$^1$NMR (CDCl$_3$, 270 MHz): δ 6.49-6.55 (4H, m), 6.64 (2H, t, J=7.3 Hz), 6.91 (2H, d, J=8.1 Hz), 7.05 (2H, t, J=7.3 Hz), 7.24-7.35 (8H, m), 7.71 (2H, d, J=8.1 Hz), 7.90 (2H, d, J=8.9 Hz), 8.03 (2H, d, J=8.9 Hz).

Example 5

−(β-Naph): $^1$HNMR (CD$_3$OD, 270 MHz): δ 6.40 (2H, d, J=8.5 Hz), 6.48 (2H, dt, J=1.1, 7.0 Hz), 6.76 (2H, t, J=7.0 Hz), 6.94 (2H, d, J=8.5 Hz), 7.24 (2H, dd, J=2.1, 8.9 Hz), 7.30 (2H, d, J=7.8 Hz), 7.33-7.44 (8H, m), 7.67-7.70 (4H, m), 8.82 (2H, d, J=8.9 Hz).

Example 6

$^1$HNMR (CD$_3$OD+CDCl$_3$, 270 MHz): δ 6.80 (2H, d, J=8.0 Hz), 7.11 (2H, dt, J=1.4, 8.0 Hz), 7.28 (2H, dt, J=1.4, 8.0 Hz), 7.31 (4H, d, J=9.1 Hz), 7.45 (4H, d, J=9.1 Hz), 7.59 (2H, d, J=8.0 Hz), 7.81 (2H, d, J=9.1 Hz), 7.85 (2H, d, J=9.1 Hz).

1-(p-CF$_3$-Ph): $^1$HNMR (CD$_3$OD, 270 MHz): δ 6.81 (4H, d, J=8.1 Hz), 6.93 (2H, d, J=8.6 Hz), 7.18 (2H, t, J=7.0 Hz), 7.39-7.44 (6H, m), 7.72-7.79 (6H, m).

Example 7

$^1$HNMR (CD$_3$OD, 270 MHz): δ 3.57 (6H, s), 6.00 (4H, d, J=8.9 Hz), 6.81 (2H, d, J=8.6 Hz), 7.08 (4H, d, J=8.9 Hz), 7.11 (2H, m), 7.40 (2H, t, J=7.0 Hz), 7.75-7.87 (6H, m).

Example 8

$^1$HNMR (CD$_3$OD, 270 MHz): δ 6.66 (2H, d, J=8.0 Hz), 7.05 (2H, t, J=8.0 Hz), 7.34 (2H, t, J=8.0 Hz), 7.39 (2H, s), 7.70 (2H, d, J=8.0 Hz), 7.83 (4H, s), 7.93 (4H, brs).

Example 9

Synthesis of the Following Optically Active Phosphoric Acid Derivative

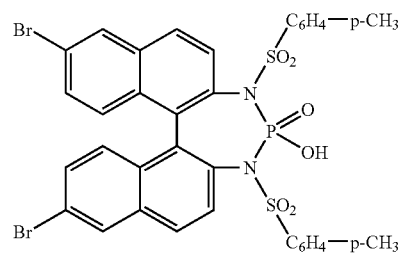

According to the same manner as described in Example 2 except that 6,6'dibromo-1,1'-binaphthyl-2,2'-diamine was used in place of 1,1'-binaphthyl-2,2'-diamine in Example 2, the optically active phosphoric acid derivative represented by the above formula was produced. Yield (Weight): 69.1 mg. Yield: 85% yield.

$^1$HNMR (acetone-$d_6$, 270 MHz): δ 2.01 (6H, s), 6.43 (4H, d, J=8.1 Hz), 6.54 (2H, d, J=9.0 Hz), 7.07 (4H, d, J=8.1 Hz), 7.19 (2H, d, J=9.0 Hz), 7.95-8.10 (6H, m).

Example 10

Synthesis of the Following Optically Active Phosphoric Acid Derivative

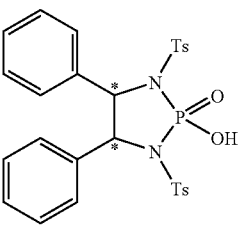

According to the same manner as described in Example 2 except that (1R,2S)-diphenylethylenediamine was used in place of 1,1'-binaphthyl-2,2'-diamine in Example 2, the optically active phosphoric acid derivative represented by the above formula was produced. Yield (Weight): 52.4 mg. Yield: 90% yield.

$^1$HNMR (CDCl$_3$, 270 MHz): δ 2.23 (6H, s), 4.49 (2H, d, J=13.5 Hz), 6.95 (4H, d, J=8.1 Hz), 7.04 (6H, br), 7.30 (4H, brd, J=7.6 Hz), 7.69 (4H, d, J=8.1 Hz).

Example 11

Synthesis of the Following Optically Active Phosphoric Acid Derivative

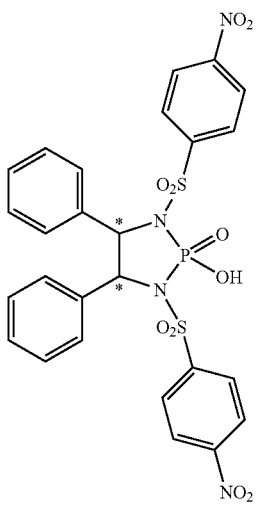

According to the same manner as described in Example 2 except that p-nitrophenylsulfonyl chloride was used in place of p-toluenesulfonyl chloride in Example 2, the optically active phosphoric acid derivative represented by the above formula was produced. Yield (Weight): 51.6 mg. Yield: 90% yield.

$^1$HNMR (CDCl$_3$, 270 MHz): δ 4.48 (2H, d, J=13.2 Hz), 6.96 (6H, t, J=3.2 Hz), 7.44 (4H, m), 7.89-7.96 (8H, m).

Example 12

Synthesis of the Following Optically Active Phosphoric Acid Derivative

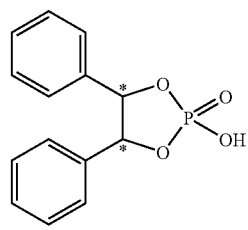

According to the same manner as described in Example 1(2) except that (1R,2S)-diphenylethylene glycol was used in place of N,N'-di-p-toluenesulfonyl-1,2-phenylenediamine in Example 1(2), the optically active phosphoric acid derivative represented by the above formula was produced.

$^1$HNMR (CD$_3$OD, 270 MHz): 5.30 (2H, br), 7.14 (4H, br), 7.27 (2H, br), 7.37 (4H, br).

Example 13

Synthesis of the Following Optically Active Phosphoric Acid Derivative

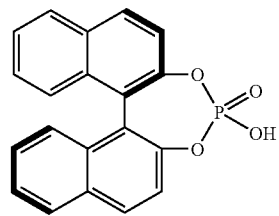

According to the same manner as described in Example 1(2) except that 1,1'-binaphthyl-2,2'-diol was used in place of 1,1'-binaphthyl-2,2'-diamine in Example 1(2), an optically active phosphoric acid derivative represented by the above formula was produced.

Example 14

Synthesis of Optically Active Amines

Under nitrogen atmosphere, to a solution in which 0.002 mmol of the following phosphoric acid derivative and 0.1 mmol of various imine compounds were dissolved in 800 μL of a solvent was added 0.11 mmol of acetylacetones at room temperature to perform the reaction with stirring. After completion of the reaction, reaction completion was confirmed by NMR, and the reaction solution was purified by column chromatography on silica gel to obtain an objective substance. The optically active phosphoric acid derivative, the imine compound, the reaction time, the Yield (Weight) and the yield used are shown in the following Tables 2 to 6.

TABLE 2

| Entry | $R^2$ | $R^1$ | $R^Y$, $R^Z$ | Phosphoric acid derivative | Solvent | Reaction time | Yield % | Optical yield % |
|---|---|---|---|---|---|---|---|---|
| 1 | Ph | Bz | Me | achiral | CDCl$_3$ | 10 min | 91 | — |
| 2 | " | " | " | 1: R = Tf | " | 2.5 d | 68 | 14 (f) |
| 3 | " | " | " | 1: R = Bs | " | 6 d | 50 | 3 (s) |
| 4 | " | " | " | 1: R = β-NaphSO$_2$ | " | 6 d | 69 | 32 (s) |
| 5 | " | " | " | 1: R = (4-MeOPhSO$_2$) | " | 6 d | 68 | 11 (s) |
| 6 | " | " | " | 1: R = Ts | " | 6 d | 50 | 41 (f) |
| 7 | " | " | " | 1: R = (4-CF$_3$PhSO$_2$) | " | 2.5 d | 63 | 4 (s) |
| 8 | " | " | " | 1: R = (4-NO$_2$PhSO$_2$) | " | 3 d | 51 | 28 (s) |
| 9 | " | " | " | 1: R = (3,5-CF$_3$PhSO$_2$) | " | 2.5 d | 66 | 5 (f) |
| 10 | " | " | " | 1: R = Ts, 6,6'-Br— | " | 4 d | 59 | 10 (s) |
| 11 | " | " | " | 2: R = H | " | 2 h | 92 | 20 (s) |
| 12 | " | " | " | 2: R = Ph | " | 3 d | 73 | 31 (s) |
| 13 | " | " | " | 2: R = β-Naph | " | 2 d | 74 | 40 (s) |
| 14 | " | " | " | 2: R = (4-MeOPh) | " | 5 d | 72 | 21 (s) |
| 15 | " | " | " | 2: R = (4-MePh) | " | 4.5 d | 70 | 51 (s) |
| 16 | " | " | " | 2: R = (4-t-BuPh) | " | 3.5 d | 79 | 23 (s) |
| 17 | " | " | " | 2: R = (4-PhPh) | " | 3.5 d | 81 | 43 (s) |
| 18 | " | " | " | 2: R = (4-CF$_3$Ph) | " | 5.5 d | 77 | 66 (s) |
| 19 | " | " | " | 2: R = (4-NO$_2$Ph) | " | 4 d | 82 | 14 (s) |
| 20 | " | " | " | 2: R = (3,4,5-F$_3$Ph) | " | 14 h | 81 | 7 (s) |
| 21 | " | " | " | 2: R = (3,5-PhPh) | " | 1.5 d | 80 | 3 (s) |
| 22 | " | " | " | 2: R = (3,5-CF$_3$Ph) | " | 14 h | 81 | 3 (s) |
| 23 | " | " | " | 2: R = OMe | " | 5 d | 70 | 31 (f) |
| 24 | " | " | " | 2: R = Br | " | 6 h | 99 | 61 (s) |
| 25 | " | " | " | 2: R = I | " | 3 d | 57 | 21 (s) |

TABLE 3

| Entry | $R^2$ | $R^1$ | $R^Y$, $R^Z$ | Phosphoric acid derivative | Solvent | Reaction time | Yield (%) | Optical yield (%) |
|---|---|---|---|---|---|---|---|---|
| 26 | Ph | Bz | $R^Y$, $R^Z$ = Me | 2: R = TPS | CDCl$_3$ | 7 d | 79 | 5 (s) |
| 27 | " | " | " | 2: R = H, 6,6'-Br— | " | 5 d | 71 | 20 (s) |
| 28 | " | " | " | 3: R = (p-tol) | " | 2 d | 83 | 15 (f) |
| 29 | " | " | " | 3: R = (4-NO$_2$—Ph) | " | 5 d | 76 | 4 (s) |
| 30 | " | " | " | 4 | " | 1 d | 87 | 5 (s) |
| 31 | " | " | " | 5 | " | 2 h | 75 | 3 (f) |
| 32 | " | " | $R^Y$ = Ph, $R^Z$ = H | achiral | " | 10 min | 87 | — |
| 33 | " | " | $R^Y$, $R^Z$ = —(CH$_2$)$_3$— | " | " | 10 min | 83 | — |
| 34 | " | " | $R^Y$, $R^Z$ = Ph | " | " | 10 min | 89 | — |
| 35 | " | " | $R^Y$ = OMe, $R^Z$ = Me | " | " | 4 h | 93 | — |
| 36 | " | " | $R^Y$ = NMe$_2$, $R^Z$ = Me | " | " | 10 min | 94 | — |
| 37 | " | 1-Naphthoyl | $R^Y$, $R^Z$ = Me | achiral | " | 20 min | 90 | — |
| 38 | " | " | " | 1: R = β-NaphSO$_2$ | " | 2.5 d | 82 | 11 (s) |
| 39 | " | " | " | 1: R = Ts | " | 2.5 d | 82 | 33 (s) |
| 40 | " | " | " | 2: R = H | " | 20 min | 88 | 17 (s) |
| 41 | " | " | " | 2: R = Ph | " | 3 d | 79 | 21 (s) |
| 42 | 1-Naphthyl | Bz | " | achiral | " | 20 min | 95 | — |
| 43 | " | " | " | 1: R = Ts | " | 4 d | 80 | 14 (f) |
| 44 | Ph | Boc | $R^Y$, $R^Z$ = Me | achiral | " | 10 min | 95 | — |
| 45 | " | " | " | 1: R = Ts | " | 2 d | 80 | 3 (S) |
| 46 | " | " | " | 2: R = H | " | 1.5 h | 85 | 9 (R) |
| 47 | " | " | " | " | CH$_2$Cl$_2$ | 1 h | 92 | 12 (R) |
| 48 | " | " | " | 2: R = Ph | CDCl$_3$ | 2 h | 91 | 58 (S) |
| 49 | " | " | " | " | CH$_2$Cl$_2$ | 1 h | 95 | 56 (S) |
| 50 | " | " | " | " | Toluene | 2.5 d | 88 | 32 (S) |

TABLE 4

| Entry | $R^2$ | $R^1$ | $R^Y$, $R^Z$ | Phosphoric acid derivative | Solvent | Reaction time | Yield (%) | Optical yield (%) |
|---|---|---|---|---|---|---|---|---|
| 51 | Ph | Boc | $R^Y$, $R^Z$ = Me | 2: R = Ph | Ether | 2.5 d | 58 | 37 (S) |
| 52 | " | " | $R^Y$, $R^Z$ = Me | " | THF | 2.5 d | 63 | 31 (R) |
| 53 | " | " | $R^Y$, $R^Z$ = Me | 2: R = β-Naph | CDCl$_3$ | 1.5 h | 90 | 51 (S) |
| 54 | " | " | $R^Y$, $R^Z$ = Me | 2: R = (4-MeOPh) | " | 17 h | 87 | 28 (S) |
| 55 | " | " | $R^Y$, $R^Z$ = Me | 2: R = (4-MePh) | " | <4 h | 93 | 81 (S) |
| 56 | " | " | $R^Y$, $R^Z$ = Me | 2: R = (4-t-BuPh) | " | 5 h | 89 | 19 (R) |
| 57 | " | " | $R^Y$, $R^Z$ = Me | 2: R = (4-Ph—Ph) | " | 1.5 h | 92 | 91 (S) |
| 58 | " | " | $R^Y$, $R^Z$ = Me | " | toluene | 2 h | 85 | 82 (S) |
| 59 | " | " | $R^Y$, $R^Z$ = Me | " | CH$_2$Cl$_2$ | 2 h | 88 | 90 (S) |
| 60 | " | " | $R^Y$, $R^Z$ = Me | " | $^i$Pr$_2$O | 2 h | 91 | 85 (S) |
| 61 | " | " | $R^Y$, $R^Z$ = Me | " | ether | 2 h | 90 | 83 (S) |
| 62 | " | " | $R^Y$, $R^Z$ = Me | " | MeCN | 2 h | 78 | 40 (S) |
| 63 | " | " | $R^Y$, $R^Z$ = Me | " | THF | 2 h | 30 | 19 (S) |
| 64 | " | " | $R^Y$, $R^Z$ = Me | 2: R = (4-(2-Naph)-Ph) | CDCl$_3$ | 10 min | 98 | 93 (S) |
| 65 | " | " | $R^Y$, $R^Z$ = Me | 2: R = (4-(2-Naph)-Ph) | toluene | 1 h | 94 | 86 (S) |
| 67 | " | " | $R^Y$, $R^Z$ = Me | 2: R = (4-(2-Naph)-Ph) | CH$_2$Cl$_2$ | 1 h | 99 | 95 (S) |
| 68 | " | " | $R^Y$, $R^Z$ = Me | 2: R = (1 g scale, 1 mol %) | " | 2 h | 92 | 94 (S)* |
| 69 | " | " | $R^Y$, $R^Z$ = Me | " | $^i$Pr$_2$O | 1 h | 92 | 86 (S) |
| 70 | " | " | $R^Y$, $R^Z$ = Me | " | ether | 1 h | 97 | 88 (S) |
| 71 | 4-MeO—C$_6$H$_4$— | " | $R^Y$, $R^Z$ = Me | " | CH$_2$Cl$_2$ | 1 h | 93 | 90 |
| 72 | " | " | $R^Y$, $R^Z$ = Me | achiral | CDCl$_3$ | 10 min | 92 | — |
| 73 | 4-Me—C$_6$H$_4$— | " | $R^Y$, $R^Z$ = Me | 2: R = (4-(2-Naph)-Ph) | CH$_2$Cl$_2$ | 1 h | 98 | 94 |
| 74 | " | " | $R^Y$, $R^Z$ = Me | achiral | CDCl$_3$ | 10 min | 93 | — |
| 75 | 4-Br—C$_6$H$_4$— | " | $R^Y$, $R^Z$ = Me | 2: R = (4-(2-Naph)-Ph) | CH$_2$Cl$_2$ | 1 h | 96 | 98 |

TABLE 5

| Entry | $R^2$ | $R^1$ | RY, RZ | Phosphoric acid derivative | Solvent | Reaction time | Yield (%) | Optical yield (%) |
|---|---|---|---|---|---|---|---|---|
| 76 | 4-Br—C$_6$H$_4$— | Boc | $R^Y$, $R^Z$ = Me | achiral | CDCl$_3$ | 30 min | 99 | — |
| 77 | 4-F—C$_6$H$_4$— | " | " | 2: R = (4-(2-Naph)-Ph) | CH$_2$Cl$_2$ | 1 h | 94 | 96 |
| 78 | " | " | " | achiral | CDCl$_3$ | 30 min | 96 | — |
| 79 | 2-Me—C$_6$H$_4$— | " | " | 2: R = (4-(2-Naph)-Ph) | CH$_2$Cl$_2$ | 1 h | 94 | 93 |
| 80 | " | " | " | achiral | CDCl$_3$ | 20 min | 96 | — |
| 81 | 1-Naphthyl- | " | " | 2: R = (4-(2-Naph)-Ph) | CH$_2$Cl$_2$ | 1 h | 99 | 92 |
| 82 | " | " | " | achiral | CDCl$_3$ | 20 min | 99 | — |
| 83 | Ph | " | " | 2: R = (4-CF$_3$Ph) | " | 1.5 h | 90 | 69 (S) |
| 84 | " | " | " | 2: R = (4-NO$_2$Ph) | " | 1 h | 92 | 69 (S) |
| 85 | " | " | " | 2: R = (3,4,5-F$_3$Ph) | " | 0.5 h | 88 | 36 (S) |
| 86 | " | " | " | 2: R = (3,5-PhPh) | " | 0.5 h | 87 | 45 (R) |

TABLE 5-continued

| Entry | $R^2$ | $R^1$ | RY, RZ | Phosphoric acid derivative | Solvent | Reaction time | Yield (%) | Optical yield (%) |
|---|---|---|---|---|---|---|---|---|
| 87 | " | " | " | 2: R = (3,5-CF$_3$Ph) | " | 1 h | 90 | 22 (R) |
| 88 | " | " | " | 2: R = OMe | " | 2 d | 84 | 10 (S) |
| 89 | " | " | " | 2: R = Br | " | 1 h | 91 | >34 (R) |
| 90 | " | " | " | 2: R = I | " | 2 d | 89 | 31 (S) |
| 91 | " | " | " | 2: R = TPS | " | 2.5 d | 90 | rac |
| 92 | " | " | " | 2: R = H, 6,6'-Br— | " | 1 d | 84 | rac |
| 93 | " | " | R$^Y$ = OMe, R$^Z$ = Me | 2: R = (4-(2-Naph)-Ph) | " | 12 h | 90 (1.1:1) | 41, 29, 60 |
| 94 | " | " | R$^Y$ = OMe, R$^Z$ = Me | achiral | " | 4 h | 92 | — |
| 95 | " | " | R$^Y$ = NMe$_2$, R$^Z$ = Me | 2: R = (4-(2-Naph)-Ph) | " | Sluggish | — | — |
| 96 | " | " | R$^Y$ = NMe$_2$, R$^Z$ = Me | 2: R = (4-Ph—Ph) | " | 15 h | 86 | 15, 8 |
| 97 | " | " | R$^Y$ = NMe$_2$, R$^Z$ = Me | achiral | " | 10 min | 96 | — |
| 98 | " | " | R$^Y$, R$^Z$ = Me | H8-2: R = (4-Ph—Ph) | " | 1 h | 84 | 95 |

*after recrystallization, >99% ee; 75% yield (82% based on product)

In Table 2 and Table 3, the expression of (f) and (s) is as follows: Upon enantiomer analysis in chiral HPLC analysis (column: Chiralpak AD-H, solvent: hexane/ethanol=90/10 (V/V)), when a peak observed first is a main component, this is described as (f), and when a peak observed afterward is a main component, this is described as (s).

Phosphoric Acid Derivative:

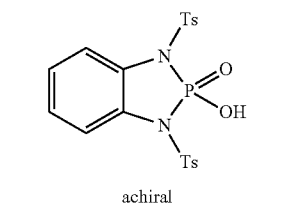

achiral

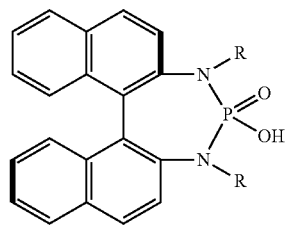

1

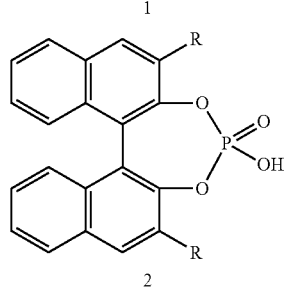

2

-continued

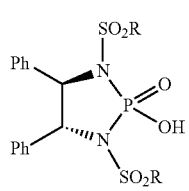

3

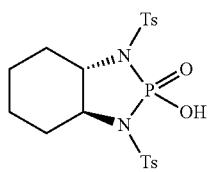

4

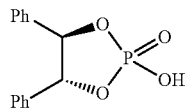

5

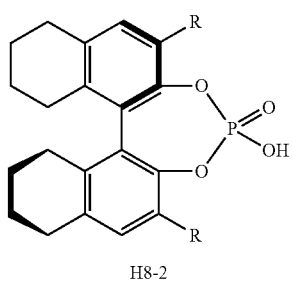

H8-2

TABLE 6

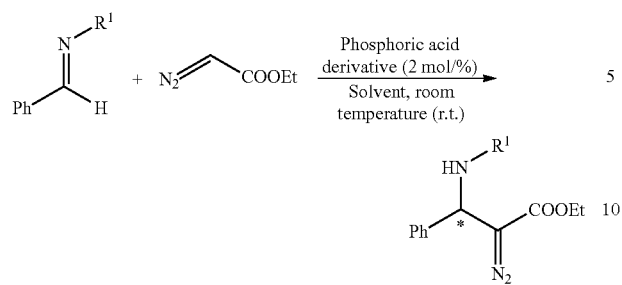

| Entry | R[1] | Phosphoric acid derivative | Solvent | Reaction time | Yield (%) | Optical yield (%) |
|---|---|---|---|---|---|---|
| 1 | Bz | achiral | Toluene | 1 h | 27 | rac |
| 2 | Bz | 1: R = Ts | CDCl$_3$ | 7 d | 61 | 22 (f) |
| 3 | Bz | 1: R = β-NaphSO$_2$ | CDCl$_3$ | 6 d | 58 | 22 (s) |
| 4 | Bz | 2: R = H | CDCl$_3$ | 10 min | 59 | 5 (f) |
| 5 | Bz | 2: R = Ph | CDCl$_3$ | 5 d | 40 | 23 (f) |
| 6 | Bz | 2: R = p-MeO—Ph | CDCl$_3$ | 7 d | 57 | 9 (f) |
| 7 | Bz | 2: R = p-Me—Ph | CDCl$_3$ | 4.5 d | 42 | 22 (f) |
| 8 | Bz | 2: R = p-t-Bu—Ph | CDCl$_3$ | 3.5 d | 54 | 5 (f) |
| 9 | Bz | 2: R = p-Ph—Ph | CDCl$_3$ | 3.5 d | 62 | 30 (f) |
| 10 | Bz | 2: R = p-CF$_3$—Ph | CDCl$_3$ | 3.5 d | 70 | 22 (f) |
| 11 | Bz | 2: R = p-NO$_2$—Ph | CDCl$_3$ | 7 d | 48 | 16 (f) |
| 12 | Bz | 2: R = 3,4,5-F$_3$—Ph | CDCl$_3$ | 4 d | 52 | 10 (f) |
| 13 | Bz | 2: R = 3,5-Me—Ph | CDCl$_3$ | 4 d | 47 | 33 (f) |
| 14 | Bz | 2: R = 3,5-Ph—Ph | CDCl$_3$ | 3 d | 53 | 50 (f) |
| 15 | Bz | 2: R = 3,5-CF$_3$—Ph | CDCl$_3$ | 6 d | 60 | 38 (f) |
| 16 | Bz | 2: R = 3,5-CF$_3$—Ph | ether | 2 d | 58 | 32 (f) |
| 17 | Bz | 2: R = 3,5-CF$_3$—Ph | THF | 2 d | 39 | 27 (f) |
| 18 | Bz | 2: R = β-Naph | CDCl$_3$ | 4 d | 58 | 28 (f) |
| 19 | Bz | 2: R = Br | CDCl$_3$ | 5 d | 46 | 31 (f) |
| 20 | Bz | 2: R = I | CDCl$_3$ | 7 d | 43 | 26 (f) |
| 21 | Bz | 2: R = OMe | CDCl$_3$ | 8 d | 50 | 10 (f) |
| 22 | Bz | 2: R = TPS | CDCl$_3$ | 11 d | 52 | 3 (f) |
| 23 | Bz | 2: R = H, 6,6'-Br— | CDCl$_3$ | 7 d | 46 | 7 (s) |
| 24 | α-Naph | achiral | Toluene | 1 h | 30 | rac |
| 25 | α-Naph | 2: R = 3,5-t-Bu—Ph | CDCl$_3$ | 3 d | 68 | 58 (s) |
| 26 | α-Naph | 2: R = 3,5-Ph—Ph | CDCl$_3$ | 4.5 d | 68 | 70 (s) |
| 27 | α-Naph | 2: R = Ph$_2$C(OH) | CDCl$_3$ | 4.5 d | 52 | 72 (f) |
| 28 | β-naph | achiral | Toluene | 1 h | 34 | rac |
| 29 | β-Naph | 2: R = 3,5-Ph—Ph | CDCl$_3$ | 3 d | 52 | 48 (s) |
| 30 | Boc | achiral | CDCl$_3$ | 10 min | 37 | rac |
| 31 | Boc | 2: R = H | CDCl$_3$ | 10 min | 90 | 8 (f) |
| 32 | Boc | 2: R = Ph | CDCl$_3$ | 5 d | 46 | 14 (f) |
| 33 | Boc | 2: R = p-MeO—Ph | CDCl$_3$ | 6 d | 40 | 2 (s) |
| 34 | Boc | 2: R = p-Me—Ph | CDCl$_3$ | 4 d | 46 | 13 (f) |
| 35 | Boc | 2: R = p-t-Bu—Ph | CDCl$_3$ | 3 d | 48 | 36 (f) |
| 36 | Boc | 2: R = p-Ph—Ph | CDCl$_3$ | 4 h | 60 | 8 (f) |
| 37 | Boc | 2: R = p-CF$_3$—Ph | CDCl$_3$ | 3 d | 44 | 12 (f) |
| 38 | Boc | 2: R = p-NO$_2$—Ph | CDCl$_3$ | 6 d | 31 | 2 (f) |
| 39 | Boc | 2: R = 3,4,5-F$_3$—Ph | CDCl$_3$ | 4 d | 51 | 9 (f) |
| 40 | Boc | 2: R = 3,5-Ph—Ph | CDCl$_3$ | 1 d | 67 | 8 (f) |
| 41 | Boc | 2: R = 3,5-CF$_3$—Ph | CDCl$_3$ | 3 d | 50 | 9 (s) |
| 42 | Boc | 2: R = β-Naph | CDCl$_3$ | 2 d | 49 | 8 (f) |
| 43 | Boc | 2: R = Br | CDCl$_3$ | 6 d | 48 | 26 (f) |
| 44 | Boc | 2: R = I | CDCl$_3$ | 3 d | 59 | 18 (f) |
| 45 | Boc | 2: R = H 6,6'-Br— | CDCl$_3$ | 7 d | 37 | 20 (s) |

In Table 6, expression of (f) and (s) is as follows: Upon enantiomer analysis in chiral HPLC analysis (column: Chiralpak AD-H, solvent: hexane/isopropanol=90/10 (V/V)), when a peak observed first is a main component, this is described as (f) and, when a peak observed afterward is a main component, this is described as (s).

Phosphoric Acid Derivative:

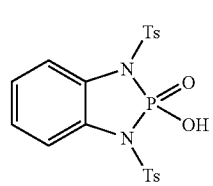

achiral

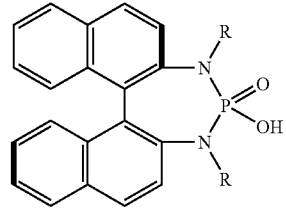

1

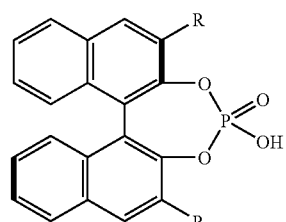

2

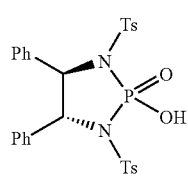

3

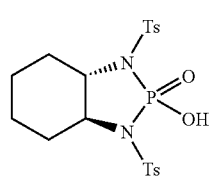

4

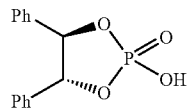

5

In the reaction time in the above Table, min represents minute, h represents hour, and d represents day, respectively (hereinafter the same).

NMR and melting points of products:

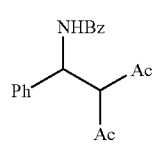

$^1$H NMR (CDCl$_3$, 270 MHz): δ 2.10 (3H, s), 2.30 (3H, s), 4.90 (1H, d, J=5.1 Hz), 6.04 (1H, dd, J=5.1, 9.2 Hz), 7.20-7.30 (1H, m), 7.31 (4H, d, J=4.1 Hz), 7.41 (2H, tt, J=1.6, 7.3 Hz), 7.50 (1H, tt, J=1.6, 7.3 Hz), 7.78 (2H, dt, J=1.6, 7.3 Hz), 7.93 (1H, brd, J=9.2 Hz). Melting point; 193-194° C.

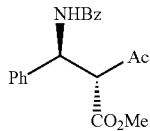

major isomer: ¹H NMR (CDCl₃, 270 MHz): δ 2.38 (3H, s), 3.66 (3H, s), 4.15 (1H, d, J=3.8 Hz), 6.09 (1H, dd, J=3.8, 9.5 Hz), 7.22-7.33 (5H, m), 7.39-7.54 (3H, m), 7.78-7.83 (2H, m), 8.14 (1H, brd, J=9.5 Hz). Melting point (diastero-mixture); 158° C.

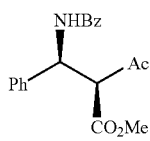

minor isomer: ¹H NMR (CDCl₃, 270 MHz): δ 2.15 (3H, s), 3.70 (3H, s), 4.20 (1H, d, J=4.9 Hz), 5.94 (1H, dd, J=4.9, 8.6 Hz), 7.22-7.33 (5H, m), 7.39-7.54 (3H, m), 7.78-7.83 (2H, m), 7.87 (1H, brd, J=8.6 Hz). Melting point (diastero-mixture); 158° C.

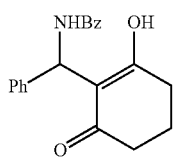

¹H NMR (CDCl₃, 270 MHz): δ 1.95 (2H, brquin, J=6.5 Hz), 2.33 (2H, brt, J=6.5 Hz), 2.64 (2H, brt, J=6.5 Hz), 6.59 (1H, d, J=9.5 Hz), 7.16-7.29 (3H, m), 7.38-7.55 (5H, m), 7.87 (2H, d, J=8.4 Hz), 8.93 (1H, brd, J=9.5 Hz), 11.27 (1H, br). Melting point; 208-209° C.

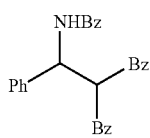

¹HNMR (CDCl₃, 270 MHz): δ 6.08 (1H, dd, J=3.2, 8.1 Hz), 6.10 (1H, s), 7.17-7.56 (13H, m), 7.64 (1H, td, J=1.4, 7.3 Hz), 7.79 (2H, td, J=1.4, 8.1 Hz), 7.84 (2H, td, J=1.4, 6.5 Hz), 8.06 (2H, td, J=1.6, 7.3 Hz), 8.52 (1H, d, J=8.1 Hz). Melting point; 222° C.

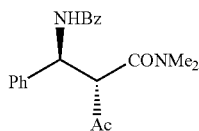

major isomer: ¹H NMR (CDCl₃, 270 MHz): δ 2.16 (3H, s), 2.80 (3H, s), 3.01 (3H, s), 4.34 (1H, d, J=7.3 Hz), 5.90 (1H, dd, J=7.0, 9.2 Hz), 7.14-7.46 (8H, m), 7.82 (2H, td, J=1.6, 7.0 Hz), amide proton was not detected. Melting point (diastero-mixture); 69-71° C.

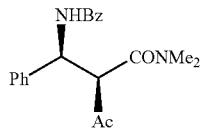

minor isomer: ¹H NMR (CDCl₃, 270 MHz): δ 2.29 (3H, s), 2.59 (3H, s), 2.84 (3H, s), 4.11 (1H, d, J=3.2 Hz), 5.97 (1H, dd, J=3.2, 8.1 Hz), 7.14-7.46 (8H, m), 7.82 (2H, td, J=1.6, 6.8 Hz), 9.13 (1H, brd, J=8.1 Hz). Melting point (diastero-mixture); 69-71° C.

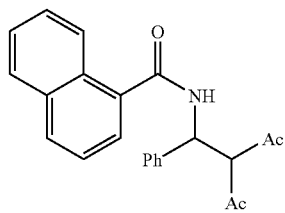

¹H NMR (CDCl₃, 270 MHz): δ 2.13 (3H, s), 2.38 (3H, s), 4.42 (1H, d, J=5.4 Hz), 6.17 (1H, dd, J=5.4, 9.5 Hz), 7.24-7.36 (5H, m), 7.42 (1H, d, J=7.3 Hz), 7.44-7.53 (2H, m), 7.55 (1H, br), 7.59 (1H, dd, J=1.4, 7.0 Hz), 7.84 (1H, m), 7.91 (1H, d, J=8.1 Hz), 8.21 (1H, m).

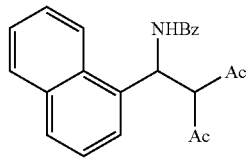

¹H NMR (CDCl₃, 270 MHz): δ 1.95 (3H, s), 2.45 (3H, s), 4.53 (1H, d, J=4.3 Hz), 6.81 (1H, dd, J=4.3, 8.9 Hz), 7.36-7.56 (6H, m), 7.64 (1H, dt, J=1.4, 7.0 Hz), 7.60-7.85 (3H, m), 7.89 (1H, d, J=8.6 Hz), 8.21 (1H, d, J=8.6 Hz).

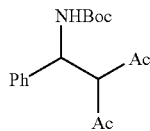

¹H NMR (CDCl₃, 270 MHz): δ 1.37 (9H, s), 2.09 (3H, s), 2.17 (3H, brs), 4.18 (1H, d, J=6.8 Hz), 5.46 (1H, br), 5.73 (1H, br), 7.20-7.34 (5H, m). Melting point; 176° C.

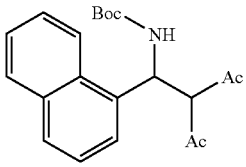

¹H NMR (CDCl₃, 270 MHz): δ 1.37 (9H, s), 1.96 (3H, s), 2.30 (3H, s), 4.40 (1H, d, J=5.4 Hz), 6.16 (1H, brs), 6.29 (1H, brs), 7.37-7.44 (2H, m), 7.50 (1H, t, J=6.8 Hz), 7.59 (1H, dt, J=1.4, 6.8 Hz) 7.70-7.80 (1H, m), 7.86 (1H, d, J=7.8 Hz) 8.16 (1H, d, J=8.4 Hz).

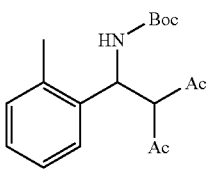

¹H NMR (CDCl₃, 270 MHz): δ 1.35 (9H, s), 2.11 (6H, s), 2.48 (3H, s), 4.11 (1H, d, J=7.0 Hz), 5.66 (2H, brs), 7.13-7.16 (4H, m).

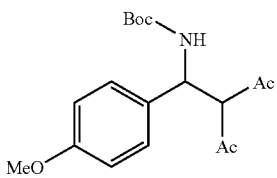

¹H NMR (CDCl₃, 270 MHz): δ 1.39 (9H, s), 2.10 (3H, s), 2.12 (3H, s), 3.75 (3H, s), 4.15 (1H, d, J=7.0 Hz), 5.40 (1H, brs), 5.65 (1H, brs), 6.81 (2H, d, J=8.5 Hz), 7.16 (2H, d, J=8.5 Hz).

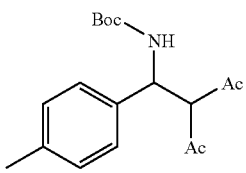

¹H NMR (CDCl₃, 270 MHz): δ 1.36 (9H, s), 2.10 (3H, s), 2.15 (3H, s), 2.28 (1H, d, J=5.4 Hz), 4.17 (1H, d, J=7.0 Hz), 5.43 (1H, brs), 5.70 (1H, brs), 7.07-7.15 (4H, m).

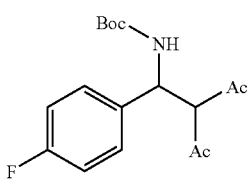

¹H NMR (CDCl₃, 270 MHz): δ 1.36 (9H, s), 2.09 (3H, s), 2.16 (3H, s), 4.15 (1H, d, J=6.8 Hz), 5.42 (1H, brs), 5.47 (1H, brs), 6.94-7.03 (2H, m), 7.19-7.26 (2H, m).

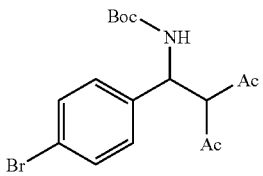

¹H NMR (CDCl₃, 270 MHz): δ 1.37 (9H, s), 2.08 (3H, s), 2.19 (3H, s), 4.14 (1H, d, J=6.2 Hz), 5.41 (1H, brs), 5.79 (1H, brs), 7.14 (2H, d, J=8.5 Hz), 7.42 (2H, d, J=8.5 Hz).

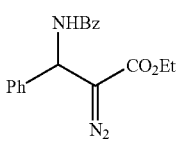

¹H NMR (CDCl₃, 270 MHz): δ 1.27 (3H, t, J=7.0 Hz), 4.25 (2H, q, J=7.0 Hz), 6.20 (1H, d, J=8.4 Hz), 7.28-7.56 (9H, m), 7.84 (2H, d, J=5.9 Hz).

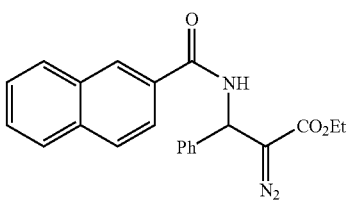

¹H NMR (CDCl₃, 270 MHz): δ 1.28 (3H, t, J=7.0 Hz), 4.27 (2H, q, J=7.0 Hz), 6.27 (1H, d, J=8.1 Hz), 7.33-7.61 (8H, m), 7.87-7.96 (4H, m), 8.36 (1H, s).

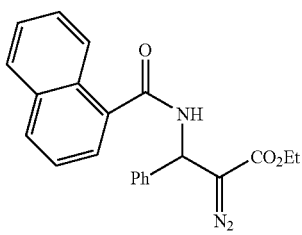

¹H NMR (CDCl₃, 270 MHz): δ 1.28 (3H, t, J=7.0 Hz), 4.26 (2H, q, J=7.0 Hz), 6.30 (1H, d, J=7.8 Hz), 7.30-7.58 (9H, m), 7.68 (1H, d, J=7.0 Hz), 7.87-7.96 (2H, m), 8.37 (1H, d, J=9.4 Hz).

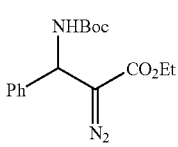

¹H NMR (CDCl₃, 270 MHz): δ 1.25 (3H, t, J=7.0 Hz), 1.45 (9H, s), 4.22 (2H, q, J=7.0 Hz), 5.39 (1H, brs), 5.39 (1H, d, J=7.6 Hz), 7.25-7.41 (5H, m).

TABLE 7

$$\text{Ph-CH=N-C(O)R}^1 \text{ (1.0 eq)} + \text{N}_2\text{=CHCOR}^2 \text{ (1.1 eq)} \xrightarrow[\text{r.t.}]{\text{2 mol \% Phosphoric acid derivative}} \text{Ph-CH(NHC(O)R}^1\text{)-C(=N}_2\text{)-CO}_2\text{R}^2$$

| Entry | Protective group (R¹=) | Substituent (R²=) | Catalyst | Solvent | Reaction time | Yield (%) | Optical yield (%) |
|---|---|---|---|---|---|---|---|
| 1 | Ph | Et | 2: R = (3,5-t-Bu—Ph) | CDCl₃ | 5.5 d | 59 | 66 |
| 2 | " | " | 2: R = (3,5-Br—Ph) | " | 4 d | 77 | 41 |
| 3 | " | " | 2: R = (3,5-TMS—Ph) | " | 1.5 d | 59 | 71 |
| 4 | " | " | 2: R = (3,5-TES—Ph) | " | 2 d | 78 | 79 |
| 5 | " | " | 2: R = (3,5-mesityl-Ph) | " | 1.5 d | 57 | 35 |
| 6 | " | " | 2: R = anthryl | " | 1.5 d | 75 | 82 |
| 7 | " | i-Pr | " | " | 3 d | 61 | 79 |
| 8 | " | t-Bu | " | " | 3 d | — | 75 (S) |
| 9 | " | Et | 2: R = mesityl | CDCl₃ | 12 h | 59 | 83 |
| 10 | " | i-Pr | " | " | 1 d | 61 | 80 |
| 11 | " | t-Bu | " | " | 11 h | — | 81 (S) |
| 12 | " | " | 2: R = β-Naph | CDCl₃ | 4 d | 58 | 28 (S) |
| 13 | " | " | 2: R = Br | " | 5 d | 46 | 31 (S) |
| 14 | " | " | 2: R = I | " | 7 d | 43 | 26 (S) |
| 15 | " | " | 2: R = MeO | " | 8 d | 50 | 10 (S) |
| 16 | " | " | 2: R = TPS | " | 11 d | 52 | 3 (S) |
| 17 | " | " | 2: R = H, 6,6'-Br— | CDCl₃ | 7 d | 46 | 7 (S) |
| 18 | OᵗBu | " | achiral | " | 10 min | 37 | — |
| 19 | " | " | 2: R = H | " | 10 min | 90 | 8 |
| 20 | " | " | 2: R = Ph | " | 5 d | 46 | 14 |
| 21 | " | " | 2: R = p-MeO—Ph | " | 6 d | 40 | 2 |
| 22 | " | " | 2: R = p-Me—Ph | " | 4 d | 46 | 13 |
| 23 | " | " | 2: R = p-t-Bu—Ph | " | 3 d | 48 | 36 |
| 24 | " | " | 2: R = p-Ph—Ph | " | 4 h | 60 | 8 |
| 25 | " | " | 2: R = p-CF₃—Ph | " | 3 d | 44 | 12 (S) |
| 26 | " | " | 2: R = p-NO₂—Ph | " | 6 d | 31 | 2 |
| 27 | " | " | 2: R = (3,4,5-F₃—Ph) | " | 4 d | 51 | 9 |
| 28 | " | " | 2: R = (3,5-Ph—Ph) | " | 1 d | 67 | 8 |
| 29 | " | " | 2: R = (3,5-CF₃—Ph) | " | 3 d | 50 | 9 |
| 30 | " | " | 2: R = (3,5-mesityl-Ph) | " | 1.5 d | 64 | 28 |
| 31 | " | " | 2: R = anthryl | " | 8 h | 80 | 58 |
| 32 | " | " | " | toluene | 8 h | 66 | 19 |
| 33 | " | " | 2: R = β-Naph | CDCl₃ | 2 d | 49 | 8 |

TABLE 8

| Entry | Protective group (R¹=) | Substituent (R²=) | Catalyst | Solvent | Reaction time | Yield (%) | Optical yield (%) |
|---|---|---|---|---|---|---|---|
| 34 | OᵗBu | t-Bu | 2: R = Br | CDCl₃ | 6 d | 48 | 26 |
| 35 | " | " | 2: R = I | " | 3 d | 59 | 18 |
| 36 | " | " | 2: R = H, 6,6'-Br— | " | 7 d | 37 | 20 |
| 37 | α-naph | " | 2: R = (3,5-Ph—Ph) | CDCl₃ | 3 d | 68 | 58 |
| 38 | " | " | 2: R = (3,5-t-Bu—Ph) | " | 4.5 d | 68 | 70 |
| 39 | " | i-Pr | " | " | 1.5 d | 65 | 73 |
| 40 | " | t-Bu | " | " | 22 h | 67 | 80 |
| 41 | " | Et | 2: R = (3,5-TMS—Ph) | CDCl₃ | 1 d | 70 | 73 |

TABLE 8-continued

| Entry | Protective group (R¹=) | Substituent (R²=) | Catalyst | Solvent | Reaction time | Yield (%) | Optical yield (%) |
|---|---|---|---|---|---|---|---|
| 42 | " | " | 2: R = (3,5-TES—Ph) | " | 2 d | 63 | 75 |
| 43 | " | Et | 2: R = anthryl | " | 1 d | 75 | 87 |
| 44 | " | i-Pr | " | " | 1 d | 75 | 68 |
| 45 | " | t-Bu | " | " | 9 h | 76 | 89 |
| 46 | " | Et | " | $CH_2Cl_2$ | 1 d | 67 | 73 |
| 47 | " | " | " | (−40° C.) | " | 33 | 55 |
| 48 | " | " | " | $Et_2O$ | " | 66 | 85 |
| 49 | " | Et | " | i-$Pr_2O$ | " | 89 | 85 |
| 50 | " | i-Pr | " | " | " | 60 | 56 |
| 51 | " | t-Bu | " | " | " | 60 | 73 |
| 52 | " | Et | " | THF | " | 32 | 63 |
| 53 | " | " | " | toluene | " | 50 | 89 |
| 54 | " | " | " | toluene (0.5M) | " | 56 | 84 |
| 55 | " | " | " | $CF_3Ph$ | " | 62 | 73 |
| 56 | " | " | " | AcOEt | " | 21 | 59 |
| 57 | " | " | " | PhH | " | 58 | 88 |
| 58 | " | " | " | cyclohexane | " | 64 | 80 |

TABLE 9

| Entry | Protective group (R¹=) | Substituent (R²=) | Catalyst | Solvent | Reaction time | Yield (%) | Optical yield (%) |
|---|---|---|---|---|---|---|---|
| 59 | α-naph | Et | 2: R = mesityl | $CDCl_3$ | 4 d | 40 | 82 |
| 60 | " | i-Pr | " | " | 2 d | 52 | 75 |
| 61 | " | t-Bu | " | " | 2 d | 58 | 82 |
| 62 | β-naph | Et | achiral | toluene | 1 h | 34 | rac |
| 63 | " | " | 2: R = (3,5-Ph—Ph) | $CDCl_3$ | 3 d | 52 | 48 |
| 64 | " | " | 2: R = (3,5-$^t$Bu—Ph) | " | 5.5 d | 59 | 67 |
| 65 | " | " | 2: R = anthryl | " | 4.5 d | 62 | 71 |
| 66 | o-OMe—Ph | t-Bu | " | " | 1.5 d | 86 | 83 |
| 67 | p-OMe—Ph | " | " | " | 1.5 d | 71 | 87 |
| 68 | o-Me—Ph | " | " | " | 2 d | 83 | 88 |
| 69 | " | Et | 2: R = mesityl | " | 22 h | 64 | 85 |
| 70 | p-Me—Ph | " | 2: R = anthryl | " | 22 h | 69 | 71 |
| 71 | " | t-Bu | " | " | 4 d | 70 | 84 |
| 72 | " | Et | 2: R = mesityl | " | 22 h | 51 | 79 |
| 73 | o-Cl—Ph | " | 2: R = anthryl | $CDCl_3$ | 3 h | 93 | 89 |
| 74 | " | " | " | toluene | 5 h | 71 | 85 |
| 75 | " | " | " | $Et_2O$ | " | 53 | 82 |
| 76 | " | " | " | $CH_2Cl_2$ | " | 44 | 69 |
| 77 | " | " | " | $CHCl_3$ | " | 57 | 86 |
| 78 | " | t-Bu | " | $CDCl_3$ | 3 h | 81 | 91 |
| 79 | " | " | " | toluene | 11 h | 72 | 90 |
| 80 | " | " | " | " | 12 h | 53 | 90 |
| 81 | " | " | " | toluene (0° C.) | 11 h | 32 | 90 |
| 82 | " | " | " | toluene (50° C.) | 1 h | 50 | 86 |
| 83 | " | " | " | mesitylene | 18 h | 61 | 89 |

TABLE 10

| Entry | Protective group (R¹=) | Substituent (R²=) | Catalyst | Solvent | Reaction time | Yield (%) | Optical yield (%) |
|---|---|---|---|---|---|---|---|
| 84 | o-Cl—Ph | t-Bu | 2: R = anthryl | PhH | 3 h | 80 | 87 |
| 85 | " | " | " | chlorobenzene | 3 h | 64 | 87 |
| 86 | " | " | " | cumene | 12 h | 60 | 87 |
| 87 | " | " | " | $CHCl_3$ | 3 h | 68 | 89 |
| 88 | " | " | " | $CHCl_3$ (0° C.) | 6 h | 29 | 85 |
| 89 | " | " | " | 1,2-dichloroethane | 3 h | 45 | 75 |
| 90 | " | " | H8-2: R = anthryl | $CDCl_3$ | 30 h | 59 | 62 |
| 91 | o-Br—Ph | Et | 2: R = anthryl | " | 5 h | 85 | 90 |

TABLE 10-continued

| Entry | Protective group ($R^1$=) | Substituent ($R^2$=) | Catalyst | Solvent | Reaction time | Yield (%) | Optical yield (%) |
|---|---|---|---|---|---|---|---|
| 92 | " | " | " | toluene | 5 h | 50 | 84 |
| 93 | " | " | " | Et$_2$O | " | 31 | 78 |
| 94 | " | " | " | CHCl$_3$ | " | 57 | 88 |
| 95 | " | i-Pr | " | CDCl$_3$ | 3 h | 58 | 90 |
| 96 | " | t-Bu | " | " | 3 h | — | 90 |
| 97 | " | " | " | CHCl$_3$ | 3 h | 26 | 85 |
| 98 | " | " | " | toluene | 11 h | 26 | 82 |
| 99 | p-Br—Ph | " | " | CDCl$_3$ | 31 h | 73 | 73 |
| 100 | o-F—Ph | " | " | CDCl$_3$ | 23 h | 61 | 80 |
| 101 | o-I—Ph | " | " | " | 20 h | 67 | 89 |
| 102 | o-NO$_2$—Ph | Et | " | " | 24 h | 92 | 4 |

Phosphoric Acid Derivative:

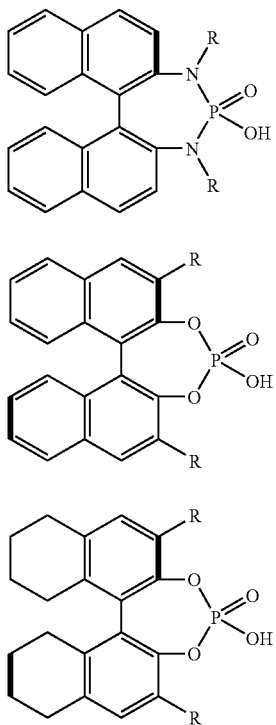

Example 15

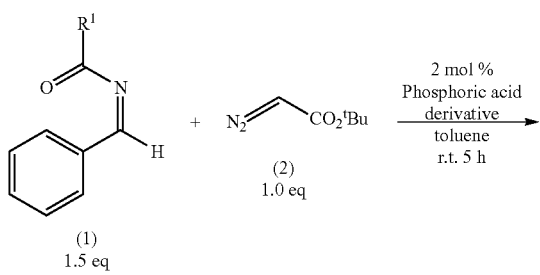

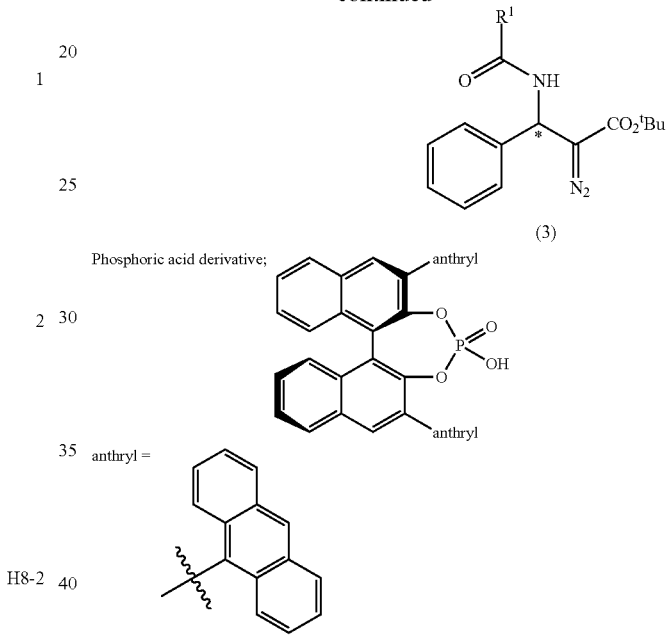

In a dry test tube under nitrogen atmosphere, diazoacetate (14.2 mg, 0.1 mmol) was added to a solution of phosphoric acid (1.40 mg, 2 mol %) and imine 1 (0.15 mmol) in toluene (1 mL, 0.1 M), and the mixture was stirred at room temperature for 5 hours. After addition of one drop of saturated aqueous sodium hydrogen carbonate solution, the precipitated solid was dissolved in dichloromethane, and progress of the reaction was confirmed by TLC, and product 3 was isolated and purified by column chromatography (Hex: AcOEt=12:1 to 6:1). Hereinafter, a similar procedure was followed. Influence of an acyl protective group ($R^1$CO) on the imine nitrogen on the yield and optical yield of the reaction is shown in the following Table 11.

TABLE 11

| | $R^1$ in acyl protective group ($R^1$CO) | Yield (%) | Optical yield (%) |
|---|---|---|---|
| 1 | Ph | 44 | 90 |
| 2 | o-MeO—Ph | 77 | 89 |
| 3 | p-MeO—Ph | 73 | 93 |
| 4 | o-Me—Ph | 84 | 90 |
| 5 | p-Me—Ph | 72 | 91 |
| 6 | o-Cl—Ph | 85 | 91 |

TABLE 11-continued

| | R¹ in acyl protective group (R¹CO) | Yield (%) | Optical yield (%) |
|---|---|---|---|
| 7 | p-Cl—Ph | 44 | 85 |
| 8 | o-Br—Ph | 80 | 90 |
| 9 | p-Br—Ph | 39 | 82 |
| 10 | p-NMe₂—Ph | 68 | 96 |
| 11 | α-naphthyl | 82 | 90 |

Compound Data

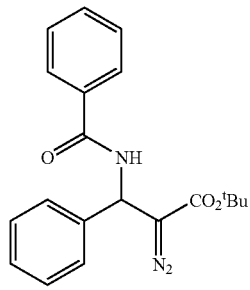

¹H NMR (270 MHz, CDCl₃): δ 1.46 (9H, s), 6.17 (1H, d, J=8.4 Hz), 7.26-7.56 (9H, m), 7.83 (2H, dt, J=6.4, 1.6 Hz).

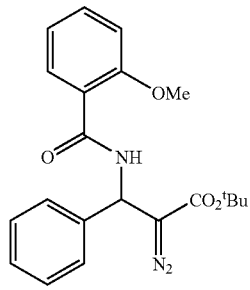

¹H NMR (270 MHz, CDCl₃): δ 1.45 (9H, s), 3.97 (3H, s), 6.21 (1H, d, J=8.1 Hz), 7.00 (1H, d, J=8.4 Hz), 7.09 (1H, t, J=7.8 Hz), 7.28-7.51 (9H, m), 8.23 (1H, dd, J=7.8 Hz), 9.00 (1H, brs).

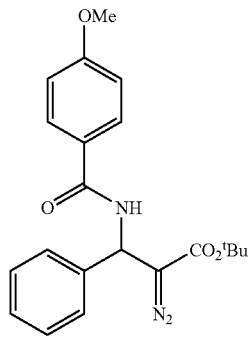

¹H NMR (270 MHz, CDCl₃): δ 1.46 (9H, s): δ 1.46 (3H, s), 6.16 (1H, d, J=8.4 Hz), 6.95 (2H, d, J=8.6 Hz), 7.30-7.43 (6H, m), 7.80 (2H, d, J=8.6 Hz)

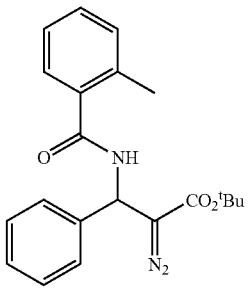

¹H NMR (270 MHz, CDCl₃): δ 1.46 (9H, s), 2.47 (3H, s), 6.13 (1H, d, J=8.4 Hz), 6.19 (1H, brs), 7.19-7.43 (9H, m).

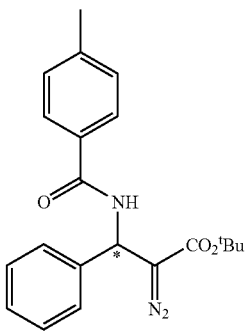

¹H NMR (270 MHz, CDCl₃): δ 1.46 (9H, s), 2.40 (3H, s), 6.16 (1H, d, J=8.4 Hz), 7.25 (2H, d, J=8.1 Hz), 7.30-7.43 (6H, m), 7.73 (2H, d, J=8.1 Hz).

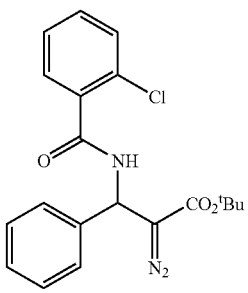

¹H NMR (270 MHz, CDCl₃): δ 1.45 (9H, s), 6.17 (1H, d, J=7.8 Hz), 6.19 (1H, brs), 7.31-7.70 (9H, m). 7.72 (1H, d, J=6.8 Hz).

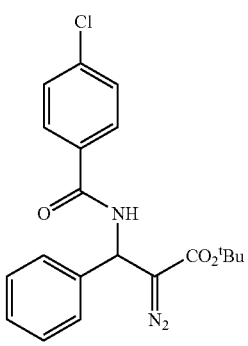

¹H NMR (270 MHz, CDCl₃): δ 1.46 (9H, s), 6.14 (1H, d, J=8.4 Hz), 7.31-7.45 (8H, m). 7.72 (1H, d, J=6.5 Hz).

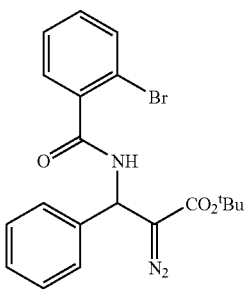

$^1$H NMR (270 MHz, CDCl$_3$): δ 1.45 (9H, s), 6.14 (1H, d, J=8.4 Hz), 7.11 (1H, brs), 7.29-7.46 (7H, m). 7.56-7.62 (2H, m).

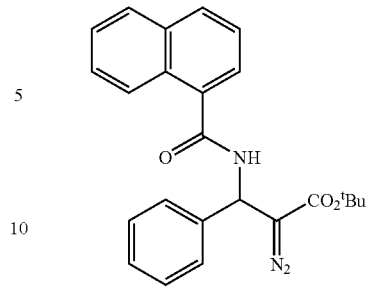

$^1$H NMR (270 MHz, CDCl$_3$): δ 1.47 (9H, s), 6.27 (1H, d, J=8.1 Hz), 7.16 (1H, brs), 7.30-7.59 (8H, m). 7.67 (1H, dd, J=7.3, 1.1 Hz), 7.86-7.90 (1H, m) 7.94 (1H, D, J=8.4 Hz), 8.36 (1H, dd, J=6.5, 3.0 Hz).

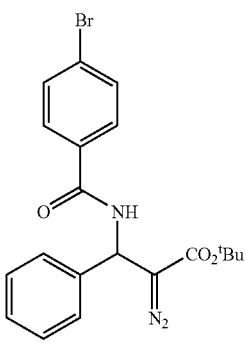

$^1$H NMR (270 MHz, CDCl$_3$): δ 1.46 (9H, s), 6.14 (1H, d, J=8.4 Hz), 7.31-7.39 (6H, m). 7.58 (1H, d, J=8.6 Hz). 7.58 (1H, d, J=8.6 Hz), 7.69 (1H, d, J=8.6 Hz).

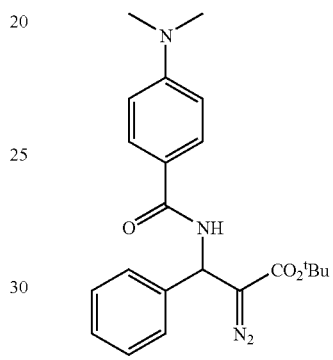

$^1$H NMR (270 MHz, CDCl$_3$): δ 1.45 (9H, s), 3.03 (6H, s), 6.17 (1H, d, J=8.4 Hz), 6.68 (2H, dt, J=9.2, 2.7 Hz), 7.20 (1H, brs), 7.27-7.44 (5H, m), 7.73 (2H, dt, J=8.9, 3.0 Hz).

TABLE 12

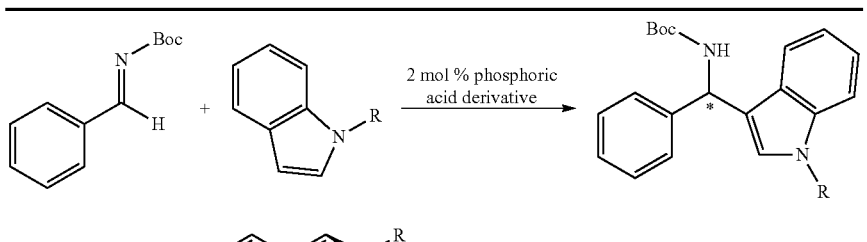

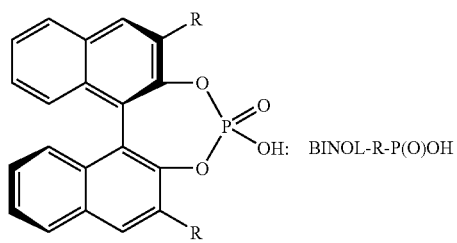

OH: BINOL-R-P(O)OH

| Entry | R | Phosphoric acid derivative | Solvent | Reaction temperature | Reaction time | Yield | Enantiomeric excess (% ee) |
|---|---|---|---|---|---|---|---|
| 1 | TBS | no | CDCl$_3$ | rt | 1 d | <5% conv | — |
| 2 | " | achiral | " | " | <10 min | quaint | — |
| 3 | " | 3,3-(4-Ph—C$_6$H$_4$—)-BINOL-P(O)OH | " | " | 2 h | 94% (>99% conv) | 27% (s) |
| 4 | " | 3,3-(3,5-Ph—C$_6$H$_3$—)-BINOL-P(O)OH | CDCl$_3$ | " | 8 h | 92% (>95% conv) | 69% (s) |

TABLE 12-continued

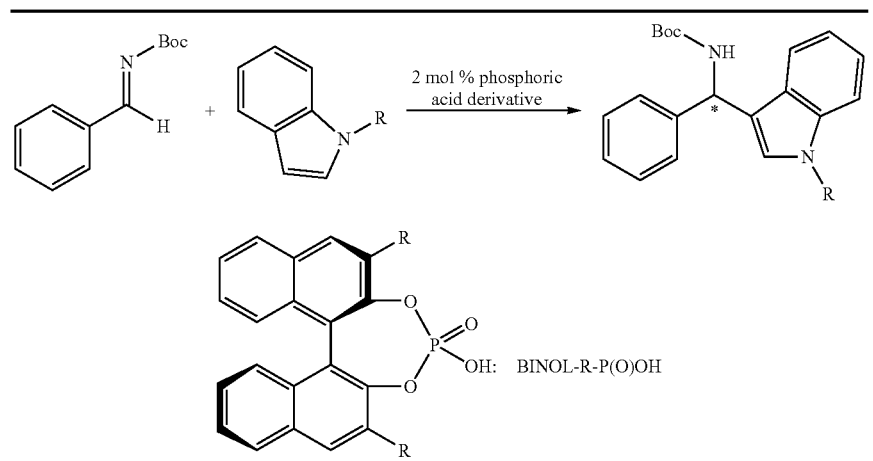

| Entry | R | Phosphoric acid derivative | Solvent | Reaction temperature | Reaction time | Yield | Enantiomeric excess (% ee) |
|---|---|---|---|---|---|---|---|
| 5 | " | 3,3-(3,5-Ph—$C_6H_3$—)-BINOL-P(O)OH | $CHCl_3$ | rt | 12 h | 79% | 67% (s) |
| 6 | " | 3,3-(3,5-Ph—$C_6H_3$—)-BINOL-P(O)OH | DCM | " | 12 h | 30% | 43% (s) |
| 7 | " | 3,3-(3,5-Ph—$C_6H_3$—)-BINOL-P(O)OH | " | 0 | 25 h | 35% | 52% (s) |
| 8 | " | 3,3-(3,5-Ph—$C_6H_3$—)-BINOL-P(O)OH | toluene | rt | 12 h | 84% | 60% (s) |
| 9 | " | 3,3-(3,5-Ph—$C_6H_3$—)-BINOL-P(O)OH | " | 0 | 25 h | 60% | 69% (s) |
| 10 | " | 3,3-(3,5-Ph—$C_6H_3$—)-BINOL-P(O)OH | ether | rt | " | 37% | 47% (s) |
| 11 | " | 3,3-(3,5-Ph—$C_6H_3$—)-BINOL-P(O)OH | Mesitylene | " | " | 69% | 48% (s) |
| 12 | " | 3,3-(3,5-Ph—$C_6H_3$—)-BINOL-P(O)OH | PhCl | " | " | 82% | 45% (s) |
| 13 | " | 3,3-(4-t-Bu—$C_6H_4$—)-BINOL-P(O)OH | $CDCl_3$ | " | 2.5 d | >62% (>95% conv) | 32% (s) |
| 14 | " | 3,3-(3,5-t-Bu—$C_6H_3$—)-BINOL-P(O)OH | " | " | 2 d | >63% (>95% conv) | 52% (s) |
| 15 | " | 3,3-(4-$CF_3$—$C_6H_4$—)-BINOL-P(O)OH | " | " | 23 h | 80% (>99% conv) | 9% (s) |
| 16 | " | 3,3-(3,5-$CF_3$—$C_6H_3$—)-BINOL-P(O)OH | " | " | 3.5 h | 92% (>99% conv) | 58% (s) |
| 17 | " | 3,3-(3,5-Me—$C_6H_3$—)-BINOL-P(O)OH | $CHCl_3$ | " | 12 h | 44% | 46% (s) |
| 18 | " | 3,3-(3,5-Br—$C_6H_3$—)-BINOL-P(O)OH | " | " | " | 80% | 57% (s) |
| 19 | " | 3,3-(3,5-TMS-$C_6H_3$—)-BINOL-P(O)OH | " | " | " | 62% | 27% (s) |
| 20 | " | 3,3-Br-BINOL-P(O)OH | " | " | " | 28% | 39% (s) |
| 21 | " | 3,3-β-Naph-BINOL-P(O)OH | " | " | " | 71% | 37% (s) |
| 22 | " | 3,3-(3,4,5-$F_3$—Ph)-BINOL-P(O)OH | " | " | " | 69% | 48% (s) |
| 23 | " | 3,3-(3,5-mes[17])-$C_6H_3$—)-BINOL-P(O)OH | " | " | " | 68% | 55% (f) |
| 24 | " | 3,3-(3,5-anth[18])-$C_6H_3$—)-BINOL-P(O)OH | " | " | " | 37% | 43% (f) |
| 25 | " | 3,3-(mes)-BINOL-P(O)OH | $CDCl_3$ | " | 5 h | 89% (>95% conv) | 24% (s) |
| 26 | " | 3,3-(anth)-BINOL-P(O)OH | " | " | 17 h | 78% (>99% conv) | 8% (f) |
| 27 | " | 3-3-(3,5-Ph—$C_6H_3$—)-BINOL-P(O)OH | toluene | −40° | 24 h | 67% | 80% (s) |
| 28 | " | 3-3-(3,5-Ph—$C_6H_3$—)-BINOL-P(O)OH | TCE | " | 21.5 h | 85% | 96% (s) |

In Table 12, expression of (f) and (s) is as follows: Upon enantiomer analysis in chiral HPLC analysis (column: Chiralpak AD-H, solvent: hexane/isopropanol=98/2 (V/V)), when a peak observed first is a main component, this is described as (f) and, when a peak observed afterward is a main component, this is described as (s).

Example 16

Under nitrogen atmosphere, 0.11 mmol of an indole derivative and 0.002 mmol of a phosphoric acid catalyst are weighed into a test tube, and dissolved in 1 mL of a solvent. At room temperature, 0.1 mmol of an imine compound is neat added, and this mixture is stirred for a time indicated in Table. Two drops of saturated aqueous sodium hydrogen carbonate solution were added to the reaction mixture, and the product is isolated by column chromatography. NMR of the product:

$^1$H NMR (CDCl$_3$, 270 MHz): δ 0.52 (3H, s), 0.53 (3H, s), 0.89 (9H, s), 1.45 (9H, brs), 5.20 (1H, brd, J=6.5 Hz), 6.19 (1H, brd, J=6.5 Hz), 6.76 (1H, s), 7.06 (1H, dt, J=1.1, 7.0 Hz), 7.15 (1H, dt, J=1.1, 7.0 Hz), 7.26-7.40 (5H, m), 7.44 (1H, d, J=8.5 Hz), 7.48 (1H, d, J=8.1 Hz).

TABLE 13

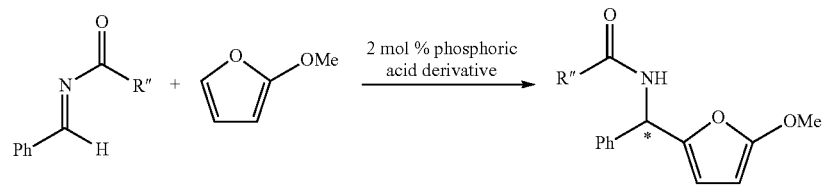

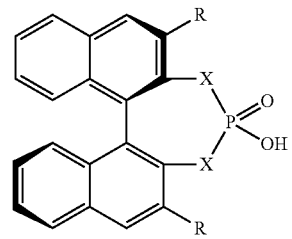

X = O: BINOL-R-P(O)OH
X = NR', R = H: BINAM-R'-P(O)OH

| | Phosphoric acid derivative | R'' | Solvent | Reaction time | Reaction temperature | Yield (%) | Enantiomeric excess (% ee) |
|---|---|---|---|---|---|---|---|
| 1 | achiral | Ph | CDCl$_3$ | 20 min | rt | 74 | — |
| 2 | BINOL-(4-Ph—C$_6$H$_4$)—P(O)OH | " | " | 10 min | " | 69 | 13 (s) |
| 3 | BINOL-(3,5-Ph—C$_6$H$_3$)—P(O)OH | " | " | 3 h | " | 76 | 9 (f) |
| 4 | BINOL-(4-t-Bu—C$_6$H$_4$)—P(O)OH | " | " | 5 h | " | 66 | 16 (f) |
| 5 | BINOL-(3,5-t-Bu—C$_6$H$_3$)—P(O)OH | " | " | 18 h | " | 70 | 9 (s) |
| 6 | BINOL-(4-CF$_3$—C$_6$H$_4$)—P(O)OH | " | " | 1.5 h | " | 61 | 17 (s) |
| 7 | BINOL-(3,5-CF$_3$—C$_6$H$_3$)—P(O)OH | " | " | 10 min | " | 66 | 14 (s) |
| 8 | achiral | tBuO | " | 20 min | " | 57 | — |
| 9 | BINOL-(4-Ph—C$_6$H$_4$)—P(O)OH | " | " | 10 min | " | 70 | 12 (S) |
| 10 | BINOL-(3,5-Ph—C$_6$H$_3$)—P(O)OH | " | " | 6 h | " | 82 | 17 (R) |
| 11 | BINOL-(4-t-Bu—C$_6$H$_4$)—P(O)OH | " | " | 2 d | " | 66 | rac |
| 12 | BINOL-(3,5-t-Bu—C$_6$H$_3$)—P(O)OH | " | " | 2 d | " | 70 | 10 (S) |
| 13 | BINOL-(4-CF$_3$—C$_6$H$_4$)—P(O)OH | " | " | 1 d | " | 74 | 4 (R) |
| 14 | BINOL-(3,5-CF$_3$—C$_6$H$_3$)—P(O)OH | " | " | 1.5 d | " | 78 | rac |
| 15 | BINAM-Tf-P(O)OH | " | " | 10 min | " | 84 | 21 (S) |
| 16 | BINAM-Ts-P(O)OH | " | " | 5 d | " | 56 | 24 (S) |
| 17 | BINOL-(3,5-mes-C$_6$H$_3$)—P(O)OH | tBuO | CHCl$_3$ | 4 h | rt | 74 | 42 (R) |
| 18 | " | " | CDCl$_3$ | 19.5 h | 0 | 83 | 84 (R) |
| 19 | " | " | DCM | 19 h | rt | 79 | 82 (R) |
| 20 | " | " | " | 21.5 h | 0 | 82 | 88 (R) |

In Table 13, expression of (f) and (s) is as follows: Upon enantiomer analysis in chiral HPLC analysis (column: Chiralpak AD-H, solvent: hexane/isopropanol=95/5 (V/V)), when a peak observed first is a main component, this is described as (f) and, when a peak observed afterward is a main component, this is described as (s).

TABLE 14

| | Phosphoric acid derivative | R'' | Solvent | Reaction time | Reaction temperature | Yield (%) | Enantiomeric excess (% ee) |
|---|---|---|---|---|---|---|---|
| 21 | BINOL-(3,5-mes-C$_6$H$_3$)—P(O)OH | tBuO | DCE | 21 h | 0 | 86 | 92 (R) |

TABLE 14-continued

| | Phosphoric acid derivative | R" | Solvent | Reaction time | Reaction temperature | Yield (%) | Enantiomeric excess (% ee) |
|---|---|---|---|---|---|---|---|
| 22 | BINOL-(3,5-mes-$C_6H_3$)—P(O)OH | " | " | 21 h | −20 | 89 | 95 (R) |
| 23 | BINOL-(3,5-mes-$C_6H_3$)—P(O)OH | " | " | 24 h | −35 | 87 | 96 (R) |
| 24 | BINOL-(3,5-mes-$C_6H_3$)—P(O)OH | " | TCE | 22 h | 0 | 87 | 90 (R) |
| 25 | BINOL-(3,5-mes-$C_6H_3$)—P(O)OH | " | toluene | 22 h | rt | 73 | 74 (R) |
| 26 | BINOL-(3,5-mes-$C_6H_3$)—P(O)OH | " | " | 1.5 d | 0 | 88 | 83 (R) |
| 27 | BINOL-(3,5-mes-$C_6H_3$)—P(O)OH | " | mesitylene | 21.5 h | 0 | 80 | 82 (R) |
| 28 | BINOL-(3,5-mes-$C_6H_3$)—P(O)OH | " | $PhCF_3$ | 19 h | 0 | 82 | 83 (R) |
| 29 | BINOL-(3,5-mes-$C_6H_3$)—P(O)OH | " | PhCl | 19.5 h | 0 | 79 | 83 (R) |
| 30 | BINOL-(3,5-mes-$C_6H_3$)—P(O)OH | " | $iPr_2O$ | 19) | rt | 73 | 70 (R) |
| 31 | BINOL-(3,5-mes-$C_6H_3$)—P(O)OH | " | " | 19.5 h | 0 | 80 | 79 (R) |
| 32 | BINOL-(3,5-mes-$C_6H_3$)—P(O)OH | " | ether | 22 h | rt | 69 | 66 (R) |
| 33 | BINOL-(3,5-mes-$C_6H_3$)—P(O)OH | " | THF | 21 h | 0 | 70 | 83 (R) |
| 34 | BINOL-(3,5-mes-$C_6H_3$)—P(O)OH | " | cHex | 19.5 h | 0 | 75 | 76 (R) |
| 35 | BINOL-(3,5-mes-$C_6H_3$)—P(O)OH | BnO | $CDCl_3$ | 30 min | rt | 71 | rac |
| 36 | BINOL-(3,5-mes-$C_6H_3$)—P(O)OH | MeO | " | 4 h | rt | — | rac |
| 37 | BINOL-(3,5-anth-$C_6H_3$)—P(O)OH | tBuO | $CDCl_3$ | 19.5 h | rt | 66 | 33 (R) |
| 38 | BINOL-(3,5-anth-$C_6H_3$)—P(O)OH | " | toluene | 1.5 d | 0 | 73 | 35 (R) |
| 39 | BINOL-(mes)-P(O)OH | tBuO | DCM | 19 h | rt | 53 | 53 (R) |
| 40 | BINOL-(anth)-P(O)OH | " | DCM | 19 h | rt | 61 | 44 (R) |

TABLE 15

Boc-N=CHR (1.0 eq (0.1 mmol)) + 2-OMe-furan (1.2 eq (0.12 mmol)) → HN(Boc)–CHR*–(5-OMe-furan-2-yl), with 2 mol % catalyst in DCE (1 ml).

Catalyst: BINOL-3,3'-bis(3,5-mes-Ph) phosphoric acid.

| Entry | Substituent (R=) | Time | Reaction temperature (° C.) | Yield (%) | Optical yield (%) |
|---|---|---|---|---|---|
| 1 | $C_6H_5$— | 24 h | −20 | 89 | 95 |
| 2 | " | " | −35 | 87 | 97 |
| 2[a] | " | 40 h | " | 89 | 97 |
| 2[b] | " | 24 h | " | 95 | 97 |
| 3 | p-MeO—$C_6H_4$— | " | " | 95 | 96 |
| 4 | o-Me—$C_6H_4$— | " | " | 84 | 94 |
| 5 | m-Me—$C_6H_4$— | " | " | 80 | 94 |
| 6 | p-Me—$C_6H_4$— | " | " | 96 | 97 |
| 7 | o-Br—$C_6H_4$— | " | " | 85 | 91 |
| 8 | m-Br—$C_6H_4$— | " | " | 89 | 96 |
| 9 | p-Br—$C_6H_4$— | " | " | 86 | 96 |
| 10 | p-F—$C_6H_4$— | " | " | 82 | 97 |
| 11 | p-Cl—$C_6H_4$— | " | " | 88 | 97 |
| 12 | α-naph- | " | " | 84 | 86 |
| 13 | β-naph- | " | " | 93 | 96 |
| 14 | Furyl- | " | " | 94 | 86 |

[a] catalyst(1.0 mol %).
[b] large scale (imine 1 (5.0 mmol)) in the presence of 0.5 mol % catalyst.

Example 17

Example of Bz-protected imine: Under nitrogen atmosphere, 0.002 mmol of a catalyst 1 and 0.1 mmol of imine are dissolved in 1 mL of a solvent in a test tube. To the resulting pale yellow solution is neat added 0.12 mmol of 2-methoxyfuran at room temperature with stirring. After 24 hours, to the reaction solution are added two drops of saturated aqueous sodium hydrogen carbonate solution, and the product is purified by column chromatography.

Example 18

Example of Boc-protected imine: Under nitrogen atmosphere, 0.002 mmol of a catalyst 1 is dissolved in 1 mL of a solvent in a test tube. To the resulting pale yellow solution is added 0.1 mmol of imine at room temperature with stirring, and 0.12 mmol of 2-methoxyfuran is neat added at −35° C. After 24 hours, to the reaction solution are added two drops of saturated aqueous sodium hydrogen carbonate solution, and the product is purified by column chromatography.

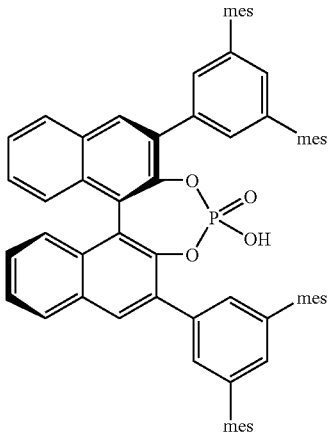

2,6-Bis-(2,4,6,2",4",6"-hexamethyl-[1,1';3',1"]terphenyl-5'-yl)-4-ox-3,5-dioxa-4λ5-phospha-cyclohepta[2,1-a;3,4-a']dinaphthalen-4-ol]((R)-4)

white solid; Rf=0.45 (Hexane/EtOAc=1/1);
1H NMR (270 MHz, DMSO-$d_6$): δ 2.06 (24H, s), 2.23 (12H, s), 6.75 (2H, s), 6.89 (8H, brs), 7.11 (2H, d, J=8.1 Hz), 7.22 (2H, t, J=8.1 Hz), 7.45 (2H, t, J=8.1 Hz), 7.58 (4H, s), 8.10 (2H, t, J=8.1 Hz), 8.27 (2H, s);
$^{13}$C NMR (67.8 MHz, DMSO-$d_6$): δ 20.6, 122.4 (d, $J_{P-C}$=2.4 Hz), 125.4, 125.9, 126.6, 127.8, 127.9, 128.6, 128.8, 128.9, 130.7, 130.8, 131.5, 133.5 (d, $J_{P-C}$=2.0 Hz), 135.2, 135.3, 135.8, 137.3, 138.5, 140.4, 145.6 (d, $J_{P-C}$=9.8 Hz);
$^{31}$P NMR (162 MHz, DMSO-$d_6$): δ 3.92;
IR (KBr): 3400, 2918, 2860, 1612, 1595, 1483, 1439, 1240, 1101, 1020, 982, 885, 851, 750, 693 cm$^{-1}$;
HRMS (ESI) Calcd for $C_{68}H_{60}O_4P$ ([M-H]$^-$) 971.4235. Found 971.4235.

Representative Procedure for the Phosphoric Acid Catalyzed Aza-Friedel-Crafts Alkylation of 2-Methoxyfuran:

1.95 mg of (R)-4 (2 mol %, 0.002 mmol) was weighed in a dry test tube, and this was placed under nitrogen atmosphere. A phosphoric acid derivative catalyst was dissolved in 1 mL of 1,2-dichloroethane. 20.5 mg of N-boc-protected imine (R=Ph, 0.1 mmol) and 11.1 μL of 2-methoxyfuran (1, 1.2 equiv, 0.12 mmol) were neat added at −35° C. The resulting solution was stirred for 24 hours under the same condition. The reaction mixture was charged onto a silica gel column, and purified by column chromatography (eluent: Hexane/EtOAc=12/1 to 8/1). Furan-2-yl amine entity (R=Ph) was obtained as a white solid in a yield of 87%. An enantiomeric excess was determined by HPLC analysis.

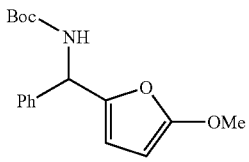

tert-butyl (5-methoxyfuran-2-yl)(phenyl)methylcarbamate (R=Ph):

R$_f$=0.40 (Hexane/EtOAc=1/4);

HPLC analysis Chiralpak AD-H (Hexane/$^i$PrOH=95/5, 1.0 mL/min, 254 nm, 10° C.) 14.9 (major), 18.0 min;
$^1$H NMR (CDCl$_3$, 270 MHz): δ 1.43 (9H, brs), 3.80 (3H, s), 5.04 (1H, d, J=3.1 Hz), 5.24 (1H, br), 5.79 (1H, br), 5.94 (1H, d, J=3.1 Hz), 7.23-7.38 (5H, m);
$^{13}$C NMR (CDCl$_3$, 67.8 MHz): δ 28.3, 52.6, 57.7, 79.7, 79.8, 108.7, 126.9, 127.5, 128.5, 139.9, 143.6, 154.8, 161.4;
IR (KBr): 3354, 2984, 2943, 1678, 1614, 1585, 1518, 1367, 1319, 1256, 1163, 1043, 1009, 947, 880, 746 cm$^{-1}$;
HRMS (ESI) Calcd for $C_{17}H_{21}NANO_4$ ([M+Na]$^+$) 326.1363. Found 326.1364.

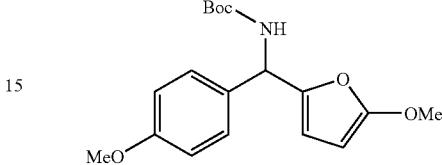

tert-butyl (5-methoxyfuran-2-yl)(4-methoxyphenyl)methylcarbamate (R=p-MeO-$C_6H_5$):

R$_f$=0.32 (Hexane/EtOAC=1/4);
HPLC analysis Chiralpak AD-H (Hexane/EtOH=95/5, 1.0 mL/min, 254 nm, 10° C.) 29.2, 34.0 (major) min;
$^1$H NMR (CDCl$_3$, 270 MHz): δ 1.42 (9H, brs), 3.79 (3H, s), 3.80 (3H, s), 5.03 (1H, d, J=3.2 Hz), 5.17 (1H, br), 5.72 (1H, br), 5.92 (1H, br), 6.85 (2H, d, J=8.9 Hz), 7.22 (2H, d, J=8.9 Hz);
$^{13}$C NMR (CDCl$_3$, 67.8 MHz): δ 28.3, 52.1, 52.2, 57.7, 79.7, 79.8, 108.5, 113.8, 128.0, 132.2, 143.9, 154.8, 159.0, 161.4;
IR (KBr): 3385, 2980, 2841, 1711, 1612, 1585, 1514, 1367, 1252, 1165, 1032, 943, 827 cm$^{-1}$;
HRMS (ESI) Calcd for $C_{18}H_{23}NaNO_5$ ([M+Na]$^+$) 356.1468. Found 356.1469.

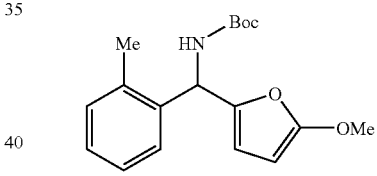

tert-butyl (5-methoxyfuran-2-yl)(o-tolyl)methylcarbamate (R=o-Me-$C_6H_5$):

R$_f$=0.40 (Hexane/EtOAc=1/4);
HPLC analysis Chiralpak AD-H (Hexane/$^i$PrOH=95/5, 0.7 mL/min, 254 nm, 10° C.) 16.1 (major), 19.3 min;
$^1$H NMR (CDCl$_3$, 270 MHz): δ 1.43 (9H, brs), 2.35 (3H, s), 3.80 (3H, s), 5.02 (1H, d, J=3.0 Hz), 5.18 (1H, br), 5.82 (1H, brd, J=3.0 Hz), 5.95 (1H, br), 7.16-7.30 (4H, m);
$^{13}$C NMR (CDCl$_3$, 67.8 MHz): δ 19.0, 28.3, 49.6, 57.6, 79.7, 79.8, 108.9, 126.0, 126.1, 127.5, 130.5, 135.8, 138.0, 143.3, 154.7, 161.4;
IR (KBr): 3319, 2964, 2936, 1709, 1682, 1618, 1585, 1526, 1366, 1263, 1173, 1057, 1018, 947, 883, 760, 746 cm$^{-1}$;
HRMS (ESI) Calcd for $C_{18}H_{23}NaNO_4$ ([M+Na]$^+$) 340.1519. Found 340.1520.

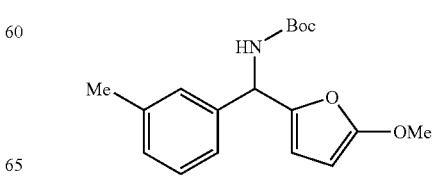

tert-butyl (5-methoxyfuran-2-yl)(m-tolyl)methylcarbamate (R=m-Me-C$_6$H$_5$):

$R_f$=0.40 (Hexane/EtOAc=1/4);

HPLC analysis Chiralpak AD-H (Hexane/$^i$PrOH=95/5, 1.0 mL/min, 254 nm, 10° C.) 12.4 (major), 14.2 min;

$^1$H NMR (CDCl$_3$, 270 MHz): δ 1.43 (9H, brs), 2.33 (3H, s), 3.80 (3H, s), 5.04 (1H, d, J=3.2 Hz), 5.21 (1H, br), 5.74 (1H, br), 5.94 (1H, brd, J=3.2 Hz), 7.06-7.11 (3H, m), 7.19-7.26 (1H, m);

$^{13}$C NMR (CDCl$_3$, 67.8 MHz): δ 21.4, 28.3, 52.7, 57.7, 79.7, 79.8, 108.6, 123.9, 127.6, 128.3, 128.4, 138.1, 139.8, 143.8, 154.8, 161.4;

IR (KBr): 3387, 2964, 2937, 1686, 1614, 1578, 1516, 1333, 1259, 1169, 1057, 1018, 945, 883, 748 cm$^{-1}$;

HRMS (ESI) Calcd for C$_{18}$H$_{23}$NaNO$_4$ ([M+Na]$^+$) 340.1519. Found 340.1522.

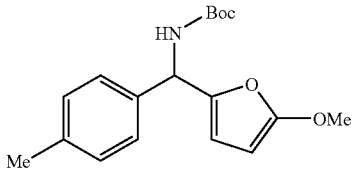

tert-butyl (5-methoxyfuran-2-yl)(p-tolyl)methylcarbamate (R=p-Me-C$_6$H$_5$):

$R_f$=0.40 (Hexane/EtOAc=1/4);

HPLC analysis Chiralpak AD-H (Hexane/$^i$PrOH=95/5, 0.7 mL/min, 254 nm, 10° C.) 23.0 (major), 26.1 min;

$^1$H NMR (CDCl$_3$, 270 MHz): δ 1.43 (9H, brs), 2.33 (3H, s), 3.80 (3H, s), 5.03 (1H, d, J=3.1 Hz), 5.19 (1H, br), 5.76 (1H, br), 5.93 (1H, d, J=3.1 Hz), 7.13 (2H, d, J=8.1 Hz), 7.20 (2H, d, J=8.1 Hz);

$^{13}$C NMR (CDCl$_3$, 67.8 MHz): δ 21.1, 28.3, 52.4, 57.7, 79.7$_0$, 79.7$_3$, 108.5, 126.8, 129.2, 137.0, 137.2, 143.9, 154.8, 161.4;

IR (KBr): 3364, 2978, 2936, 1705, 1614, 1578, 1493, 1367, 1259, 1165, 1047, 1020, 951, 878, 783 cm$^{-1}$;

HRMS (ESI) Calcd for C$_{18}$H$_{23}$NaNO$_4$ ([M+Na]$^+$) 340.1519. Found 340.1522.

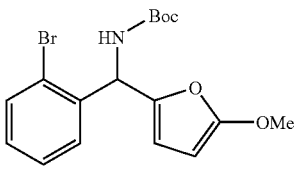

tert-butyl (2-bromophenyl)(5-methoxyfuran-2-yl)methylcarbamate (R=o-Br—C$_6$H$_5$):

$R_f$=0.32 (Hexane/EtOAc=1/4);

HPLC analysis Chiralpak AD-H (Hexane/$^i$PrOH=95/5, 1.0 mL/min, 254 nm, 10° C.) 15.2 (major), 21.0 min;

$^1$H NMR (CDCl$_3$, 270 MHz): δ 1.42 (9H, brs), 3.78 (3H, s), 5.02 (1H, d, J=3.2 Hz), 5.29 (1H, br), 5.89 (1H, d, J=3.2 Hz), 6.11 (1H, br), 7.14 (1H, dt, J=7.6, 1.6 Hz), 7.32 (1H, dt, J=7.6, 1.1 Hz), 7.42 (1H, br), 7.54 (1H, dd, J=7.6, 1.1 Hz);

$^{13}$C NMR (CDCl$_3$, 67.8 MHz): δ 28.3, 52.6, 57.7, 79.9, 80.0, 109.5, 123.4, 127.5, 128.0, 129.0, 133.1, 139.0, 142.1, 154.5, 161.5;

IR (KBr): 3389, 2978, 2936, 1690, 1614, 1572, 1510, 1391, 1323, 1258, 1161, 1057, 1018, 943, 881, 766, 752 cm$^{-1}$;

HRMS (ESI) Calcd for C$_{17}$H$_{20}$BrNaNO4 ([M+Na]$^+$) 404.0468, 406.0447. Found 404.0468, 406.0445.

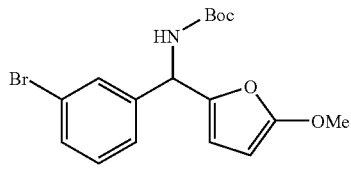

tert-butyl (3-bromophenyl)(5-methoxyfuran-2-yl)methylcarbamate (R=m-Br—C$_6$H$_5$):

$R_f$=0.42 (Hexane/EtOAc=1/4);

HPLC analysis Chiralpak AD-H (Hexane/EtOH=95/5, 0.5 mL/min, 254 nm, 10° C.) 27.4, 31.1 (major) min;

$^1$H NMR (CDCl$_3$, 270 MHz): δ 1.43 (9H, brs), 3.81 (3H, s), 5.04 (1H, d, J=3.2 Hz), 5.23 (1H, br), 5.74 (1H, br), 5.95 (1H, d, J=3.2 Hz), 7.40 (1H, dt, J=7.3, 1.6 Hz), 7.46 (1H, d, J=1.6 Hz);

$^{13}$C NMR (CDCl$_3$, 67.8 MHz): δ 28.3, 52.2, 57.7, 79.8, 80.2, 109.2, 122.6, 125.6, 129.9, 130.0, 130.7, 142.3, 142.7, 154.7, 161.6;

IR (KBr): 3375, 2976, 2936, 1692, 1614, 1578, 1518, 1367, 1337, 1259, 1171, 1045, 970, 951, 781, 735 cm$^{-1}$;

HRMS (ESI) Calcd for C$_{17}$H$_{20}$BrNaNO$_4$ ([M+Na]$^+$) 404.0468, 406.0447. Found 404.0468, 406.0444.

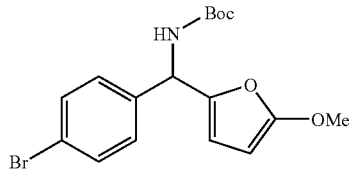

tert-butyl (4-bromophenyl)(5-methoxyfuran-2-yl)methylcarbamate (R=p-Br—C$_6$C$_5$):

$R_f$=0.38 (Hexane/EtOAc=1/4);

HPLC analysis Chiralpak AD-H (Hexane/$^i$PrOH=95/5, 1.0 mL/min, 254 nm, 10° C.) 16.1 (major), 19.4 min;

$^1$H NMR (CDCl$_3$, 270 MHz): δ 1.42 (9H, brs), 3.80 (3H, s), 5.03 (1H, d, J=3.2 Hz), 5.23 (1H, br), 5.72 (1H, br), 5.93 (1H, d, J=3.2 Hz), 7.19 (2H, d, J=8.4 Hz), 7.45 (2H, d, J=8.4 Hz);

$^{13}$C NMR (CDCl$_3$, 67.8 MHz): δ 28.3, 52.1, 57.7, 79.8, 80.1, 109.1, 121.4, 128.6, 131.6, 139.1, 142.8, 154.7, 161.6;

IR (KBr): 3368, 2978, 2937, 1684, 1614, 1585, 1516, 1369, 1340, 1250, 1165, 1047, 1011, 951, 880, 729 cm$^{-1}$;

HRMS (ESI) Calcd for C$_{17}$H$_{20}$BrNaNO$_4$ ([M+Na]$^+$) 404.0468, 406.0447. Found 404.0468, 406.0446.

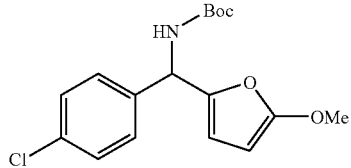

tert-butyl (4-bromophenyl)(4-chlorophenyl)(5-methoxyfuran-2-yl)methylcarbamate (R=p-C$_1$-C$_6$C$_5$):

$R_f$=0.36 (Hexane/EtOAc=1/4);

HPLC analysis Chiralpak AD-H (Hexane/$^i$PrOH=95/5, 1.0 mL/min, 254 nm, 10° C.) 14.7 (major), 17.5 min;

$^1$H NMR (CDCl$_3$, 270 MHz): δ 1.43 (9H, brs), 3.80 (3H, s), 5.04 (1H, d, J=3.0 Hz), 5.20 (1H, br), 5.74 (1H, br), 5.92 (1H, brd, J=3.0 Hz), 7.23-7.32 (4H, m);

$^{13}$C NMR (CDCl$_3$, 67.8 MHz): δ 28.3, 52.1, 57.7, 79.8, 80.1, 109.1, 128.2, 128.6, 133.3, 138.6, 143.0, 154.7, 161.6;

IR (KBr): 3356, 2980, 2936, 1707, 1618, 1585, 1491, 1367, 1261, 1167, 1092, 1047, 1015, 947, 883, 822 cm$^{-1}$;

HRMS (ESI) Calcd for $C_{17}H_{20}ClNaNO_4$ ([M+Na]$^+$) 360.0973. Found 360.0970.

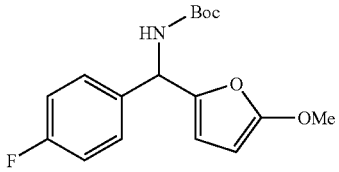

tert-butyl (4-fluorophenyl)(5-methoxyfuran-2-yl)methylcarbamate (R=p-F—$C_6C_5$):

$R_f$=0.40 (Hexane/EtOAc=1/4);

HPLC analysis Chiralpak AD-H (Hexane/$^i$PrOH=95/5, 0.7 mL/min, 254 nm, 10° C.) 20.0 (major), 24.0 min;

$^1$H NMR (CDCl$_3$, 270 MHz): δ 1.43 (9H, brs), 3.81 (3H, s), 5.04 (1H, d, J=3.2 Hz), 5.21 (1H, br), 5.75 (1H, br), 5.93 (1H, brd, J=3.2 Hz), 6.98-7.04 (2H, m), 7.25-7.30 (2H, m);

$^{13}$C NMR (CDCl$_3$, 67.8 MHz): δ 28.3, 52.0, 57.7, 79.7, 80.0, 108.9, 115.3 (d, $J_{F-C}$=21.6 Hz), 128.5 (d, $J_{F-C}$=8.3 Hz), 135.8 (d, $J_{F-C}$=3.9 Hz), 143.3, 154.8, 161.5, 162.2 (d, $J_{F-C}$=245.1 Hz);

IR (KBr): 3373, 2980, 2943, 1690, 1612, 1585, 1526, 1371, 1306, 1265, 1177, 1057, 1016, 951, 883, 847, 743 cm$^{-1}$;

HRMS (ESI) Calcd for $C_{17}H_{20}FNaNO_4$ ([M+Na]$^+$) 344.1269. Found 344.1269.

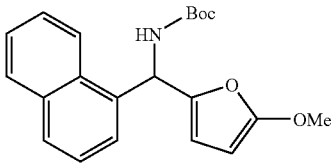

tert-butyl (5-methoxyfuran-2-yl)(naphthalene-2-yl)methylcarbamate (R=1-Naphthyl):

Rf=0.38 (Hexane/EtOAc=1/4);

HPLC analysis Chiralpak AD-H (Hexane/$^i$PrOH=97/3, 1.0 mL/min, 254 nm, 10° C.) 27.1, 29.5 (major) min;

$^1$H NMR (CDCl$_3$, 270 MHz): δ 1.44 (9H, brs), 3.80 (3H, s), 5.04 (1H, d, J=3.2 Hz), 5.24 (1H, br), 5.92 (1H, br), 6.59 (1H, brd, J=6.8 Hz), 7.42-7.54 (4H, m), 7.78-7.88 (2H, m), 8.07 (1H, brd, J=6.8 Hz);

$^{13}$C NMR (CDCl$_3$, 67.8 MHz): δ 28.3, 49.6, 57.7, 79.9, 80.0, 109.2, 123.3, 124.3, 125.2, 125.7, 126.4, 128.5, 128.7, 130.9, 133.9, 135.6, 143.5, 154.7, 161.3;

IR (KBr): 3387, 2978, 2937, 1690, 1616, 1582, 1508, 1367, 1261, 1167, 1053, 1018, 945, 883, 779 cm$^{-1}$;

HRMS (ESI) Calcd for $C_{21}H_{23}NaNO_4$ ([M+Na]$^+$) 376.1519. Found 376.1518

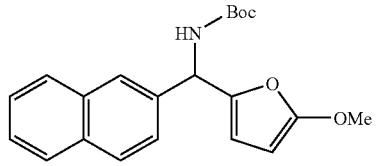

tert-butyl 5-methoxyfuran-2-yl)(naphthalene-2-yl)methylcarbamate (R=2-Naphthyl):

Rf=0.38 (Hexane/EtOAc=1/4);

HPLC analysis Chiralpak AD-H (Hexane/EtOH=95/5, 1.0 mL/min, 254 nm, 10° C.) 25.3, 30.7 (major) min;

$^1$H NMR (CDCl$_3$, 270 MHz): δ 1.44 (9H, brs), 3.81 (3H, s), 5.05 (1H, d, J=3.1 Hz), 5.30 (1H, br), 6.00 (1H, br), 7.41-7.48 (3H, m), 7.77-7.83 (4H, m);

$^{13}$C NMR (CDCl$_3$, 67.8 MHz): δ 28.3, 52.9, 57.7, 79.8, 80.0, 109.0, 125.1, 125.5, 125.9, 126.1, 127.6, 128.0, 128.3, 132.9, 133.3, 137.3, 143.6, 154.9, 161.5;

IR (KBr): 3315, 2968, 2937, 1713, 1680, 1614, 1582, 1526, 1371, 1261, 1167, 1049, 1020, 945, 864, 750 cm-1;

HRMS (ESI) Calcd for $C_{21}H_{23}NaNO_4$ ([M+Na]$^+$) 376.1519. Found 376.1520.

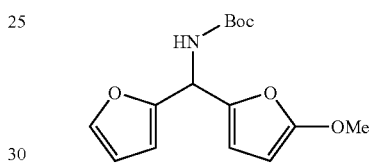

tert-butyl(furan-2-yl)(5-methoxyfuran-2-yl)methylcarbamate (R=2-Furyl):

$R_f$=0.38 (Hexane/EtOAc=1/4);

HPLC analysis Chiralpak AD-H (Hexane/$^i$PrOH=95/5, 1.0 mL/min, 254 nm, 10° C.) 15.3 (major), 19.2 min;

1H NMR (CDCl$_3$, 270 MHz): δ 1.43 (9H, brs), 3.82 (3H, s), 5.07 (1H, d, J=3.2 Hz), 5.19 (1H, br), 5.88 (1H, br), 6.07 (1H, d, J=3.2 Hz), 6.22 (1H, d, J=3.2 Hz), 6.31 (1H, dd, J=3.2, 2.2 Hz), 7.36 (1H, d, J=2.2 Hz);

$^{13}$C NMR (CDCl$_3$, 67.8 MHz): δ 28.3, 46.9, 57.7, 79.9, 80.0, 107.0, 108.6, 110.3, 141.6, 142.2, 152.1, 154.7, 161.3;

IR (KBr): 3348, 2980, 2936, 1717, 1618, 1585, 1506, 1369, 1261, 1167, 1047, 1013, 949, 872, 741 cm$^{-1}$;

HRMS (ESI) Calcd for $C_{15}H_{19}NaNO_5$ ([M+Na]$^+$) 316.1155. Found 316.1157.

Example 19

Friedel-Crafts Alkylating Reaction of N-TBS-Pyrrole

In an NMR tube under nitrogen atmosphere, 0.1 mmol of imine is added to a solution of 2 mol % catalyst in CDCl$_3$ (800 mL), and the mixture is stirred. At room temperature, N-TBS-protected pyrrole (0.11 mmol) is neat added, and this is mixed by shaking. The reaction is traced by NMR measurement, and after confirmation of complete consumption of the imine, 1 mL of hexane is added, followed by purification by column chromatography.

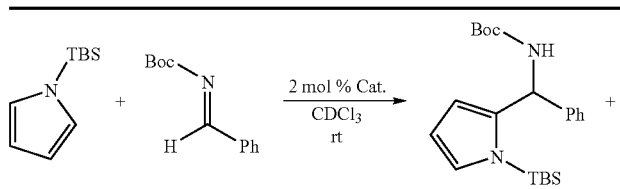

-continued

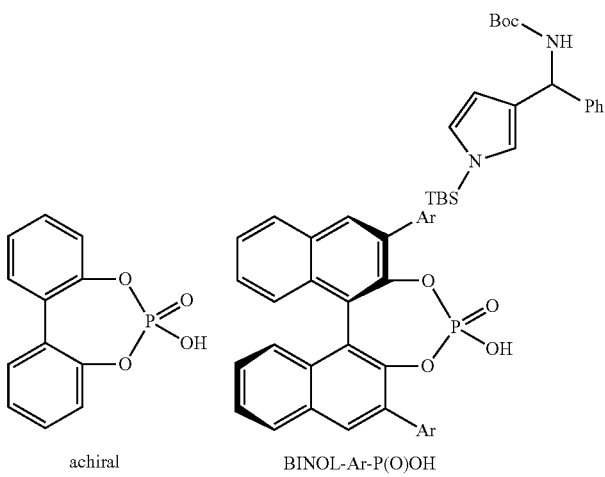

| | time | yield | regioselectivity (ee) |
|---|---|---|---|
| achiral | 10 min | 70% | 10 (rac):1 (rac) |
| BINOL-(3,5-terphenyl)-P(O)OH | 4.5 h | 82% | 5 (rac):1 (50% ee (f)) |
| BINOL-(3,5-mesitylphenyl)-P(O)OH | 27.5 h | 81% | 4 (24% ee (f)):1 (55% ee (b)) |

NMR of Product:
Main Product (Alkylation at Position 2):
$^1$H NMR (CDCl$_3$, 270 MHz): δ 0.51 (3H, s), 0.57 (3H, brs), 0.96 (9H, s), 1.43 (9H, brs), 5.08 (1H, brd, J=7.6 Hz), 5.79 (1H, dd, J=2.7, 1.6 Hz), 5.93 (1H, d, J=7.6 Hz), 6.13 (1H, t, J=3.0 Hz), 6.78 (1H, dd, J=2.7, 1.6 Hz), 7.20-7.36 (5H, m).

HPLC chiral-pak OD-H hexane/IPA=99.2/0.8, 0.5 mL/min, 12.0 min, 13.1 min.

By-Product (Alkylation at Position 3):
$^1$H NMR (CDCl$_3$, 270 MHz): δ 0.37 (6H, s), 0.85 (9H, s), 1.30 (9H, brs), 4.76 (1H, br), 5.86 (1H, br), 6.46 (1H, br), 6.69 (1H, t, J=2.4 Hz), 7.20-7.36 (5H, m) one proton missing.

HPLC chiralcel OD-H hexane/IPA=99.2/0.8, 0.5 mL/min, 17.4 min, 18.3 min.

Example 20

Friedel-Crafts Alkylating Reaction of 1,3,5-trimethoxybenzene

In an NMR tube under nitrogen atmosphere, 0.1 mmol of imine is added to a solution of 2 mol % catalyst in CDCl$_3$ (800 mL), and the mixture is stirred. 1,3,5-Trimethoxybenzene (0.11 mmol) is added at room temperature, and this is mixed by shaking. The reaction is traced by NMR measurement, and after confirmation of complete consumption of the imine, two drops of a saturated aqueous sodium hydrogen carbonate solution are added, followed by purification by column chromatography.

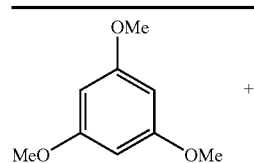

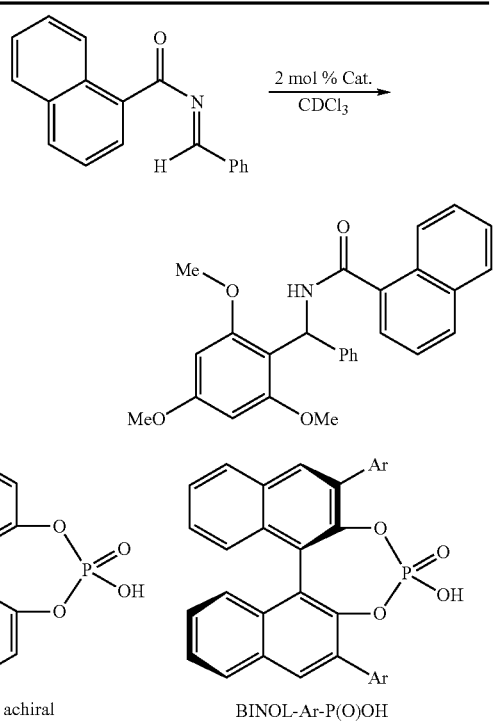

| | time | yield | ee |
|---|---|---|---|
| achiral | 10 min | 95% | rac |
| BINOL-(9-anthryl)-P(O)OH | 9 h | 90% | 45% ee (f) |

NMR of the Product:
$^1$H NMR (CDCl$_3$, 270 MHz): δ 3.78 (6H, s), 3.81 (3H, s), 6.21 (2H, s), 6.21-7.55 (9H, m), 7.67 (1H, d, J=7.0 Hz), 7.80-7.93 (3H, m), 8.36 (1H, m).

HPLC chiralcel OD-H hexane/IPA=90/10, 1.0 mL/min, 22.7 min, 27.9 min.

Example 21

Preparation of Phosphoric Acid Derivative Used in Example 18

Preparation of (R)-2,6-bis-(2,4,6,2'',4'',6''-hexamethyl-[1,1';3',1'']terphenyl-5'-yl)-4-oxo-3,5-dioxa-4λ⁵-phospha-cyclohepta[2,1-a;3,4-a']dinaphthalene-4-ol (R)-3,3'-bis-(3,5-dimesitylphenyl-[1,1']binaphthalenyl-2,2'-diol (0.5 mmol) was dissolved in 1 mL of pyridine under nitrogen atmosphere, phosphorus oxychloride (1.5 to 2.0 equivalent) was added to the solution at room temperature, and the mixture was stirred to react at 80° C. for 3 hours. Then, 1 mL of water was added to the reaction solution, and this was further stirred at 80° C. for 3 hours. After addition of dichloromethane and 1N hydrochloric acid to the reaction solution, the organic layer was dried over sodium sulfate, and purified by column chromatography to obtain the desired title compound as a white solid.

Example 22

Preparation of (R)-2,6-bis(1,1'-naphthyl)-4-oxo-3,5-dioxa-4λ⁵-phospha-cyclohepta[2,1-a;3,4-a']dinaphthalene-4-ol According to the same manner as described in Example 21 except that (R)-3,3'-bis-(4-naphthalene-2-yl-phenyl-[1,1']binaphthalenyl-2,2'-diol was used in place of (R)-3,3'-bis-(3,5-dimesitylphenyl-[1,1']binaphthalenyl-2,2'-diol, the reaction was performed to obtain the objective title compound.

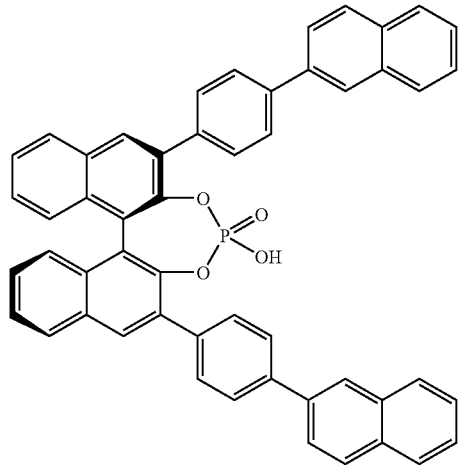

white solid; $R_f$=0.75 (CH$_2$Cl$_2$/$^i$PrOH=10/1); $^1$H-NMR (270 MHz, DMSO-d$_6$) δ 7.09 (2H, d, J=8.1 Hz), 7.29 (2H, td, J=6.8, 1.1 Hz), 7.45 (2H, t, J=8.1 Hz), 7.48-7.59 (4H, m), 7.93-8.06 (12H, m), 8.09 (2H, d, J=8.1 Hz), 8.17 (2H, s), 8.22 (2H, d, J=8.4 Hz), 8.35 (2H, s); $^{13}$C-NMR (67.8 MHz, DMSO-d$_6$) δ 122.7 (d, $J_{P-C}$=2.0 Hz), 124.8, 125.0, 125.2, 126.0, 126.1, 126.2, 126.4, 126.5, 126.6, 127.5, 128.2, 128.5, 130.1, 130.2, 131.0, 131.9 (d, $J_{P-C}$=1.0 Hz), 132.3, 133.4, 133.9 (d, $J_{P-C}$=2.4 Hz), 137.2, 137.3, 138.5, 147.4 (d, $J_{P-C}$=9.3 Hz); $^{31}$P NMR (162 MHz, DMSO-d$_6$) δ 3.19; IR (KBr): 3393, 3053, 2924, 1630, 1655, 1599, 1502, 1421, 1400, 1250, 1184, 1103, 972, 854, 837, 816, 748 cm$^{-1}$; HRMS (ESI) Calcd for C$_{52}$H$_{32}$O$_4$P ([M−H]$^-$) 751.2044. Found 751.2055.

What is claimed is:

1. A phosphoric acid derivative represented by the following formula:

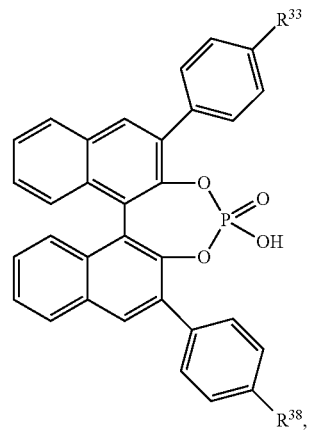

wherein R$^{33}$ and R$^{38}$ each independently represent a phenyl group, an α-naphthyl group or a β-naphthyl group.

2. The phosphoric acid derivative according to claim 1, wherein the phosphoric acid derivative represented by the formula is an optically active phosphoric acid derivative.

3. A phosphoric acid derivative represented by the following formula (32):

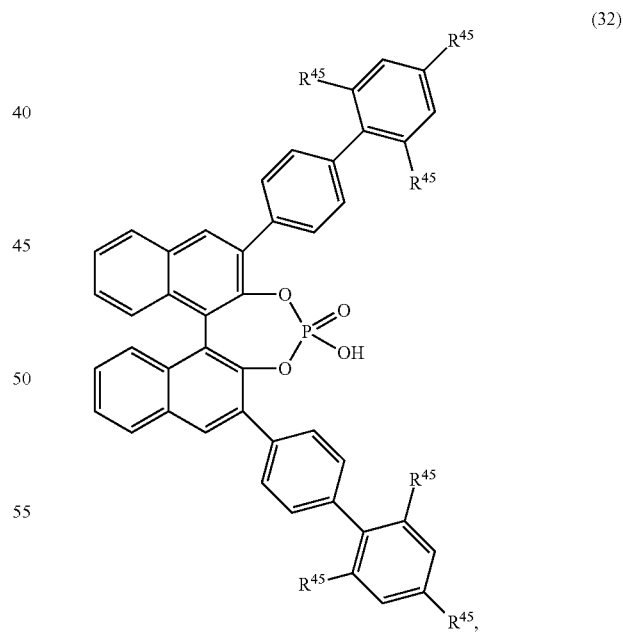

(32)

wherein R$^{45}$ represents an alkyl group.

4. The phosphoric acid derivative according to claim 3, wherein the phosphoric acid derivative represented by the formula (32) is an optically active phosphoric acid derivative.

* * * * *